US 6,927,291 B2

(12) United States Patent
Jin et al.

(10) Patent No.: US 6,927,291 B2
(45) Date of Patent: Aug. 9, 2005

(54) METHOD FOR THE SYNTHESIS OF 2',3'-DIDEOXY-2',3'-DIDEHYDRONUCLEOSIDES

(75) Inventors: Fuqiang Jin, Wilmington, DE (US); Pasquale N. Confalone, Greenville, DE (US)

(73) Assignee: Pharmasset, Ltd., Tucker, GA (US)

( * ) Notice: Subject to any disclaimer, the term of this patent is extended or adjusted under 35 U.S.C. 154(b) by 109 days.

(21) Appl. No.: 10/087,112

(22) Filed: Mar. 1, 2002

(65) Prior Publication Data

US 2002/0198224 A1 Dec. 26, 2002

Related U.S. Application Data

(60) Provisional application No. 60/272,434, filed on Mar. 1, 2001, and provisional application No. 60/272,441, filed on Mar. 1, 2001.

(51) Int. Cl.$^7$ ............................................. C07D 405/04
(52) U.S. Cl. ....................................................... 544/317
(58) Field of Search ......................................... 544/317

(56) References Cited

U.S. PATENT DOCUMENTS

| | | | |
|---|---|---|---|
| 3,817,982 A | 6/1974 | Verheyden et al. | |
| 4,594,339 A | 6/1986 | Lopez et al. | |
| 4,847,366 A | 7/1989 | Yamamoto et al. | |
| 4,900,828 A | 2/1990 | Belica et al. | |
| 4,904,770 A | 2/1990 | Starrett, Jr. et al. | |
| 4,987,224 A | 1/1991 | Chu | |
| 5,130,421 A | 7/1992 | Starrett, Jr. et al. | |
| 5,175,267 A | 12/1992 | Chu | |
| 5,200,514 A | 4/1993 | Chu | |
| 5,212,298 A | 5/1993 | Radamacher et al. | |
| 5,384,396 A | 1/1995 | Chu et al. | |
| 5,455,339 A | 10/1995 | Chu | |
| 5,539,099 A | 7/1996 | Skonezny et al. | |
| 5,561,120 A | 10/1996 | Lin et al. | |
| 5,625,057 A | 4/1997 | Shiragami et al. | |
| 5,703,058 A | 12/1997 | Schinazi et al. | |
| 5,905,070 A | 5/1999 | Schinazi et al. | |
| 6,232,300 B1 | 5/2001 | Schinazi et al. | |

FOREIGN PATENT DOCUMENTS

| | | |
|---|---|---|
| EP | 0 334 368 | 9/1989 |
| EP | 0 409 227 A2 | 7/1990 |
| NL | 8 901 258 | 12/1990 |
| WO | WO 96/22778 A1 | 8/1996 |
| WO | WO 99/43691 A1 | 9/1999 |

OTHER PUBLICATIONS

Abdel–Medied, A. W.–S., et al., *Synthesis*, 1991, 313.
Chen S., et al. "Synthesis and Biological Evaluation of a Series of 2'–Fluorinated–2',3'–Didehydro–(L)–Nucleosides." *Biorganic & Medicinal Chemistry Letters*. 8:3245–3250, 1998.
Chen, S., et al. "Stereoselective Synthesis of β–L–FD4C and β–L–FddC." *J. Org. Chem.* 62(11):3449–3452, 1997.
Cheng, Y., et al., *J. Med. Chem.* 1996, 62, 1757–1759.
Horwitz, J. P., et al. "Nucleosides. IX. The Formation of 2',3'–Unsaturated Pyrimidine Nucleosides via a Novel β–Elimination Reaction." *J. Org. Chem.* 31:205–211, Jan. 1966.
Horwitz, J. P., et al. "Nucleosides. VI. The Introduction of Unsaturation into the Carbohydrate of a Pyrimidine Nucleoside via a 2,3'–Anhydro Bond." *J. Am. Chem. Soc.* 86:1896–1897, May 5, 1964.
Horwitz, J. P., et al. "Nucleosides. XI. 2',3'–Dideoxycytidine." *J. Org. Chem.* 32:817–818, Mar. 1967.
Jain, T.C., et al. "Reactions of 2–Acyloxyisobutyryl Halides with Nucleosides. IV. A Facile Synthesis of 2',3'–Unsaturated Nucleosides Using Chromous Acetate." *J. Org. Chem.* 39(1):30–38, 1974.
Manchand et al. "Syntheses of the Anti–AIDS Drug 2',3'–Dideoxycytidine from Cytidine." *J. Org. Chem.* 57(12):3473–3478, 1992.
Morikawa, T., et al., *Chem. Pharm Bull.*, 1992, 40, 3189.
Patrick, T.B., et al. "New Fluorobutenolide Templates for Synthesis." *J. Org. Chem.* 59(5):1210–1212, 1994.
Robins, M. J., et al., *Tetrahedron Letters* 1984, 25, 367.
Russell, A. F., et al., *J. Am. Chem. Soc.* 1973, 95, 4025.
Shi, et al. "Synthesis and Biological Evaluation of 2',3'–Didehydro–2',3'–dideoxy–5–fluorocytidine (D4FC) Analogues: Discovery of Carbocyclic Nucleoside Triphosphates with Potent Inhibitory Activity against HIV–1 Reverse Transcriptase." *J. Med. Chem.* 42:859–867, 1999.

(Continued)

*Primary Examiner*—Thomas C. McKenzie
(74) *Attorney, Agent, or Firm*—Sherry M. Knowles, Esq.; King & Spalding, LLP

(57) ABSTRACT

An efficient synthetic route to antiviral 2',3'-dideoxy-2',3'-didehydro-nucleosides, such as 2',3'-dideoxy and 2'- or 3'-deoxyribo-nucleoside analogs, from available precursors is disclosed, with the option of introducing functionality as needed. In one embodiment, a method for the preparation of β-D and β-L-2',3'-dideoxy-2',3'-didehydro-nucleosides is described that includes: activating a compound of structure (1)

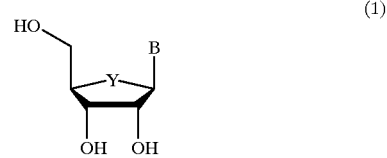

wherein B is a pyrimidine or purine base and Y is O, S or CH$_2$ with an acyl halide of the formula X—C(=O)R$^1$, X—C(=O)C(R$^1$)$_2$OC(=O)R$^1$ or X—C(=O)OR$^1$ (wherein X is a halogen, and each R$^1$ is independently hydrogen, lower alkyl, alkyl, aryl or phenyl); reducing the resulting compound with a reducing agent to form a 2',3'-dideoxy-2', 3'-didehydro-nucleoside; and optionally deprotecting the nucleoside. The haloacylation of the first step can form the 2'-acyl-3'-halonucleoside, the 3'-acyl-2'-halonucleoside, or a mixture thereof.

60 Claims, No Drawings

OTHER PUBLICATIONS

Sujino, K., et al. "Facile Synthesis of 2',3'–Unsaturated Nucleosides from 2–Deoxyribose." *Tetrahedron Letters.* 37(34):6133–6136, 1996.

Thenappan, A., et al. "Reduction–Olefination of Esters: A New and Efficient Synthesis of α,β–Unsaturated Esters." *J. Org. Chem.* 55(15):4639–4612, 1990.

Verheyden, J.P., et al "2',3'–Unsaturated nucleosides." *Chem. Abstr.* 81:508(63942), 1974.

Coe, et al.,*Journal of Flourine Chemistry, Elsevier Sequoia, Lausanne, CH*, vol. 69, No. 1, pp. 19–24, 1994.

Classon, B. et al., *ACTA Chem. Scand., Ser. B.* , B36(4), 251–3, 1982.

Mansuri, M M et al., *J. of Organic Chemistry, American Chemical Society*, vol. 54, No. 20, Sep. 29, 1989, 1780–4785.

Ozaki, S. et al.,*Bull. Chem. Soc. Jpn.*, 50(8), 2197–8, 1977.

Ozaki, S. et al., *Nucleic Acids Symp. Ser.*, 9–1, 12, p. 11, table 1, 1983.

Watanabe, K.A. et al., *J. Med. Chem*, 23(10), 1088–94, 1980.

Van Aerschot, A. et al., *j. MED Chem*, 33(6), 1833–9, 1990.

METHOD FOR THE SYNTHESIS OF 2',3'-DIDEOXY-2',3'-DIDEHYDRONUCLEOSIDES

This application claims priority to U.S. provisional application Nos. 60/272,434 and 60/272,441, both filed on Mar. 1, 2001.

FIELD OF THE INVENTION

This invention is a novel process for the synthesis of β-D and β-L-2',3'-didehydro-2',3'-dideoxy-nucleosides ("D4" nucleosides), and in particular β-D-2',3'-didehydro-2',3'-dideoxy-5-fluorocytidine (β-D-D4FC), useful as antiviral agents and chemotherapeutics.

BACKGROUND OF THE INVENTION

In 1981, acquired immune deficiency syndrome (AIDS) was identified as a disease that severely compromises the human immune system. In 1983, the etiological cause of AIDS was determined to be the human immunodeficiency virus (HIV). Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication.

A number of compounds are effective in the treatment of the human immunodeficiency virus (HIV) which is the retrovirus that causes progressive destruction of the human immune system with the resultant onset of AIDS. Effective treatment through inhibition of HIV reverse transcriptase is known for both nucleoside based inhibitors and non-nucleoside based inhibitors. Nucleoside based HIV inhibitors in the treatment of AIDS. In 1985, it was reported that the synthetic nucleoside 3'-azido-3'-deoxythymidine (AZT) inhibits the replication of human immunodeficiency virus. Since then, a number of other synthetic nucleosides, including 3'-azidoguanosine (AZG), 2',3'-dideoxycytidine (ddC), 2',3'-dideoxyadenosine (ddA), 3'-fluoro-3'-deoxythymidine (FDDT) and 2',3'-dideoxyinosine (ddI) have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

The success of various synthetic nucleosides in inhibiting the replication of HIV in vivo or in vitro has led a number of researchers to design and test nucleosides that substitute a heteroatom for the carbon atom at the 3'-position of the nucleoside. Norbeck, et al., disclosed that (±)-1-[(2β,4β)-2-(hydroxymethyl)-4-dioxolanyl]thymine (referred to as (±)-dioxolane-T) exhibits a modest activity against HIV (EC$_{50}$ of 20 μM in ATH8 cells), and is not toxic to uninfected control cells at a concentration of 200 μM. *Tetrahedron Letters* 30 (46), 6246, (1989). European Patent Application Publication No. 0 337 713 and U.S. Pat. No. 5,041,449, assigned to BioChem Pharma, Inc., disclose racemic 2-substituted-4-substituted-1,3-dioxolanes that exhibit antiviral activity.

U.S. Pat. No. 5,047,407 and European Patent Application Publication No. 0 382 526, also assigned to BioChem Pharma, Inc., disclose that a number of racemic 2-substituted-5-substituted-1,3-oxathiolane nucleosides have antiviral activity, and specifically report that the racemic mixture of 2-hydroxymethyl-5-(cytosin-1-yl)-1,3-oxathiolane (referred to below as BCH-189) has approximately the same activity against HIV as AZT, and little toxicity. BCH-189 has also been found to inhibit the replication of AZT-resistant HIV isolates in vitro from patients who have been treated with AZT for longer than 36 weeks. The (−)-enantiomer of the β-isomer of BCH-189, known as 3TC, which is highly potent against HIV and exhibits little toxicity, has been approved for the treatment of HIV in humans by the U.S. Food and Drug Administration in combination with AZT.

It has also been disclosed that cis-2-hydroxymethyl-5-(5-fluorocytosin-1-yl)-1,3-oxathiolane ("FTC") has potent HIV activity. Schinazi, et al., "Selective Inhibition of Human Immunodeficiency viruses by Racemates and Enantiomers of cis-5-Fluoro-1-[2-(Hydroxymethyl)-1,3-Oxathiolane-5-yl]Cytosine" *Antimicrobial Agents and Chemo-therapy*, November 1992, page 2423–2431. See also U.S. Pat. Nos. 5,210,085; 5,204,466, WO 91/11186, and WO 92/14743.

A number of 2',3'-dideoxy-2',3'-didehydro-nucleosides have been shown to have potent anti-HIV-1 activity. 2',3'-Dideoxy-2',3'-didehydro-thymidine ("D4T"; also referred to as 1-(2,3-dideoxy-β-D-glycero-pent-2-eno-furanosyl) thymine) is currently sold for the treatment of HIV under the name Stavudine by Bristol Myers Squibb. Other D4 nucleosides that have been tested include 2',3'-dideoxy-2',3'-didehydro-cytidine ("D4C"), 2',3'-dideoxy-2',3'-didehydro-uridine ("D4U"), 2',3'-dideoxy-2',3'-didehydro-adenosine ("D4A"), 2',3'-dideoxy-2',3'-didehydro-inosine ("D4I"), and 2',3'-dideoxy-2',3'-didehydro-guanosine ("D4G").

Other 2',3'-dideoxy-2',3'-didehydronucleosides have been reported to be effective against HIV and/or HBV. Starrett, Jr. et al., in U.S. Pat. Nos. 4,904,770, and 5,130,421, and Skonezny et al., in U.S. Pat. No. 5,539,099, disclose processes for the preparation of compounds of formula:

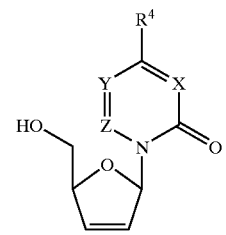

wherein X and Z are selected from N or CH;

Y is selected from CR$^2$ or N

R$^2$ is selected from H, unsubstituted and halo-substituted alkyl having formula C$_n$H$_{2n}$A and alkenyl having the formula (CH$_2$)$_m$—CH=CHA wherein m=0, 1, 2 or 3 and n is 1, 2 or 3; and A is H, F, Cl, Br and I; and R$^4$ is NH$_2$ or OH, useful as antiviral agents against HIV. Belica et al., in U.S. Pat. No. 4,900,828, disclose a process for the preparation of a compound of formula

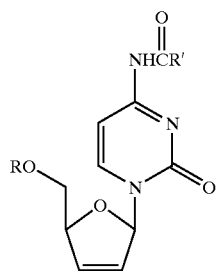

wherein R is a substituted or unsubstituted 2-acetoxy-2-methyl-propanoyl, 2-acetoxypropanoyl or 2-acetoxybenzoyl, optionally substituted with a lower alkyl, aryl or aralkyl;
$R^1$ is a substituted or unsubstituted lower alkyl, aryl, aralkyl optionally substituted with halogen, alkyl, nitro or alkoxy;
which is used to prepare 2',3'-dideoxynucleosides such as 2,3'-dideoxycytidine (ddC). See also Manchand P. S., *J. Org. Chem.*, 1992, 57, 3473.

In particular, β-D-2',3'-didehydro-2',3'-dideoxy-5-fluorocytidine or β-D-D4FC, having the structure

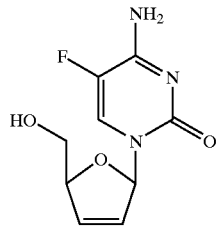

exhibits potent anti-HIV activity in vitro and demonstrates no cross-resistance with all approved anti-HIV agents. See Schinazi et al., *J. Med. Chem.* 1999, 42,859–867.

Also see Schinazi et al., in U.S. Pat. No. 5,703,058 which discloses a method and composition for compounds of formula

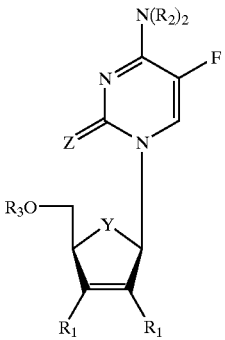

wherein Y is O, S, $CH_2$, CHF, $CF_2$;
Z is O, S or Se;
$R_1$ is H or F;
$R_2$ is H, OH, $C_1$–$C_6$ alkyl or $C(O)C_1$–$C_6$alkyl; and
$R_3$ is H, $C(O)C_1$–$C_6$alkyl, alkyl or mono-, di- or tri-phosphate;
for the treatment of HIV and HBV infections in humans and other host animals.

U.S. Pat. No. 6,232,300 and International Patent Application No. PCT/US96/00965, published as WO 96/22778 discloses a method for the treatment of HIV using β-D-D4FC. U.S. Pat. No. 5,703,058 discloses a method for the treatment of HIV and HBV infection that includes administering an effective amount of β-L-D4FC in combination or alternation with cis-2-hydroxymethyl-5-(5-fluorocytosin-1-yl)-1,3-oxathiolane, cis-2-hydroxymethyl-5-(cytosin-1-yl)-1,3-oxathiolane, 9-[4-(hydroxy-methyl)-2-cyclopenten-1-yl)-guanine (carbovir), 9-[(2-hydroxyethoxy)methyl] guanine (acyclovir), interferon, 3'-deoxy-3'-azido-thymidine (AZT), 2',3'-dideoxyinosine (DDI), 2',3'-dideoxycytidine (DDC), (−)-2'-fluoro-5-methyl-β-L-ara-uridine (L-FMAU) or 2',3'-didehydro-2',3'-dideoxythymidine (D4T). U.S. Pat. No. 5,905,070 discloses a method for the treatment of HIV and HBV infection that includes administering an effective amount of β-D-D4FC in combination or alternation with cis-2-hydroxymethyl-5-(5-fluorocytosin-1-yl)-1,3-oxathiolane, cis-2-hydroxymethyl-5-(cytosin-1-yl)-1,3-oxathiolane, 9-[4-(hydroxymethyl)-2-cyclopenten-1-yl)-guanine (carbovir), 9-[(2-hydroxyethoxy)methyl]guanine (acyclovir), interferon, 3'-deoxy-3'-azido-thymidine (AZT), 2',3'-dideoxyinosine (DDI), 2',3'-dideoxycytidine (DDC), (−)-2'-fluoro-5-methyl-β-L-ara-uridine (L-FMAU) or 2',3'-didehydro-2',3'-dideoxythymidine (D4T).

European Patent Application Publication No. 0 409 227 A2 filed by Ajinomoto Co., Inc., discloses β-D-D4FC (Example 2) and its use to treat hepatitis B. Netherlands Patent No. 8901258 filed by Stichting Rega V. Z. W. discloses generally 5-halogeno-2',3'-dideoxy-2',3'-didehydrocytidine derivatives for use in treating HIV and hepatitis B ("HBV").

Due to the importance of 2',3'-dideoxy-2',3'-didehydro-nucleosides, and in particular, β-D-2',3'-didehydro-2',3'-dideoxy-5-fluorocytidine ("β-D-D4FC"), as potent antihuman immunodeficiency virus agents, there is a need for a commercial or industrial scale process for the synthesis of 2',3'-dideoxy-2',3'-didehydro-nucleosides, and in particular, β-D-D4FC. On addition, natural and unnatural D4 nucleosides can serve as synthetic intermediates for the preparation of a large variety of other nucleoside analogs, including but not limited to 2',3'-dideoxy, and 2' or 3'-deoxyribo-nucleoside analogs as well as additional derivatives obtained by subsequent functional group manipulations. In view of the importance of 2',3'-dideoxy-2',3'-didehydro-nucleosides, it is desirable to have a facile, efficient and general route of synthesis of these compounds. While several methods exist for the synthesis of 2',3'-dideoxy-2',3'-didehydro-nucleosides, none has the ability to produce efficiently both enantiomeric forms of these compounds using purine bases, pyrimidine bases, heteroaromatics or heterocycles.

Several syntheses for the preparation of β-D-D4FC or its enantiomer, β-L-D4FC, have been reported. See Schinazi R. F. et al, *J. Med. Chem.* 1999, 42,859–867; Chen S., *Biorganic & Medicinal Chemistry Letters* 8(1998) 3245–3250; Doyle, T. W., et al., *J. Org. Chem.* 1997,62, 3449–3452; Cheng, Y., et al., *J. Med. Chem.* 1996, 62, 1757–1759; and Lin et al., U.S. Pat. No. 5,561,120.

One of the earliest syntheses of 2',3'-dideoxy-2',3'-didehydro-nucleosides is the published process for the preparation of 2',3'-dideoxy-2',3'-didehydro-thymidine (D4T). The first reported method to produce D4T involved the base promoted elimination of 3'-O-sulfonyl esters of- 2'-deoxynucleosides. This synthetic route is limited to pyrimidine nucleosides and cannot be used in the production of purine nucleosides. Horwitz, J. P., et al., *J. Org. Chem.* 1966, 31, 205; Horwitz, J. P., et al., *J. Org. Chem.* 1967, 32, 817; and Horwitz, J. P., et al., *J. Am. Chem. Soc.* 1964, 86, 1896.

Some 2',3'-dideoxy-2',3'-didehydro-nucleosides have been obtained directly from the corresponding ribonucleosides through their reaction with acetoxyisobutyryl 5 halides, followed by the reductive elimination of the 2',3'-acetoxy-2',3'-halogeno derivatives with chromous ion. U.S. Pat. No. 3,817,982 (1974); *Chem. Abstr.* 1974, 81, 63942; Russell, A. F., et al., *J. Am. Chem. Soc.* 1973, 95, 4025; Jain, T. C., et al., *J. Org. Chem.* 1974, 39, 30; Classon, B., et al., *Acta Chem. Scand. Sect B* 1982, 32, 251; Robins, M. J., et al., *Tetrahedron Letters* 1984, 25, 367. In a variation of this method, zinc in dimethylformamide can be used instead of chromous acetate. Robins, M. J., et al., *Tetrahedron Letters* 1984, 25, 367. The reaction is difficult, and results in several products, and is therefore an inefficient route to obtain the 2',3'-unsaturated compounds (Jain, T. C., et al., *J. Org. Chem.* 1974, 39, 30).

U.S. Pat. No. 5,455,339 to Chu describes a method for preparing 2',3'-dideoxy-2',3'-didehydro-nucleosides via dialkyl xanthate intermediates including:

(i) preparing a nucleoside derivative of the general structure:

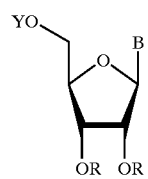

wherein B is a nitrogen, oxygen, or sulfur heterocycle of from $C_1$ to $C_{15}$, Y is a suitable oxygen protecting group, each R is C(S)SR', where $R^1$ is an alkyl or cyanoalkyl group of $C_1$ to $C_{15}$, or both R's together are >C=S;

(ii) activating the 2' and 3' hydroxyls to form 2',3'-thiocarbonates; and then (iii) deoxygenating the nucleoside derivative to the corresponding 2',3'-dieoxy-2',3'-didehydronucleoside.

U.S. Pat. Nos. 5,703,058; 5,905,070 and 6,232,300 and International Patent Application No. PCT/US96/00965, published as WO 96/22778 to Raymond F. Schinazi and Dennis C. Liotta describes [5-carboxamido or 5-fluoro]-2',3'-dideoxy-2',3'-didehydro-pyrimidine nucleosides and [5-carboxamido or 5-fluoro]-3'-modified-pyrimidine nucleosides. Example 3 of the '070 patent provides a process for the preparation of 2',3'-dideoxy-2',3'-didehydro-nucleosides. The patent states that the procedure can be adapted for a wide variety of bases and can be used to provide either the β-D or the β-L isomer as desired. The process is illustrated below:

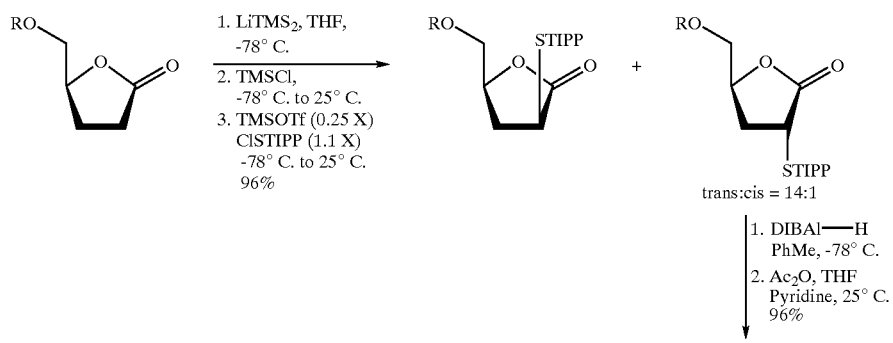

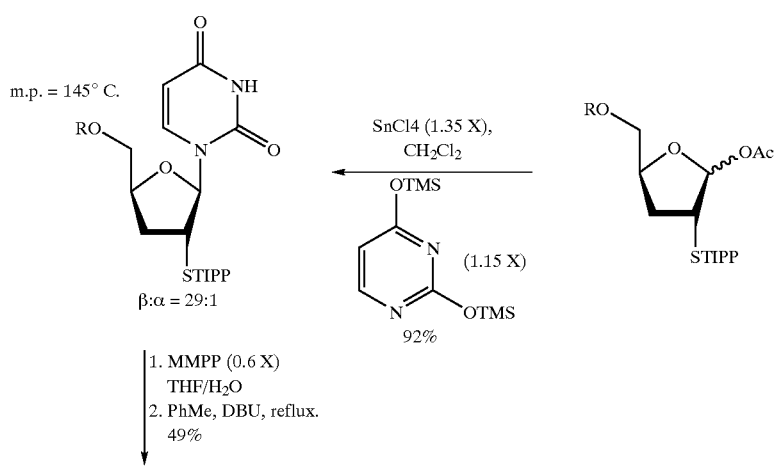

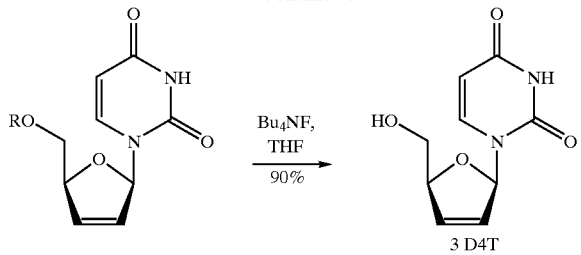

wherein MMPP is magnesium monoperoxyphthalate, R is t-butyldiphenylsilyl, and STIPP is 2,4,6-triisopropylphenyl.

PCT WO 99/43691 describes 2'-fluoro-2',3'-dideoxy-2', 3'-didehydronucleosides that are useful in the treatment of viral infections. Schemes 9, 10, and 11 of the PCT describe methods for the preparation of β-L-2'-fluoro-2',3'-didehydro-2',3'-dideoxy-nucleosides. The PCT publication states that previously, the synthesis of 2',3'-unsaturated L-nucleosides had been accomplished via an elimination reaction starting from readily available nucleoside analogs, which involved a lengthy modification procedure. There are few examples of the synthesis of 2',3'-unsaturated purine nucleosides by direct condensation due to the lability of the 2',3'-unsaturated sugar moiety under the coupling conditions in the presence of a Lewis acid, except one case of the pyrimidine analog using a thiophenyl intermediate (Abdel-Medied, A. W.-S., et al., Synthesis, 1991, 313; Sujino, K., et al., Tetrahedron Lett., 1996, 37, 6133). In contrast to the 2',3'-unsaturated sugar moiety, the 2'-fluoro-2',3'-unsaturated sugar, which bears enhanced stability of the glycosyl bond during the condensation with a heterocycle, is more suitable for the direct coupling reaction. As illustrated below (wherein B is a purine or pyrimidine base and R is an oxygen protecting group), (R)-2'-fluorobutenolide (prepared from L-glyceraldehyde acetonide) was used as the key precursor in the preparation of 2'-fluoro-2',3'-dideoxy-2',3'-didehydronucleosides. From the acetonide, a mixture of E and Z isomers was obtained via the Homer-Emmons reaction in the presence of triethyl α-fluorophosphonoacetate and sodium bis(trimethylsilyl)amide in THF (Thenappan, A., et al., J. Org. Chem., 1990, 55, 4639; Morikawa, T., et al., Chem. Pharm. Bull., 1992, 40, 3189; Patrich, T. B., et al., J. Org. Chem., 1994, 59, 1210). Due to the difficulties in separating the E and Z isomers, the mixture was carried on to the cyclization reaction under acidic conditions to give the desired lactone and uncyclized diol. The resulting mixture was converted to the silyl lactone and was subjected to reduction with DIBA1-H in $CH_2Cl_2$ at 78° C. to give the lactol. The lactol was treated with acetic anhydride to yield a key acetate intermediate, which was condensed with silylated 6-chloropurine under Vorbruggen conditions to afford anomeric mixtures of the protected nucleoside. Treatment of the protected nucleoside with TBAF in THF gave a mixture of free nucleosides that could be separated by silica gel column chromatography. The adenine analogs are obtained by the treatment of 6-chloropuridine with mercapto-ethanol and NaOMe in a steel bomb at 90° C. Further treatment of the adenine analogs under the same conditions afforded the inosine analogs.

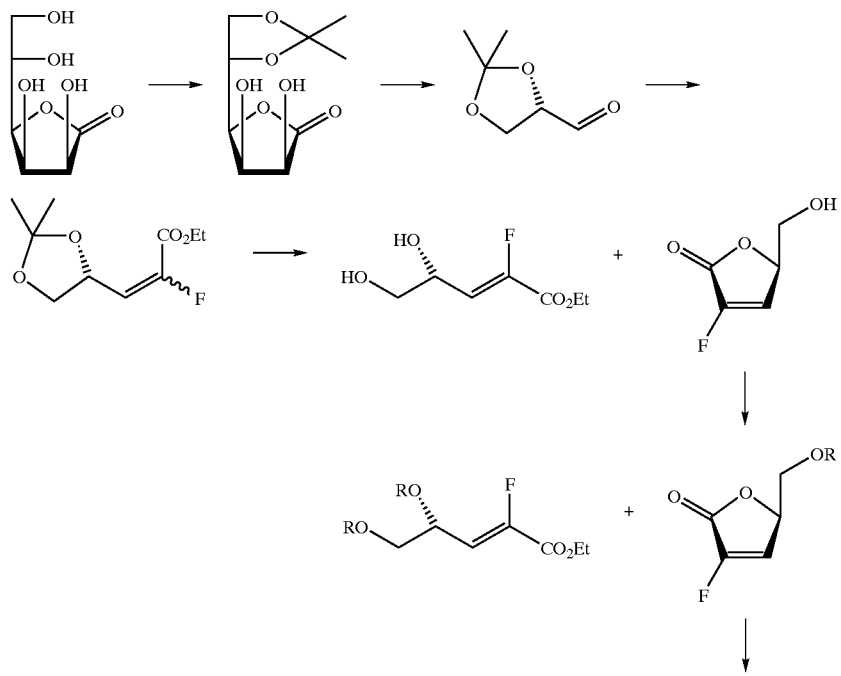

-continued

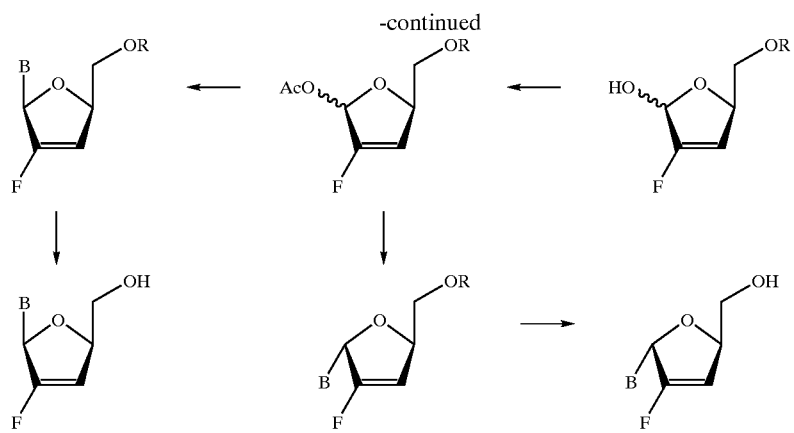

The above methods for the syntheses of β-D-2',3'-didehydro-2',3'-dideoxy-5-fluorocytidine, or its enantiomer, β-L-D4FC, disclose synthetic routes employing combinations of toxic and/or difficult to handle reagents, linear or sequential reaction steps, and laborious chromatographic or purification steps. Consequently, these syntheses afford an inefficient synthesis of β-D-D4FC.

Therefore, it is another object of the present invention to provide a process for the production of 2',3'-dideoxy-2',3'-didehydro-nucleosides that is facile and efficient.

It is an object of the present invention to provide a high yield method to manufacture 2',3'-didehydro-2',3'-dideoxynucleosides, and in particular p-D-2',3'-didehydro-2',3'-dideoxy-5-fluorocytidine.

It is an object of the present invention to provide a method to manufacture 2',3'-didehydro-2',3'-dideoxynucleosides, and in particular β-D-2',3'-didehydro-2',3'-dideoxy-5-fluorocytidine, which produces few undesired side products.

It is another object of the present invention to provide a method to manufacture 2',3'-didehydro-2',3'-dideoxynucleosides, and in particular β-D-2',3'-didehydro-2',3'-dideoxy-5-fluorocytidine, which is amenable to commercial production.

It is a particular object of the present invention to provide a method to manufacture 2',3'-didehydro-2',3'-dideoxynucleosides, and in particular β-D-2',3'-didehydro-2',3'-dideoxy-5-fluorocytidine, which does not require protection of the purine or pyrimidine base, such as cytosine or 5-fluorocytosine.

It is a particular object of the present invention to provide a method to manufacture 2',3'-didehydro-2',3'-dideoxynucleosides, and in particular β-D-2',3'-didehydro-2',3'-dideoxy-5-fluorocytidine, which does not require purification by chromatography.

It is a particular object of the present invention to provide a method to manufacture 2',3'-didehydro-2',3'-dideoxynucleosides, and in particular p-D-2',3'-didehydro-2',3'-dideoxy-5-fluorocytidine, which does not require the use of toxic metals.

It is a further object of the present invention to provide a process for the production of 2',3'-dideoxy-2',3'-didehydro-nucleosides that can be used as synthetic intermediates for the preparation of a large variety of other nucleoside analogs, including but not limited to 2',3'-dideoxy, and 2' and 3'-deoxyribo nucleoside analogs as well as additional derivatives obtained by subsequent functional group manipulations.

SUMMARY OF THE INVENTION

The present invention is an efficient synthetic route to 2',3'-dideoxy-2',3'-didehydro-nucleosides from available precursors with the option of introducing functionality as needed. The present invention provides an efficient commercial process of high yields, can be conducted on a gram, multigram, kilogram, or multikilogram scale, and yields stable intermediates. The invention further provides for a nonchromato-graphic separation to improve overall yield. In addition, the D4 compounds made according to the present invention can also be used as synthetic intermediates in the preparation of a variety of other nucleoside analogs, including but not limited to 2',3'-dideoxy and 2'- or 3'-deoxyribo-nucleoside analogs as well as additional derivatives obtained by subsequent functional group manipulations.

Briefly, the present invention discloses a method for the preparation of β-D and β-L-2',3'-dideoxy-2',3'-didehydro-nucleosides starting from appropriately substituted ribo-nucleosides in two, optionally three steps: Step (1) a haloacylation, such as haloacetylation, and in particular, bromoacetylation; Step (2) a reductive elimination; and optionally, Step (3) a deprotection. The haloacylation of step (1) can form the 2'-acyl-3'-halonucleoside, the 3'-acyl-2'-halonucleoside, or a mixture thereof.

The method for preparing β-D- and β-L-2',3'-dideoxy-2',3'-didehydro-nucleosides is provided, comprising:

a) activating a compound of structure (1)

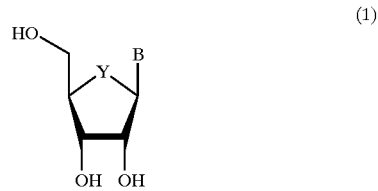

wherein B is a pyrimidine or purine base, including but not limited to, 5-fluorocytosine, 5-fluorouracil, cytosine, uracil, thymine, adenine, guanine, or inosine, and even more preferably 5-fluorocytosine or 5-fluorouracil; and Y is O, S or $CH_2$;

with an acyl halide of the formula $X—C(=O)R^1$, $X—C(=O)C(R^1)_2OC(=O)R^1$ or $X—C(=O)phenylC(=O)OR^1$;

wherein X is a halogen (F, Cl, Br or I), and each $R^1$ is independently hydrogen, lower alkyl, alkyl, aryl or phenyl;

to form a compound of structure (2)

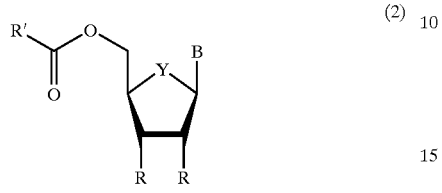

(2)

wherein R is R', $—C(R^1)_2OC(=O)R^1$ or $-phenylC(=O)OR^1$; and at least one R is halogen (F, Cl, Br or I), and at least one R is an acyl of the formula $—OC(=O)R^1$; and then b) reducing the compound of structure (2) with a reducing agent to form a 2',3'-dideoxy-2',3'-didehydro-nucleoside of structure (3)

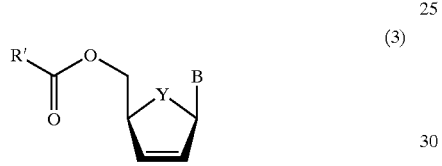

(3)

c) optionally deprotecting the nucleoside if necessary.

In one embodiment of the invention, the nucleoside of structure (3) is optionally further derivatized, for example by base modification or sugar modification by methods known in the art; and then optionally deprotecting the nucleoside if necessary.

In one embodiment, the β-D or β-L-2',3'-dideoxy-2',3'-didehydro-nucleoside can be converted into a β-D or β-L-2',3'-dideoxy-2',3'-didehydro-nucleoside bearing a different nucleobase. For example, a β-D or β-L-2',3'-dideoxy-2',3'-didehydro-5-fluorouridine can be derivatized to form a β-D or β-L-2',3'-dideoxy-2',3'-didehydro-5-fluorocytidine. Similarly a β-D or β-L-2',3'-dideoxy-2',3'-didehydro-uridine can be further derivatized to form β-D or β-L-2',3'-dideoxy-2',3'-didehydro-cytidine. Alternatively, the β-D or β-L-2',3'-dideoxy-2',3'-didehydro-nucleoside can be reduced to form a β-D or β-L-2',3'-dideoxy and 2'- or 3'-deoxyribo-nucleoside analog. For example, hydrogen reduction can be effected in ethanol with 10% palladium on carbon. Alternatively, the D4 nucleoside can be modified to form a 2', a 3' or a 5'-substituted-nucleoside or a combination thereof, also using known chemistry to those skilled in the art. As a non-limiting illustrative example, Townsend, et al., *Chemistry of Nucleosides and Nucleotides, Volume* 1, Plenum Press: New York, teaches oxidation of 2'3'-dideoxy-2'3'-didehydro-nucleosides with osmium tetraoxide yields a ribonucleoside. Further functionalities can be introduced via the 2' or 3' hydroxyls using the teachings of Kuzuhara, H., et al., U.S. Pat. No. 5,144,018 (1992) by activating and substituting the relevant hydroxyl.

In one particular embodiment, the present invention provides for a novel, short, and high yield three step β-D-D4FC synthesis that produces few undesired side-products.

The synthesis of the present invention does not require protection of the 5-fluorocytosine, purification by chromatography or use of toxic metals. Thus the process of the present invention is feasible to run on a gram, kilogram or multi-kilogram commercial scale.

In one illustrative embodiment of the invention, a process for the preparation of a compound of Formula (IV) is provided,

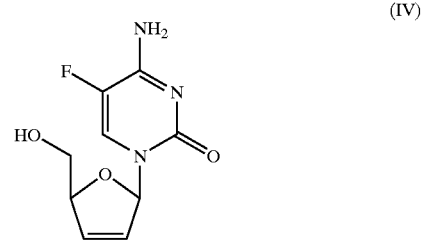

(IV)

comprising:

(1) contacting a compound of Formula (I)

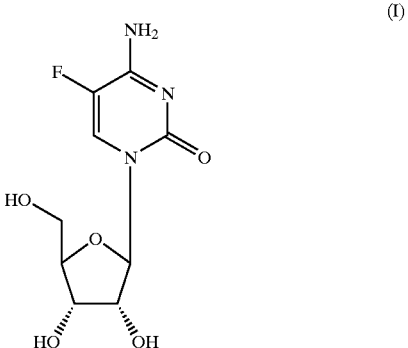

(I)

with an acyl halide of Formula $Q—C(=O)X$, wherein:

Q is $2-(R^1CH_2CO_2)phenyl-$, $R^1CH_2—$, or $R^1CH_2C(=O)OC(R^2)_2—$;

X is Cl, Br or I;

$R^1$ is H or $C_1$–$C_6$ alkyl ($C_1$, $C_2$, $C_3$, $C_4$, $C_5$ or $C_6$ alkyl);

$R^2$, at each occurrence, is independently selected from alkyl, preferably a lower alkyl, such as methyl, ethyl or propyl;

in a suitable polar aprotic solvent to form a compound of Formula (II) or (II*), or compounds of Formula (II) and (II*):

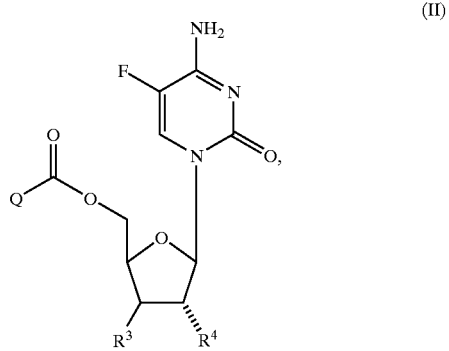

(II)

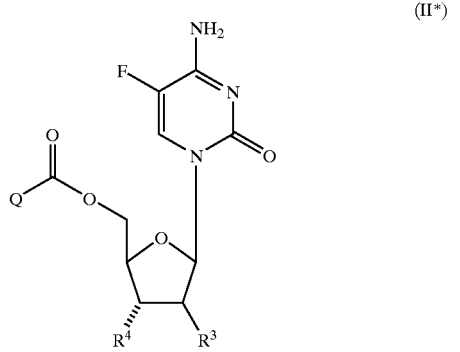

(II*)

wherein $R^3$ is X; and $R^4$ is —OC(=O)CH$_2$R$^1$;

(2) contacting a compound of Formula (II) or (II*), or compounds of Formula (II) and (II*), with a suitable reducing agent in a suitable polar solvent, optionally in the presence of a suitable acid catalyst, to form a compound of Formula (III),

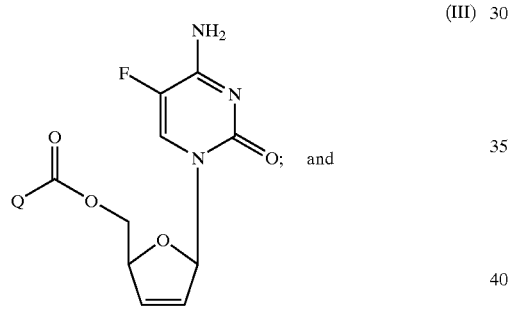

(III)

(3) contacting a compound of Formula (III) with a suitable base to form a compound of Formula (IV).

Therefore, the present invention discloses a method for the preparation of β-D-D4FC starting from 5-fluorocytidine in two, optionally three steps: Step (1) a haloacylation, such as haloacetylation, and in particular, bromoacetylation; Step (2) a reductive elimination; and optionally, Step (3) a deprotection. The haloacylation of step (1) can form the 2'-acyl-3'-halonucleoside, the 3'-acyl-2'-halonucleoside, or a mixture thereof. The method of the present invention does not require protection of the primary amine group of the cytidine. Literature precedent suggests that protection of the primary amine group of a cytidine is required for a clean and high yield reaction. See Manchand et al., *J. Org. Chem.* 1992, 57, 3473. The use of a combination of polar aprotic solvents in Step (1) improves the impurities profile, allows for modification of reaction rates, and/or facilitates the handling of the intermediate product(s).

Alternatively, in another illustrative embodiment, the present invention discloses a method for the preparation of a compound of Formula (IV):

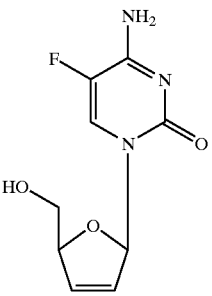

(IV)

comprising:

(1) contacting a compound of Formula (V):

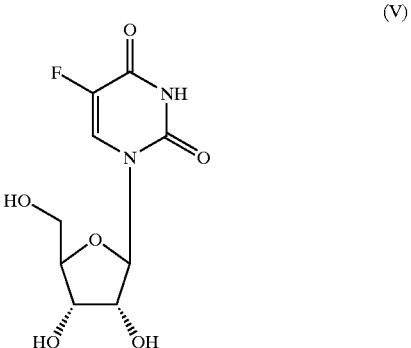

(V)

with an acyl halide of Formula Q—C(=O)X, wherein:

Q is 2-(R$^1$CH$_2$CO$_2$)phenyl-, R$^1$CH$_2$—, or R CH$_2$C(=O)OC(R$^1$)$_2$—;

X is Cl, Br, or I;

R$^1$ is H or C$_1$–C$_6$ alkyl (C$_1$, C$_2$, C$_3$, C$_4$, C$_5$ or C$_6$ alkyl);

R$^2$, at each occurrence, is independently selected from alkyl, preferably a lower alkyl, such as methyl, ethyl or propyl;

in a suitable polar aprotic solvent to form a compound of Formula (VI), a compound of Formula (VI*), or a mixture of compounds of Formula (VI) and (VI*):

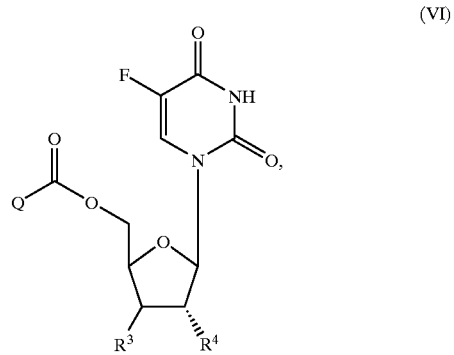

(VI)

-continued

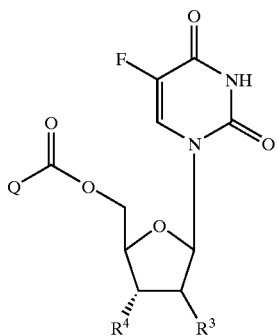
(VI*)

wherein R³ is X; and R⁴ is R¹CH₂C(=O)O—;

(2) contacting the compound of Formula (VI), the compound of Formula (VI*), or the mixture of compounds of Formula (VI) and (VI*); with a reducing agent in a suitable polar solvent, optionally in the presence of an acid catalyst, to form a compound of Formula (III):

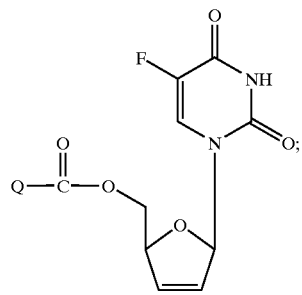
(VII)

(3a) contacting the compound of Formula (VII) with an activating agent in the presence of an amine base, to form a compound of Formula (VIII):

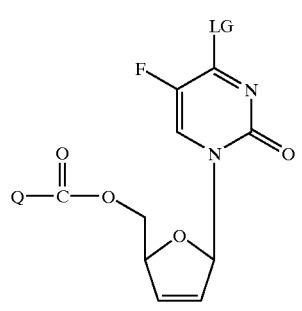
(VIII)

wherein LG is a leaving group derived from the activating agent;

(3b) contacting the compound of Formula (VIII) with an aminating agent to form a compound of Formula (III),

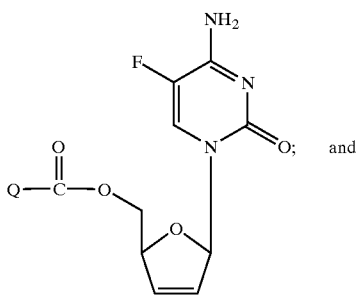
(III)

(4) contacting the compound of Formula (III) with a suitable base to form the compound of Formula (IV).

Therefore, the present invention discloses a method for the preparation of β-D-D4FC starting from 5-fluorouridine: Step (1) a haloacylation, such as haloacetylation, and in particular, bromoacetylation; Step (2) a reductive elimination; Step (3-a, b) a cytidine formation; and Step (3-c) a deprotection. The haloacylation of step (1) can form the 2'-acyl-3'-halonucleoside, the 3'-acyl-2'-halonucleoside, or a mixture thereof.

The procedures of the invention allow for streamlined processing since the intermediates after each step can be used directly in the subsequent reactions without having to be isolated or purified. For example, in the manufacture of β-D-D4FC from 5-fluorocytidine, Step (1) is optionally carried forward into Step (2) as a solution in a suitable aprotic solvent. Similarly the product(s) of Step (2) is optionally carried forward into Step (3) as a solution in a suitable solvent. The conditions used in Step (3), a catalytic amount of base in a suitable solvent, allow for a simple isolation of the final product β-D-D4FC. The use of a catalytic amount of the base facilitates isolation of the product since the base can be soluble in the suitable solvent used for Step (3). The product β-D-D4FC precipitates and/or crystallizes out of the solution upon removal of the suitable solvent. A second (re)crystallization can be performed to improve the purity of β-D-D4FC.

Alternatively, in the manufacture of β-D-D4FC from 5-fluorocytidine, Step (1) is optionally carried forward into Step (2) as a solution in a suitable aprotic solvent. Similarly the product(s) of Step (2) and (3-a, b) are optionally carried forward into Step (3-c) as a solution in a suitable solvent. The conditions used in Step (3-c), a catalytic amount of base in a suitable solvent, allow for a simple isolation of the final product β-D-D4FC. The use of a catalytic amount of the base facilitates isolation of the product since the base can be soluble in the suitable solvent used for Step (3-c). The product β-D-D4FC precipitates and/or crystallizes out of the solution upon removal of the suitable solvent. A second (re)crystallization can be performed to improve the purity of β-D-D4FC.

DETAILED DESCRIPTION OF THE INVENTION

The present invention is an efficient synthetic route to 2',3'-dideoxy-2',3'-didehydro-nucleosides from available precursors with the option of introducing functionality as needed. The present invention provides an efficient commercial process of high yields, can be conducted on a gram, multigram, kilogram, or multikilogram scale, and yields stable intermediates. The invention further provides for a nonchromato-graphic separation to improve overall yield. In addition, the D4 compounds made according to the present invention can also be used as synthetic intermediates in the preparation of a variety of other nucleoside analogs, including but not limited to 2',3'-dideoxy and 2'- or 3'-deoxyribonucleoside analogs as well as additional derivatives obtained by subsequent functional group manipulations.

Briefly, the present invention discloses a method for the preparation of α-D and β-L-2',3'-dideoxy-2',3'-didehydro-nucleosides starting from appropriately substituted ribonucleosides in two, optionally three steps: Step (1) a haloacylation, such as haloacetylation, and in particular, bromoacetylation; Step (2) a reductive elimination; and optionally, Step (3) a deprotection. The haloacylation of step (1) can form the 2'-acyl-3'-halonucleoside, the 3'-acyl-2'-halonucleoside, or a mixture thereof.

The method for preparing β-D- and β-L-2',3'-dideoxy-2',3'-didehydro-nucleosides is provided, comprising:

a) activating a compound of structure (1)

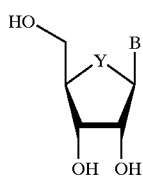

(1)

wherein B is a pyrimidine or purine base, including but not limited to, 5-fluorocytosine, 5-fluorouracil, cytosine, uracil, thymine, adenine, guanine, or inosine, and even more preferably 5-fluorocytosine or 5-fluorouracil; and Y is O, S or $CH_2$;

with an acyl halide of the formula $X-C(=O)R^1$, $X-C(=O)C(R^1)_2OC(=O)R^1$ or $X-C(=O)$ phenyl$C(=O)OR^1$;

wherein X is a halogen (F, Cl, Br or I), and each $R^1$ is independently hydrogen, lower alkyl, alkyl, aryl or phenyl;

to form a compound of structure (2)

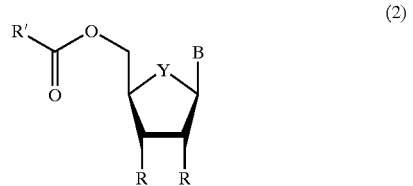

(2)

wherein R is $R^1$, $-C(R^1)_2OC(=O)R^1$ or -phenyl$C(=O)OR^1$; and at least one R is halogen (F, Cl, Br or I), and at least one R is an acyl of the formula $-OC(=O)R^1$; and then b) reducing the compound of structure (2) with a reducing agent to form a 2',3'-dideoxy-2',3'-didehydro-nucleoside of structure (3)

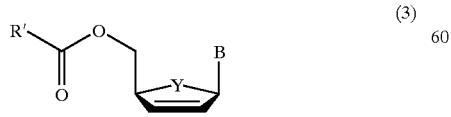

(3)

c) optionally deprotecting the nucleoside if necessary.

In one embodiment of the invention, the nucleoside of structure (3) is optionally further derivatized, for example by base modification or sugar modification by methods known in the art; and then optionally deprotecting the nucleoside if necessary.

In one embodiment, the β-D or β-L-2',3'-dideoxy-2',3'-didehydro-nucleoside can be converted into a β-D or β-L-2',3'-dideoxy-2',3'-didehydro-nucleoside bearing a different nucleobase. For example, a β-D or β-L-2',3'-dideoxy-2',3'-didehydro-5-fluorouridine can be derivatized to form a β-D or β-L-2',3'-dideoxy-2',3'-didehydro-5-fluorocytidine. Similarly a β-D or β-L-2',3'-dideoxy-2',3'-didehydro-uridine can be further derivatized to form a β-D or β-L-2',3'-dideoxy-2',3'-didehydro-cytidine. Alternatively, the β-D or β-L-2',3'-dideoxy-2',3'-didehydro-nucleoside can be reduced to form a β-D or β-L-2',3'-dideoxy and 2'- or 3'-deoxyribonucleoside analog. For example, hydrogen reduction can be effected in ethanol with 10% palladium on carbon. Alternatively, the D4 nucleoside can be modified to form a 2', a 3' or a 5'-substituted-nucleoside or a combination thereof, also using known chemistry to those skilled in the art. As a non-limiting illustrative example, Townsend, et al., *Chemistry of Nucleosides and Nucleotides, Volume 1*, Plenum Press: New York, teaches oxidation of 2'3'-dideoxy-2'3'-didehydro-nucleosides with osmium tetraoxide yields a ribonucleoside. Further functionalities can be introduced via the 2' or 3' hydroxyls using the teachings of Kuzuhara, H., et al., U.S. Pat. No. 5,144,018 (1992) by activating and substituting the relevant hydroxyl.

In one particular embodiment, the present invention provides for a novel, short, and high yield three step β-D-D4FC synthesis that produces few undesired side-products.

The synthesis of the present invention does not require protection of the 5-fluorocytosine, purification by chromatography or use of toxic metals. Thus the process of the present invention is feasible to run on a gram, kilogram or multi-kilogram commercial scale.

In one illustrative embodiment of the invention, a process for the preparation of a compound of Formula (IV) is provided,

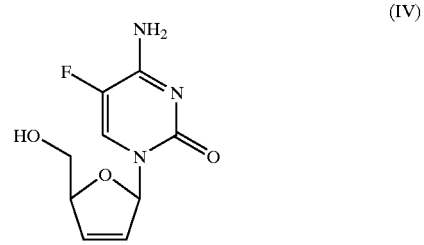

(IV)

comprising:

(1) contacting a compound of Formula (I)

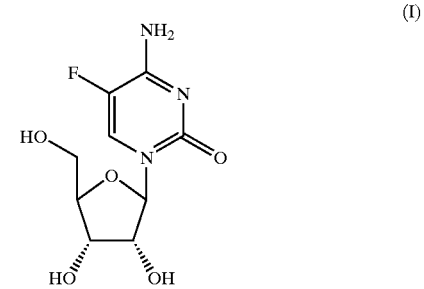

(I)

with an acyl halide of Formula $Q-C(=O)X$, wherein:

Q is 2-($R^1CH_2CO_2$)phenyl-, $R^1CH_2-$, or $R^1CH_2C(=O)OC(R^2)_2-$;

X is Cl, Br or I;

$R^1$ is H or $C_1$–$C_6$ alkyl ($C_1$, $C_2$, $C_3$, $C_4$, $C_5$ or $C_6$ alkyl);

$R^2$, at each occurrence, is independently selected from alkyl, preferably a lower alkyl, such as methyl, ethyl or propyl;

in a suitable polar aprotic solvent to form a compound of Formula (II) or (II*), or compounds of Formula (II) and (II*):

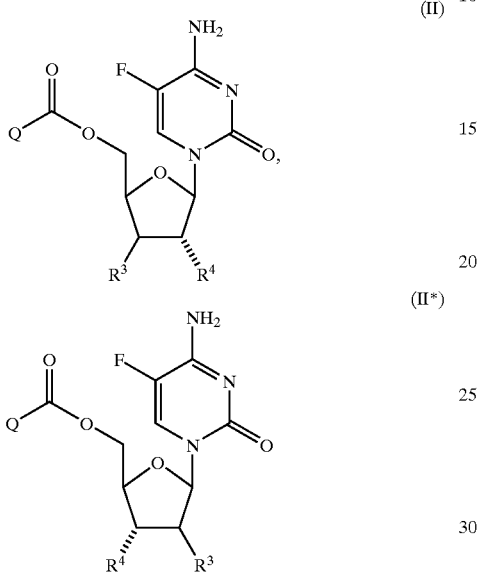

wherein $R^3$ is X; and
$R^4$ is —OC(=O)CH$_2$R$^1$;

(2) contacting a compound of Formula (II) or (II*), or compounds of Formula (II) and (II*), with a suitable reducing agent in a suitable polar solvent, optionally in the presence of a suitable acid catalyst, to form a compound of Formula (III),

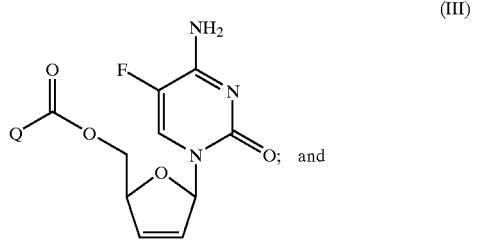

(3) contacting a compound of Formula (III) with a suitable base to form a compound of Formula (IV).

Therefore, the present invention discloses a method for the preparation of β-D-D4FC starting from 5-fluorocytidine in two, optionally three steps: Step (1) a haloacylation, such as haloacetylation, and in particular, bromoacetylation; Step (2) a reductive elimination; and optionally, Step (3) a deprotection. The haloacylation of step (1) can form the 2'-acyl-3'-halonucleoside, the 3'-acyl-2'-halonucleoside, or a mixture thereof. The method of the present invention does not require protection of the primary amine group of the cytidine. Literature precedent suggests that protection of the primary amine group of a cytidine is required for a clean and high yield reaction. See Manchand et al., *J. Org. Chem.* 1992, 57, 3473. The use of a combination of polar aprotic solvents in Step (1) improves the impurities profile, allows for modification of reaction rates, and/or facilitates the handling of the intermediate product(s).

Alternatively, in another illustrative embodiment, the present invention discloses a method for the preparation of a compound of Formula (IV):

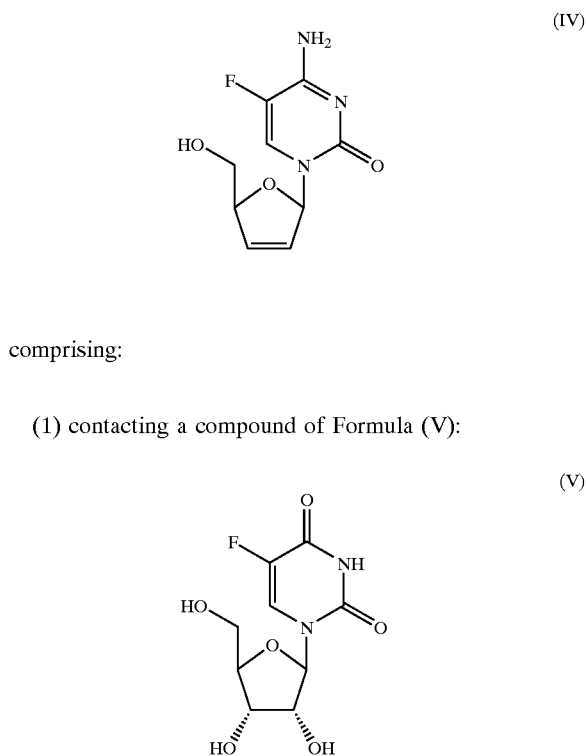

comprising:

(1) contacting a compound of Formula (V):

with an acyl halide of Formula Q—C(=O)X, wherein:

Q is 2-($R^1CH_2CO_2$)phenyl-, $R^1CH_2$—, or $R^1CH_2C(=O)OC(R^2)_2$—;

X is Cl, Br, or I;

$R^1$ is H or $C_1$–$C_6$ alkyl ($C_1$, $C_2$, $C_3$, $C_4$, $C_5$ or $C_6$ alkyl);

$R^2$, at each occurrence, is independently selected from alkyl, preferably a lower alkyl, such as methyl, ethyl or propyl;

in a suitable polar aprotic solvent to form a compound of Formula (VI), a compound of Formula (VI*), or a mixture of compounds of Formula (VI) and (VI*):

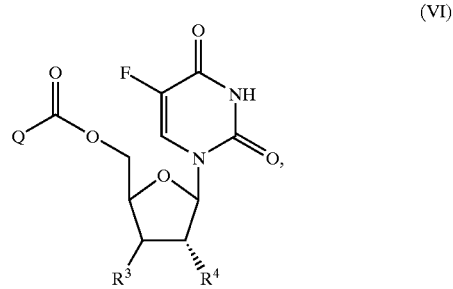

-continued

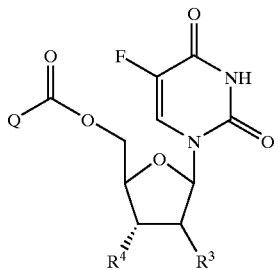

(VI*)

wherein R³ is X; and R⁴ is R¹CH₂C(=O)O—;

(2) contacting the compound of Formula (VI), the compound of Formula (VI*), or the mixture of compounds of Formula (VI) and (VI*); with a reducing agent in a suitable polar solvent, optionally in the presence of an acid catalyst, to form a compound of Formula (III):

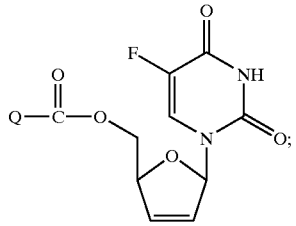

(VII)

(3a) contacting the compound of Formula (VII) with an activating agent in the presence of an amine base, to form a compound of Formula (VIII):

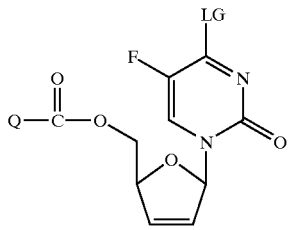

(VIII)

wherein LG is a leaving group derived from the activating agent;

(3b) contacting the compound of Formula (VIII) with an aminating agent to form a compound of Formula (III),

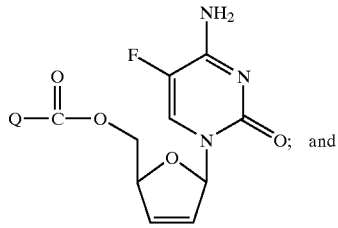

(III)

(4) contacting the compound of Formula (III) with a suitable base to form the compound of Formula (IV).

Therefore, the present invention discloses a method for the preparation of β-D-D4FC starting from 5-fluorouridine: Step (1) a haloacylation, such as haloacetylation, and in particular, bromoacetylation; Step (2) a reductive elimination; Step (3-a, b) a cytidine formation; and Step (3-c) a deprotection. The haloacylation of step (1) can form the 2'-acyl-3'-halonucleoside, the 3'-acyl-2'-halonucleoside, or a mixture thereof.

The procedures of the invention allow for streamlined processing since the intermediates after each step can be used directly in the subsequent reactions without having to be isolated or purified. For example, in the manufacture of β-D-D4FC from 5-fluorocytidine, Step (1) is optionally carried forward into Step (2) as a solution in a suitable aprotic solvent. Similarly the product(s) of Step (2) is optionally carried forward into Step (3) as a solution in a suitable solvent. The conditions used in Step (3), a catalytic amount of base in a suitable solvent, allow for a simple isolation of the final product β-D-D4FC. The use of a catalytic amount of the base facilitates isolation of the product since the base can be soluble in the suitable solvent used for Step (3). The product β-D-D4FC precipitates and/or crystallizes out of the solution upon removal of the suitable solvent. A second (re)crystallization can be performed to improve the purity of β-D-D4FC.

Alternatively, in the manufacture of β-D-D4FC from 5-fluorocytidine, Step (1) is optionally carried forward into Step (2) as a solution in a suitable aprotic solvent. Similarly the product(s) of Step (2) and (3-a, b) are optionally carried forward into Step (3-c) as a solution in a suitable solvent. The conditions used in Step (3-c), a catalytic amount of base in a suitable solvent, allow for a simple isolation of the final product β-D-D4FC. The use of a catalytic amount of the base facilitates isolation of the product since the base can be soluble in the suitable solvent used for Step (3-c). The product β-D-D4FC precipitates and/or crystallizes out of the solution upon removal of the suitable solvent. A second (re)crystallization can be performed to improve the purity of β-D-D4FC.

In a first principle embodiment, the present invention provides for a process for the preparation of a compound of Formula (IV):

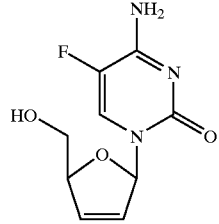

(IV)

comprising:
(1) contacting a compound of Formula (I):

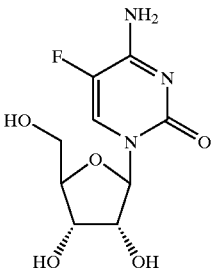

(I)

with an acyl halide of Formula Q—C(=O)X, wherein:

Q is 2-($R^1CH_2CO_2$)phenyl-, $R^1CH_2$—, or $R^1CH_2C(=O)OC(R^2)_2$—;

X is Cl, Br, or I;

$R^1$ is H or $C_1$–$C_6$ alkyl;

$R^2$, at each occurrence, is independently selected from methyl, ethyl and propyl;

in a suitable polar aprotic solvent to form a compound of Formula (II), a compound of Formula (II*), or a mixture of compounds of Formula (II) and (II*):

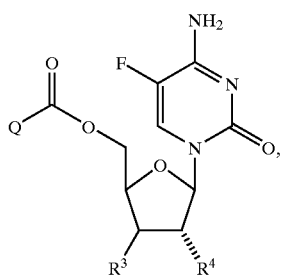
(II)

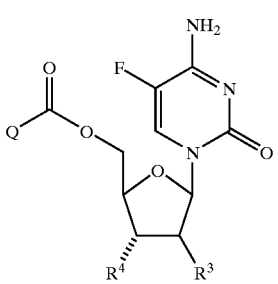
(II*)

wherein $R^3$ is X; and $R^4$ is $R^1CH_2C(=O)O$—;

(2) contacting the compound of Formula (II), the compound of Formula (II*), or the mixture of compounds of Formula (II) and (II*); with a suitable reducing agent in a suitable polar solvent, optionally in the presence of a suitable acid catalyst, to form a compound of Formula (III):

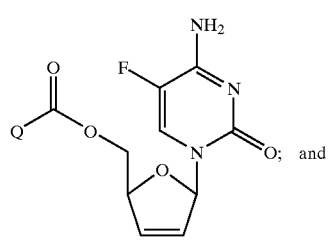
(III); and (3) contacting the compound of Formula (III) with a suitable base to form the compound of Formula (IV).

In a second principle embodiment the present invention provides for a process for the preparation of a compound of Formula (IV):

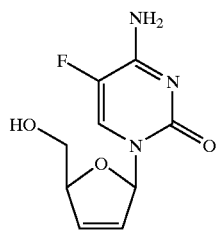
(IV)

comprising:

(1) contacting a compound of Formula (I):

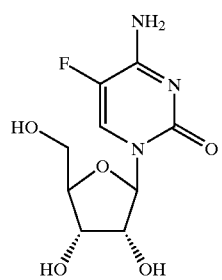
(I)

with an acyl halide of Formula Q—C(=O)X, wherein:

Q is $R^1CH_2C(=O)OC(R^1)_2$—;

X is Cl, Br or I;

$R^1$ is H, $CH_3$, $CH_2CH_3$, or $CH_2CH_2CH_3$;

$R^2$, at each occurrence, is independently selected from methyl, ethyl and propyl;

in a suitable polar aprotic solvent to form a compound of Formula (II) or a compound of Formula (II*):

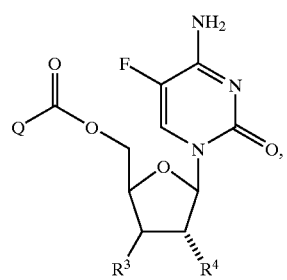
(II)

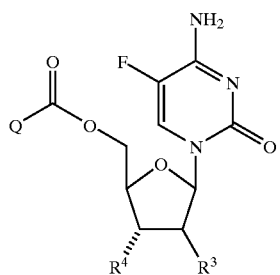
(II*)

wherein $R^3$ is X; and $R^4$ is $R^1CH_2C(=O)O$—;

(2) contacting the compound of Formula (II) or the compound of Formula (II*) with a suitable reducing agent in a suitable polar solvent, optionally in the-presence of a suitable acid catalyst, to form a compound of Formula (III):

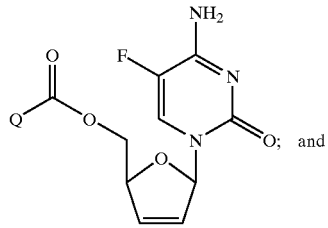
(III)

and (3) contacting the compound of Formula (III) with a suitable base to form the compound of Formula (IV).

In alternative second principle embodiment the present invention provides for a process for the preparation of a compound of Formula (IV):

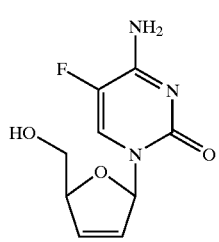
(IV)

comprising:

(1) contacting a compound of Formula (I):

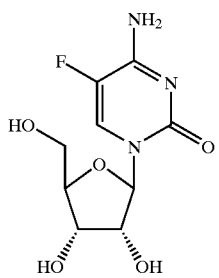
(I)

with an acyl halide of Formula Q—C(=O)X, wherein:

Q is $R^1CH_2C(=O)OC(R^1)_2$—;

X is Cl, Br or I;

$R^1$ is H, $CH_3$, $CH_2CH_3$ or $CH_2CH_2CH_3$;

$R^2$, at each occurrence, is independently selected from methyl, ethyl and propyl;

in a suitable polar aprotic solvent to form a mixture of compounds of Formula (II) and (II*):

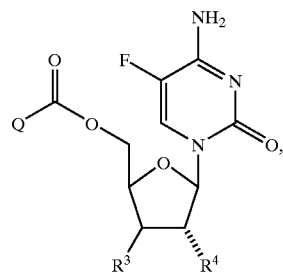
(II)

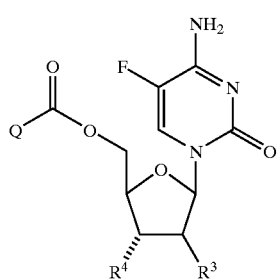
(II*)

wherein $R^3$ is X; and $R^4$ is $R^1CH_2C(=O)O$—;

(2) contacting the mixture of compounds of Formula (II) and (II*) with a suitable reducing agent in a suitable polar solvent, optionally in the presence of a suitable acid catalyst, to form a compound of Formula (III):

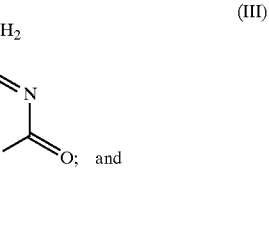
(III)

and (3) contacting the compound of Formula (III) with a suitable base to form the compound of Formula (IV).

In third principle embodiment the present invention provides for a process for the preparation of a compound of Formula (IV):

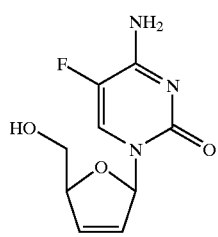
(IV)

comprising:

(1) contacting a compound of Formula (I):

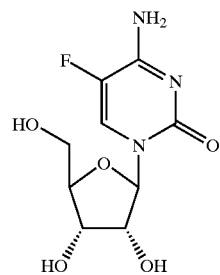

with 2-acetoxy-2-methyl-propionyl bromide in a suitable polar aprotic solvent to form a compound of Formula (II-a), a compound of Formula (II*-a), or a mixture of compounds of Formula (II-a) and (II*-a):

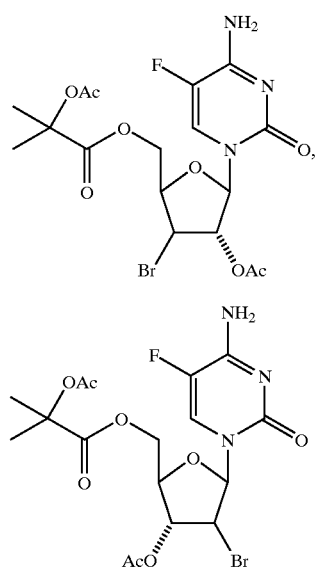

(2) contacting the compound of Formula (II-a), the compound of Formula (II*-a), or the mixture of compounds of Formula (II-a) and (II*-a); with a suitable reducing agent in a suitable polar solvent, optionally in the presence of a suitable acid catalyst, to form a compound of Formula (III-a):

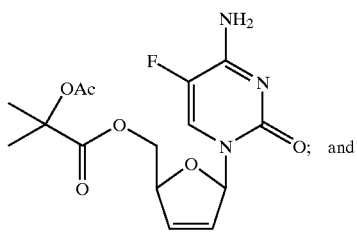

(3) contacting the compound of Formula (III-a) with a suitable base to form the compound of Formula (IV).

In one sub-embodiment the present invention provides for a process for the preparation of a compound of Formula (IV):

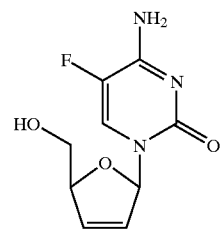

comprising:

(1) contacting a compound of Formula (I):

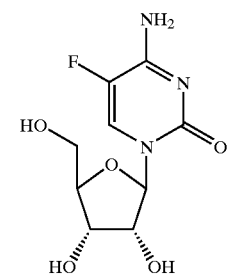

with 2-acetoxy-2-methyl-propionyl bromide in a suitable polar aprotic solvent to form a compound of Formula (II-a) or a compound of Formula (II*-a):

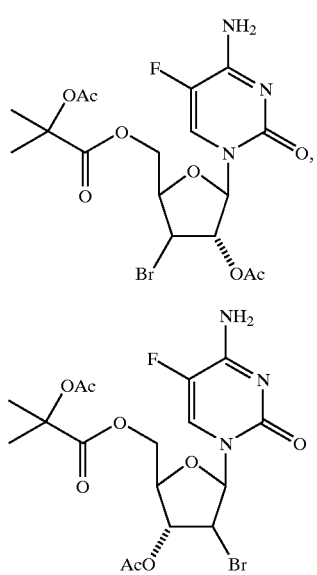

(2) contacting the compound of Formula (II-a) or the compound of Formula (II*-a) with a suitable reducing agent in a suitable polar solvent, optionally in the presence of a suitable acid catalyst, to form a compound of Formula (I-a):

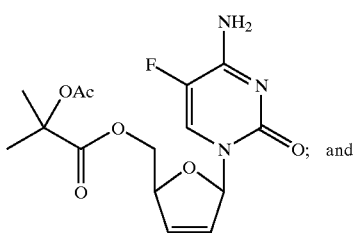
(III-a)

(3) contacting the compound of Formula (III-a) with a suitable base to form the compound of Formula (IV).

In another sub-embodiment the present invention provides for a process for the preparation of a compound of Formula (IV):

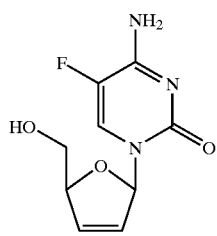
(IV)

comprising:
(1) contacting a compound of Formula (I):

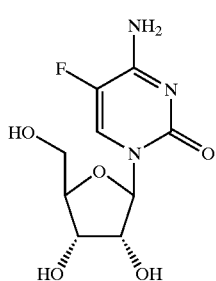
(I)

with 2-acetoxy-2-methyl-propionyl bromide in a suitable polar aprotic solvent to form a mixture of compounds of Formula (II-a) and (II*-a):

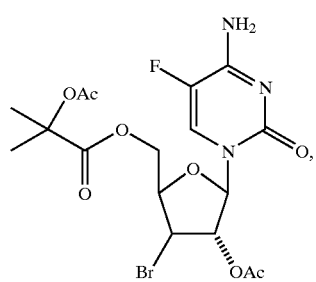
(II-a)

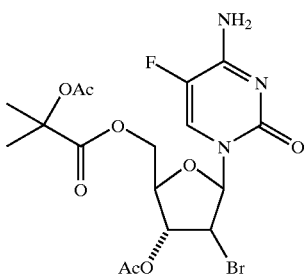
(II*-a)

(2) contacting the mixture of compounds of Formula (II-a) and (II*-a) with a suitable reducing agent in a suitable polar solvent, optionally in the presence of a suitable acid catalyst, to form a compound of Formula (III-a):

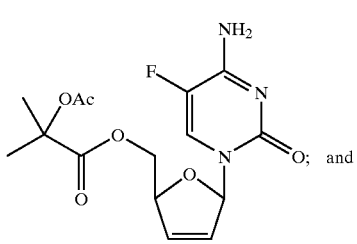
(III-a)

(3) contacting the compound of Formula (III-a) with a suitable base to form the compound of Formula (IV).

In a particular sub-embodiment, the process for the preparation of a compound of Formula (IV) in the first, second or third principle embodiment is provided, wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn;

in step (2), the suitable acid catalyst, when present, is selected from the group consisting of: acetic acid, propanoic acid, butyric acid, benzoic acid, toluene sulfonic acid, HCl, HBr, HI, and $H_2SO_4$;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

In an even more particular sub-embodiment, the process for the preparation of a compound of Formula (IV) in the first principle embodiment is provided, wherein: in step (1), the suitable polar aprotic solvent comprises a combination of acetonitrile and ethyl acetate;

in step (2), the suitable reducing agent is Zn—Cu couple;

in step (2), the suitable acid catalyst, when present, is acetic acid;

in step (2), the suitable polar solvent comprises a combination of methanol and ethyl acetate; and in step (3) the suitable base is sodium methoxide.

In fourth principle embodiment the present invention provides for a process for the preparation of a compound of Formula (IV):

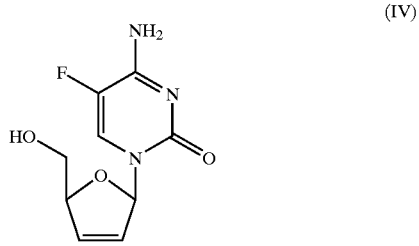
(IV)

comprising:

(1) contacting a compound of Formula (I):

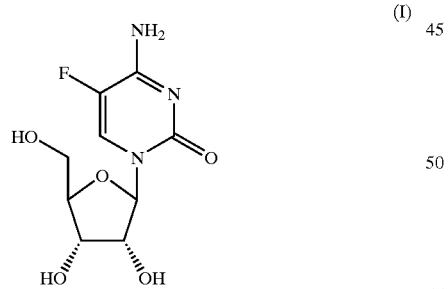
(I)

with 2-acetoxy-2-methyl-propionyl bromide in a suitable polar aprotic solvent comprising a combination of acetonitrile and ethyl acetate, wherein the ratio of acetonitrile to ethyl acetate is 1:4; to form a compound of Formula (II-a), a compound of Formula (II*-a), or a mixture of compounds of Formula (II-a) and (II*-a):

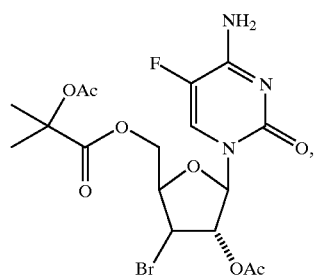
(II-a)

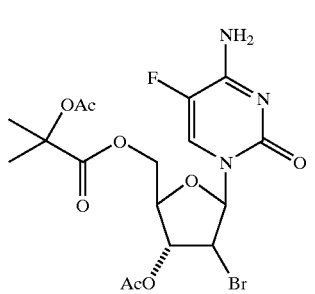
(II*-a)

(2) contacting the compound of Formula (II-a), the compound of Formula (II*-a), or the mixture of compounds of Formula (II-a) and (II*-a); with Zn—Cu couple in a suitable polar solvent comprising a combination of methanol and ethyl acetate, wherein the ratio of methanol to ethyl acetate is in the range of 1:2 to 1:4; optionally in the presence of acetic acid, to form a compound of Formula (III-a):

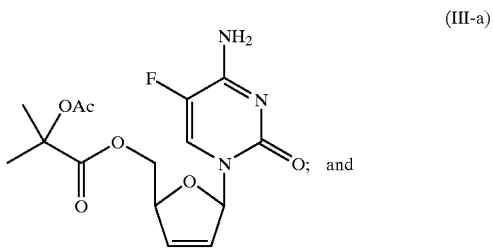
(III-a)

and (3) contacting the compound of Formula (III-a) with sodium methoxide to form the compound of Formula (IV).

In one sub-embodiment the present invention provides for a process for the preparation of a compound of Formula (IV):

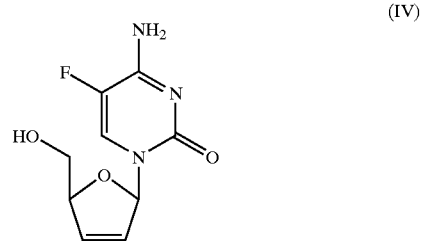
(IV)

comprising:

(1) contacting a compound of Formula (I):

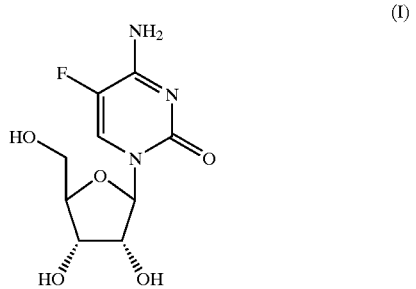

(I)

with 2-acetoxy-2-methyl-propionyl bromide in a suitable polar aprotic solvent comprising a combination of acetonitrile and ethyl acetate, wherein the ratio of acetonitrile to ethyl acetate is 1:4; to form a compound of Formula (II-a) or a compound of Formula (II*-a):

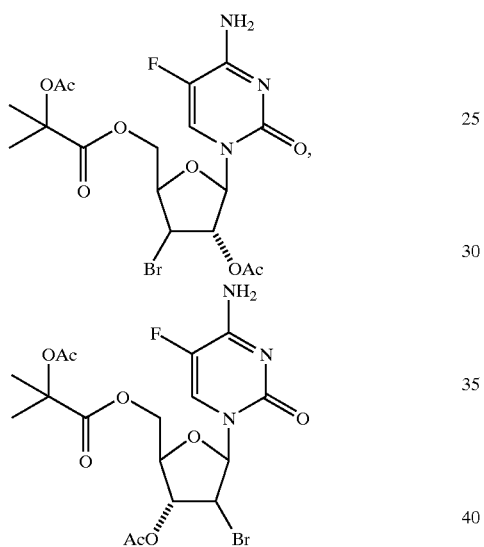

(2) contacting the compound of Formula (II-a) or the compound of Formula (II*-a); with Zn—Cu couple in a suitable polar solvent comprising a combination of methanol and ethyl acetate, wherein the ratio of methanol to ethyl acetate is in the range of 1:2 to 1:4; optionally in the presence of acetic acid, to form a compound of Formula (III-a):

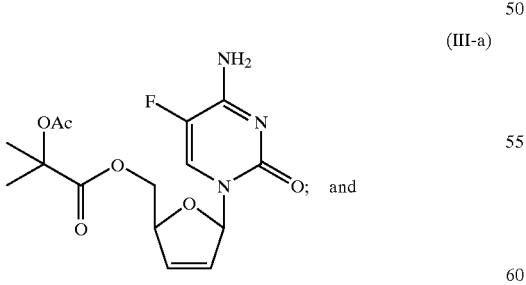

(III-a)

and (3) contacting the compound of Formula (III-a) with sodium methoxide to form the compound of Formula (IV).

In another sub-embodiment the present invention provides for a process for the preparation of a compound of Formula (IV):

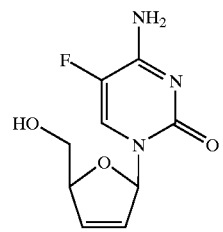

(IV)

comprising:

(1) contacting a compound of Formula (I):

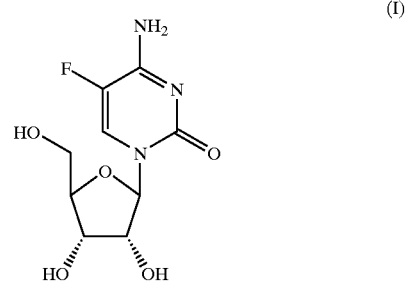

(I)

with 2-acetoxy-2-methyl-propionyl bromide in a suitable polar aprotic solvent comprising a combination of acetonitrile and ethyl acetate, wherein the ratio of acetonitrile to ethyl acetate is 1:4; to form a mixture of compounds of Formula (II-a) and (II*-a):

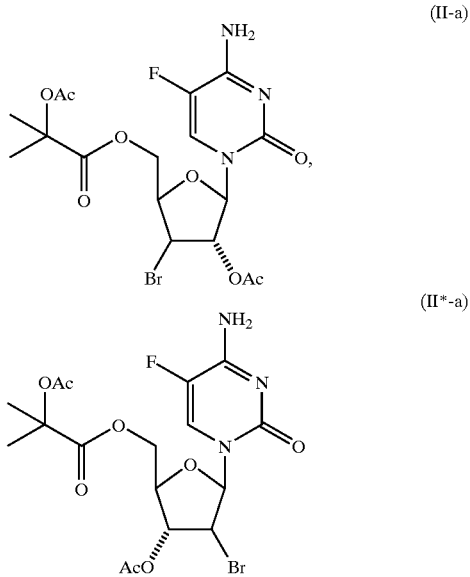

(2) contacting the mixture of compounds of Formula (II-a) and (II*-a) with Zn—Cu couple in a suitable polar solvent comprising a combination of methanol and ethyl acetate, wherein the ratio of methanol to ethyl acetate is in the range of 1:2 to 1:4; optionally in the presence of acetic acid, to form a compound of Formula (III-a):

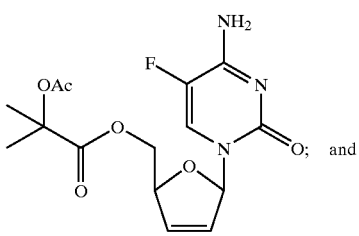

(III-a)

(3) contacting the compound of Formula (III-a) with sodium methoxide to form the compound of Formula (IV).

In a fifth principle embodiment, the present invention provides for a process for the preparation of a compound of Formula (III):

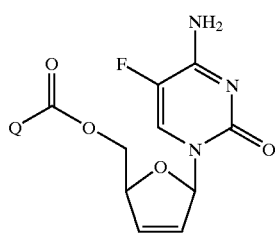

(III)

wherein:

Q is 2-($R^1CH_2CO_2$)phenyl-, $R^1CH_2$—, or $R^1CH_2C(=O)OC(R^2)_2$—; $R^1$ is H or $C_1$–$C_6$ alkyl;

$R^2$, at each occurrence, is independently selected from methyl, ethyl and propyl; comprising:

(1) contacting a compound of Formula (I):

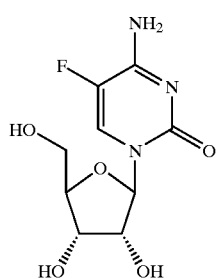

(I)

with an acyl halide of Formula Q—C(=O)X, wherein:

Q is 2-($R^1CH_2CO_2$)phenyl-, $R^1CH_2$—, or $R^1CH_2C(=O)OC(R^2)_2$—;

X is Cl, Br or I;

$R^1$ is H or $C_1$–$C_6$ alkyl;

$R^2$, at each occurrence, is independently selected from methyl, ethyl and propyl;

in a suitable polar aprotic solvent to form a compound of Formula (II), a compound of Formula (II*), or a mixture of compounds of Formula (II) and (II*):

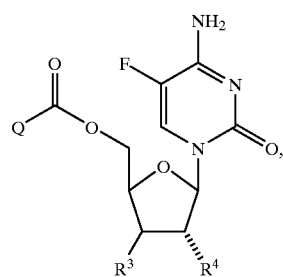

(II)

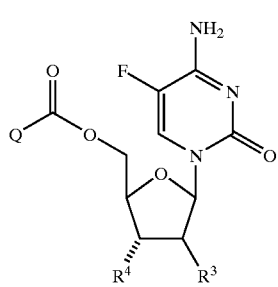

(II*)

wherein $R^3$ is X; and $R^4$ is $R^1CH_2C(=O)O$—; and (2) contacting the compound of Formula (II), the compound of Formula (II*), or the mixture of compounds of Formula (II) and (II*); with a suitable reducing agent in a suitable polar solvent, optionally in the presence of a suitable acid catalyst, to form a compound of Formula (III).

In a sixth embodiment, the present invention provides for a process for the preparation of a compound of Formula (III) wherein:

in step (1) the acyl halide of Formula Q—C(=O)X comprises:
2-acetoxy-2-methyl-propionyl bromide,
2-(acetoxy)-2-methyl-butanoyl bromide,
2-(acetoxy)-2-ethyl-butanoyl bromide, or
2-(acetoxy)-2-methyl-pentanoyl bromide;

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn;

in step (2), the suitable acid catalyst, when present, is selected from the group consisting of: acetic acid, propanoic acid, butyric acid, benzoic acid, toluene sulfonic acid, HCl, HBr, HI, and $H_2SO_4$; and in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether.

In seventh principle embodiment, the present invention provides for a process for the preparation of a compound of Formula (III-a):

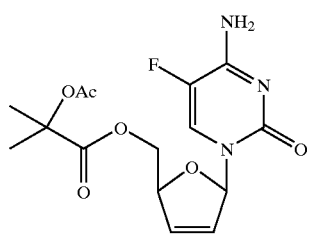
(III-a)

comprising:
(1) contacting a compound of Formula (I):

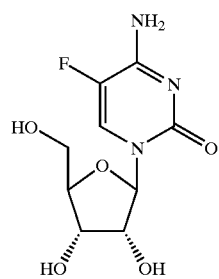
(I)

with 2-acetoxy-2-methyl-propionyl bromide in a suitable polar aprotic solvent to form a compound of Formula (II-a), a compound of Formula (II*-a), or a mixture of compounds of Formula (II-a) and (II*-a):

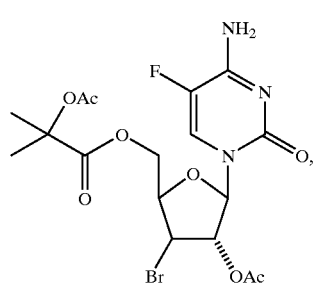
(II-a)

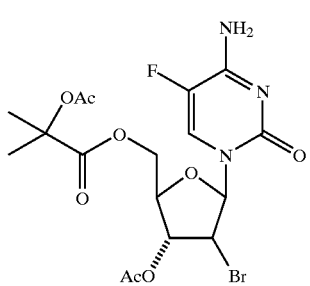
(II*-a)

(2) contacting the compound of Formula (II-a), the compound of Formula (II*-a), or the mixture of compounds of Formula (II-a) and (II*-a); with a suitable reducing agent in a suitable polar solvent, optionally in the presence of a suitable acid catalyst, to form a compound of Formula (III-a).

In one sub-embodiment, the present invention provides for a process for the preparation of a compound of Formula (III-a):

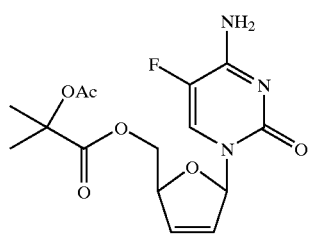
(III-a)

comprising:
(1) contacting a compound of Formula (I):

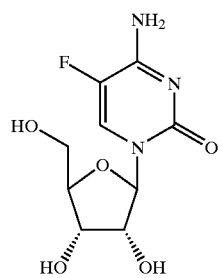
(I)

with 2-acetoxy-2-methyl-propionyl bromide in a suitable polar aprotic solvent comprising a combination of acetonitrile and ethyl acetate, wherein the ratio of acetonitrile to ethyl acetate is 1:4; to form a compound of Formula (II-a), a compound of Formula (II*-a), or a mixture of compounds of Formula (II-a) and (II*-a):

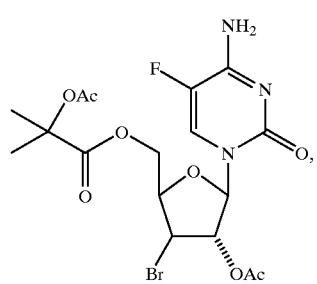
(II-a)

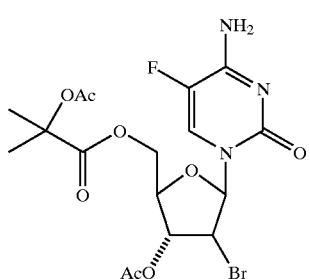
(II*-a)

(2) contacting the compound of Formula (II-a), the compound of Formula (II*-a), or the mixture of compounds of Formula (II-a) and (II*-a); with Zn—Cu couple in a suitable polar solvent comprising a combination of methanol and ethyl acetate, wherein the ratio of methanol to ethyl acetate is in the range of 1:2 to 1:4; optionally in the presence of acetic acid, to form a compound of Formula (III-a).

In a particular sub-embodiment, the process for the preparation of a compound of Formula (IV) in the fifth, sixth or seventh principle embodiment is provided, wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn;

in step (2), the suitable acid catalyst, when present, is selected from the group consisting of: acetic acid, propanoic acid, butyric acid, benzoic acid, toluene sulfonic acid, HCl, HBr, HI, and $H_2SO_4$;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

In an even more particular sub-embodiment, the process for the preparation of a compound of Formula (IV) in the first principle embodiment is provided, wherein:

in step (1), the suitable polar aprotic solvent comprises a combination of acetonitrile and ethyl acetate;

in step (2), the suitable reducing agent is Zn—Cu couple;

in step (2), the suitable acid catalyst, when present, is acetic acid; in step (2), the suitable polar solvent comprises a combination of methanol and ethyl acetate; and in step (3) the suitable base is sodium methoxide.

In an eighth principle embodiment, the present invention provides for a compound of Formula (II) or (II*):

(II)

(II*)

or a pharmaceutically acceptable salt thereof, wherein:
Q is $R^1CH_2$— or $R^1CH_2C(=O)OC(R^2)_2$—;
$R^1$ is H or $C_1$–$C_6$ alkyl;

$R^2$ is independently selected from methyl, ethyl and propyl;
$R^3$ is Cl, Br or I; and
$R^4$ is $R^1CH_2C(=O)O$—.

In a ninth principle embodiment, the present invention provides for a compound of Formula (II-a) or (II*-a),

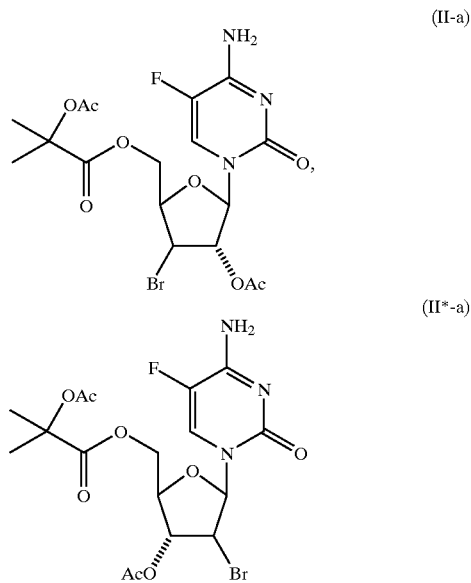

or a pharmaceutically acceptable salt thereof.

In a tenth principle embodiment, the present invention provides for a compound of Formula (III):

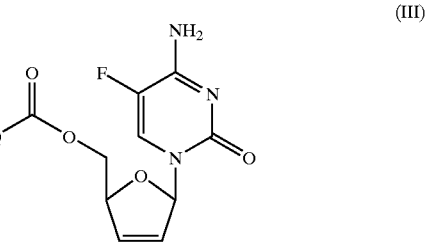

or a pharmaceutically acceptable salt thereof, wherein:
Q is $R^1CH_2$— or $R^1CH_2C(=O)OC(R^2)_2$—;
$R^1$ is H or $C_1$–$C_6$ alkyl; and
$R^2$ is independently selected from methyl, ethyl and propyl.

In an eleventh principle embodiment, the present invention provides for a compound of Formula (III-a),

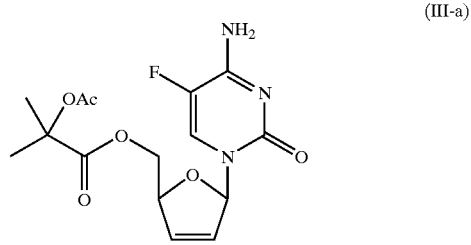

or a pharmaceutically acceptable salt thereof.

In a twelfth principle embodiment, the present invention provides for a process for the preparation of a compound of Formula (IV):

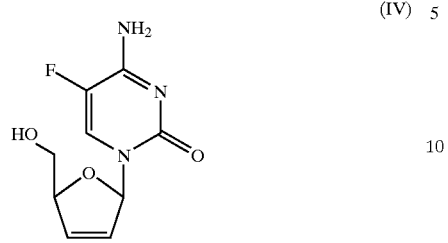
(IV)

comprising:
(1) contacting a compound of Formula (V):

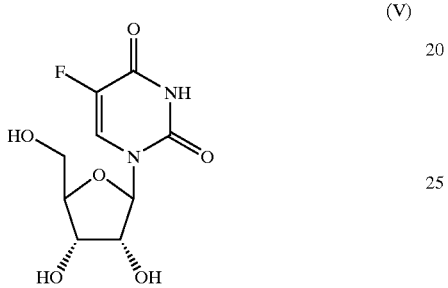
(V)

with an acyl halide of Formula Q—C(=O)X, wherein:
Q is 2-(R$^1$CH$_2$CO$_2$)phenyl-, R$^1$CH$_2$—, or R$^1$CH$_2$C(=O)OC(R$^2$)$_2$—;
X is Cl, Br, or I;
R$^1$ is H or C$_1$–C$_6$ alkyl;
R$^2$, at each occurrence, is independently selected from methyl, ethyl, and propyl; in a suitable polar aprotic solvent to form a compound of Formula (VI), a compound of Formula (VI*), or a mixture of compounds of Formula (VI) and (VI*):

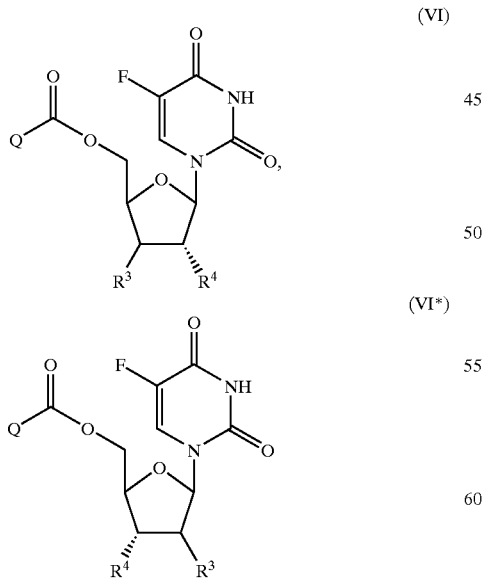
(VI)

(VI*)

wherein R$^3$ is X; and R$^4$ is R$^1$CH$_2$C(=O)O—;
(2) contacting the compound of Formula (VI), the compound of Formula (VI*), or the mixture of compounds of Formula (VI) and (VI*); with a reducing agent in a suitable polar solvent, optionally in the presence of an acid catalyst, to form a compound of Formula (VII):

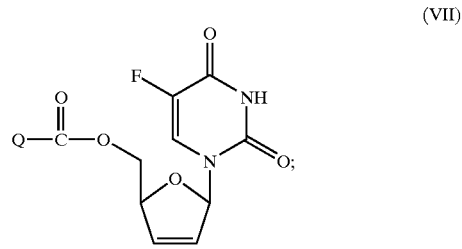
(VII)

(3a) contacting the compound of Formula (III) with an activating agent in the presence of an amine base, to form a compound of Formula (VIII):

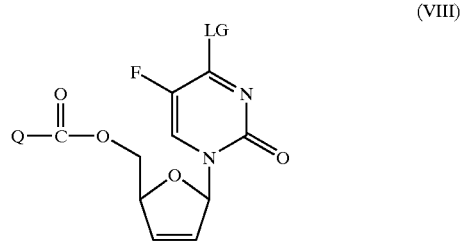
(VIII)

wherein LG is a leaving group derived from the activating agent;

(3b) contacting the compound of Formula (VIII) with an aminating agent to form a compound of Formula (III),

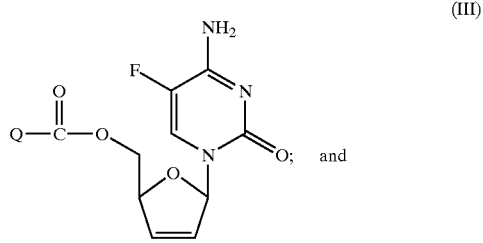
(III)

and (4) contacting the compound of Formula (III) with a suitable base to form the compound of Formula (IV).

In one sub-embodiment the present invention provides for a process for the preparation of a compound of Formula (IV):

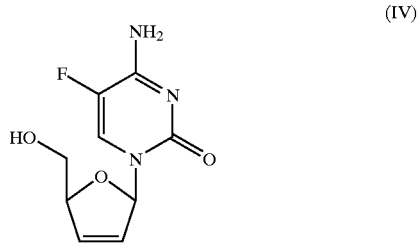
(IV)

comprising:

(1) contacting a compound of Formula (V):

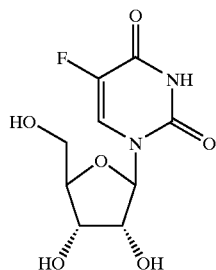
(V)

with an acyl halide of Formula Q—C(=O)X, wherein:
Q is 2-(R¹CH₂CO₂)phenyl-, R¹CH₂—, or R¹CH₂C(=O)OC(R²)₂—;
X is Cl, Br, or I;
R¹ is H or $C_1$–$C_6$ alkyl;
R², at each occurrence, is independently selected from methyl, ethyl, and propyl;
in a suitable polar aprotic solvent to form a mixture of compounds of Formula (VI) and (VI*):

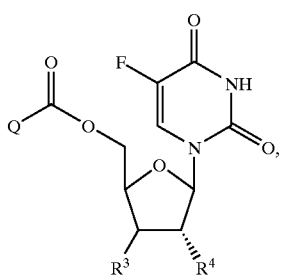
(VI)

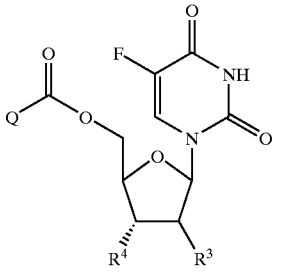
(VI*)

wherein R³ is X; and R⁴ is R¹CH₂C(=O)O—;
(2) contacting the mixture of compounds of Formula (VI) and (VI*); with a reducing agent in a suitable polar solvent, optionally in the presence of an acid catalyst, to form a compound of Formula (VII):

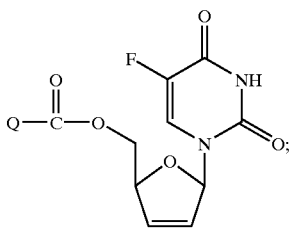
(VII)

(3a) contacting the compound of Formula (VII) with an activating agent in the presence of an amine base, to form a compound of Formula (VIII):

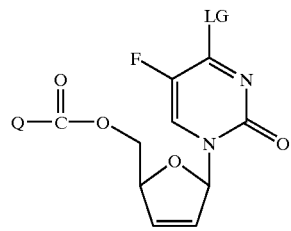
(VIII)

wherein LG is a leaving group derived from the activating agent;

(3b) contacting the compound of Formula (VIII) with an aminating agent to form a compound of Formula (III),

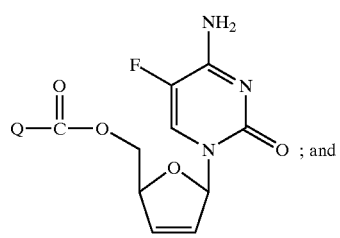
(III)

; and (4) contacting the compound of Formula (III) with a suitable base to form the compound of Formula (IV).

In a thirteenth principle embodiment the present invention provides for a process for the preparation of a compound of Formula (IV), wherein:

in step (1) the acyl halide of Formula Q—C(=O)X comprises:
2-acetoxy-2-methyl-propionyl bromide,
2-(acetoxy)-2-methyl-butanoyl bromide,
2-(acetoxy)-2-ethyl-butanoyl bromide, or
2-(acetoxy)-2-methyl-pentanoyl bromide;

in step (1), the suitable polar aprotic solvent comprises one polar aprotic solvent or a combination of two or more polar aprotic solvents, and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the reducing agent is selected from the group consisting of: Fe, Zn—Cu couple and Zn;

in step (2), the acid catalyst, when present, is selected from the group consisting of: acetic acid, propanoic acid, butyric acid, benzoic acid, toluene sulfonic acid, HCl, HBr, HI, and $H_2SO_4$;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether;

in step (3-a) the activating agent is selected from the group consisting of: methanesulfonyl chloride, trifluoromethyl sulfonyl chloride, ethanesulfonyl chloride, benzenesulfonyl chloride, p-toluene-sulfonyl chloride, triazole/phosphorus oxychloride and triazole/diphenyl chloro-phosphate;

in step (3-a) the amine base is selected from the group consisting of: triethylamine, tributylamine, N-methylmorpholine, N,N-diisopropyl-ethylamine, N,N-dimethylcyclohexylamine, N,N-diethylcyclohexylamine, N,N-dimethyloctylamine, tetramethylethylenediamine, pyridine, N,N-dimethylaminopyridine, 1,4-diazabicyclo[2.2.2]octane, 1,8-diazabicyclo[5.4.0]undec-7-ene, and 1,5-diazabicyclo[4.3.0]non-5-ene;

in step (3-a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl;

in step (3-b) the aminating agent is selected from the group consisting of: $NH_3$, ammonium hydroxide, and ammonium carbonate; and in step (3-c) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

In a fourteenth principle embodiment the present invention provides for a process for the preparation of a compound of Formula (IV):

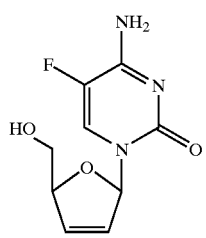

(IV)

comprising:

(1) contacting a compound of Formula (I):

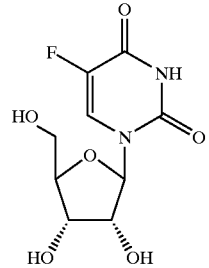

(V)

with 2-acetoxy-2-methyl-propionyl bromide in a suitable polar aprotic solvent to form a compound of Formula (VI-a), a compound of Formula (VI*-a), or a mixture of compounds of Formula (VI-a) and (VI*-a):

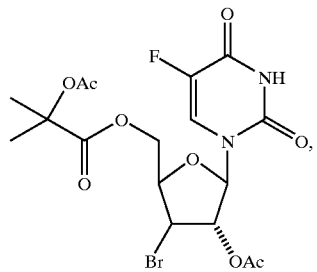

(VI-a)

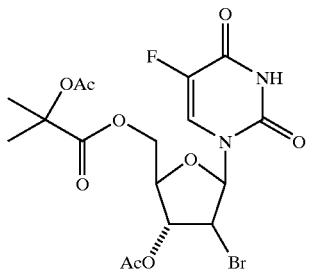

(VI*-a)

(2) contacting the compound of Formula (VI-a), the compound of Formula (VI*-a), or the mixture of compounds of Formula (VI-a) and (VI*-a); with a reducing agent in a suitable polar solvent, optionally in the presence of an acid catalyst, to form a compound of Formula (VII-a):

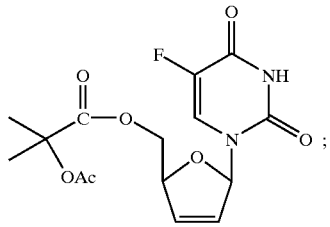

(VII-a)

(3a) contacting the compound of Formula (VII-a) with an activating agent selected from the group consisting of:
 i) an aryl sulfonyl halide,
 ii) an alkyl sulfonyl halide, and
 iii) 1,2,4-triazole in the presence of a phosphorus chloride;
in the presence of an amine base, to form a compound of Formula (VIII-a);

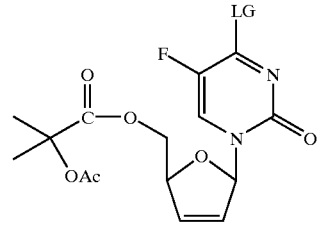

(VIII-a)

wherein LG is a leaving group derived from the activating agent;

(3b) contacting the compound of Formula (VIII-a) with an aminating agent to form a compound of Formula (III-a),

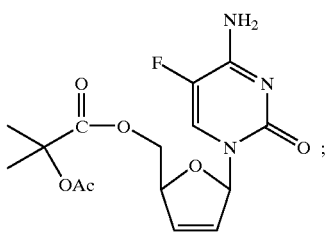
(III-a)

and (4) contacting the compound of Formula (III-a) with a suitable base to form the compound of Formula (IV).

In one sub-embodiment the present invention provides for a process for the preparation of a compound of Formula (IV):

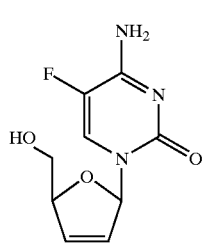
(IV)

comprising:

(1) contacting a compound of Formula (V):

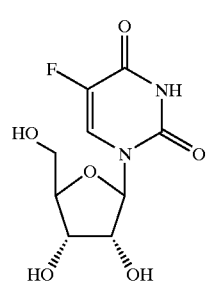
(V)

with 2-acetoxy-2-methyl-propionyl bromide in a suitable polar aprotic solvent to form a mixture of compounds of Formula (VI-a) and (VI*-a):

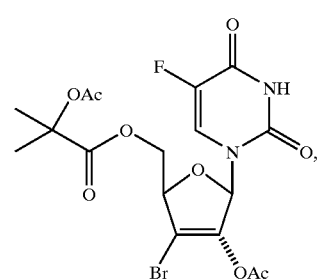
(VI-a)

-continued

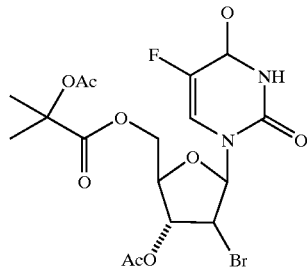
(VI*-a)

(2) contacting the mixture of compounds of Formula (VI-a) and (VI*-a); with a reducing agent in a suitable polar solvent, optionally in the presence of an acid catalyst, to form a compound of Formula (VII-a):

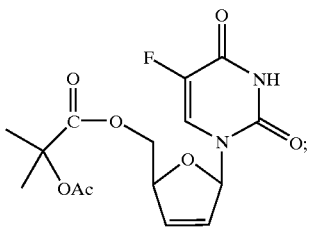
(VII-a)

(3a) contacting the compound of Formula (VII-a) with a activating agent selected from the group consisting of:
 i) an aryl sulfonyl halide,
 ii) an alkyl sulfonyl halide, and
 iii) 1,2,4-triazole in the presence of a phosphorus chloride;
in the presence of an amine base, to form a compound of Formula (VIII-a);

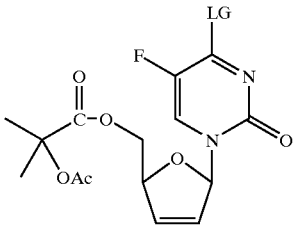
(VIII-a)

wherein LG is a leaving group derived from the activating agent;

(3b) contacting the compound of Formula (VIII-a) with an aminating agent to form a compound of Formula (III-a),

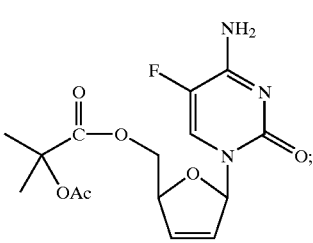
(III-a)

and (4) contacting the compound of Formula (III-a) with a suitable base to form the compound of Formula (IV).

In a particular sub-embodiment, the process for the preparation of a compound of Formula (IV) in the twelfth, thirteenth or fourteenth principle embodiment is provided, wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the reducing agent is selected from the group consisting of: Fe, Zn—Cu couple and Zn;

in step (2), the acid catalyst, when present, is selected from the group consisting of:
  acetic acid, propanoic acid, butyric acid, benzoic acid, toluene sulfonic acid, HCl, HBr, HI, and $H_2SO_4$;

in step (2), the suitable polar solvent comprises one polar solvent or a combination of two or more polar solvents; and is selected from the group consisting of:
  methanol, ethanol, propanol, ethyl acetate, propyl acetate, butyl acetate, isopropyl acetate, acetonitrile, tetrahydrofuran, dimethoxy ethane, and 2-methoxyethyl ether;

in step (3-a) the activating agent is selected from the group consisting of:
  methanesulfonyl chloride, trifluoromethyl sulfonyl chloride, ethanesulfonyl chloride, benzenesulfonyl chloride,
  p-toluene-sulfonyl chloride, triazole/phosphorus oxychloride and triazole/diphenyl chloro-phosphate;

in step (3-a) the amine base is selected from the group consisting of:
  triethylamine,
  tributylamine,
  N-methylmorpholine, N,N-diisopropyl-ethylamine,
  tetramethylethylenediamine, pyridine,
  N,N-dimethyl-aminopyridine,
  1,4-diazabicyclo[2.2.2]octane, and
  1,8-diazabicyclo[5.4.0]undec-7-ene;

in step (3-a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl;

in step (3-b) the aminating agent is selected
from the group: $NH_3$, ammonium hydroxide, and ammonium carbonate; and in step (3-c) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

In an even more particular sub-embodiment, the process for the preparation of a compound of Formula (IV) in the twelfth, thirteenth or fourteenth principle embodiment is provided, wherein:

in step (1), the suitable polar aprotic solvent comprises one solvent which is acetonitrile;

in step (2), the reducing agent is Zn—Cu couple;

in step (2), the acid catalyst, when present, is acetic acid;

in step (2), the suitable polar solvent comprises a combination of methanol and ethyl acetate;

in step (3-a) the activating agent is triazole/phosphorus oxychloride;

in step (3-a) the amine base is triethylamine;

in step (3-a) the leaving group LG is triazolyl;

in step (3-b), the aminating agent is $NH_3$; and in step (3-c) the suitable base is sodium methoxide.

In a fifteenth principle embodiment the present invention provides for a process for the preparation of a compound of Formula (IV):

(IV)

comprising:

(1) contacting a compound of Formula (I):

(V)

with 2-acetoxy-2-methyl-propionyl bromide in acetonitrile to form a compound of Formula (VI-a), a compound of Formula (VI*-a), or a mixture of compounds of Formula (VI-a) and (VI*-a):

(VI-a)

-continued (VI*-a)
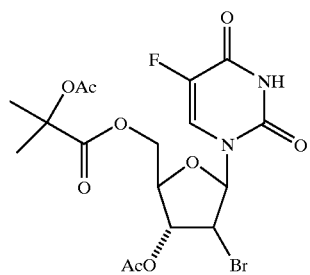

(2) contacting the compound of Formula (VI-a), the compound of Formula (VI*-a), or the mixture of compounds of Formula (VI-a) and (VI*-a); with Zn—Cu couple in a suitable polar solvent comprising a combination of methanol and ethyl acetate, wherein the ratio of methanol to ethyl acetate is in the range of 1:2 to 1:4; optionally in the presence of acetic acid, to form a compound of Formula (VII-a):

(VII-a)
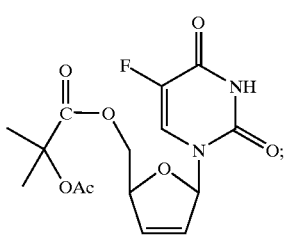

(3a) contacting the compound of Formula (VII-a) with 1,2,4-triazole/phosphorus oxychloride, in the presence of triethylamine, to form a compound of Formula (VIII-a):

(VIII-a)
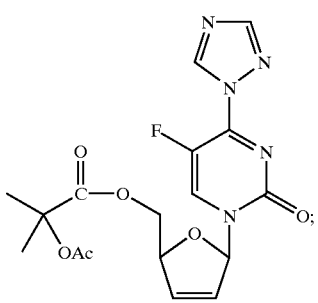

(3b) contacting the compound of Formula (VIII-a) with NH₃, to form a compound of Formula (III-a), and (4) contacting the compound of Formula (III-a) with sodium methoxide to form the compound of Formula (IV).

In one sub-embodiment the present invention provides for a process for the preparation of a compound of Formula (IV):

(IV)
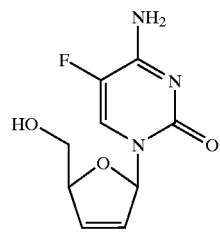

comprising:

(1) contacting a compound of Formula (V):

(V)
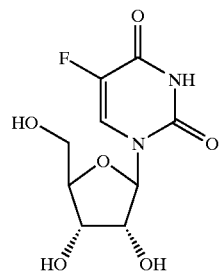

with 2-acetoxy-2-methyl-propionyl bromide in acetonitrile to form a mixture of compounds of Formula (VI-a) and (VI*-a):

(VI-a)
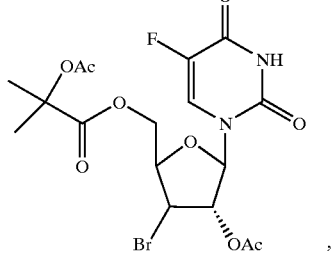

(VI*-a)
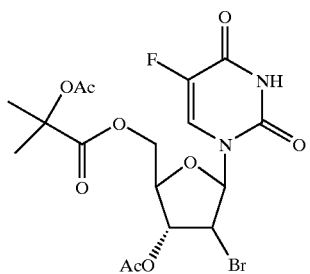

(2) contacting the mixture of compounds of Formula (VI-a) and (VI*-a); with Zn—Cu couple in a suitable polar solvent comprising a combination of methanol and ethyl acetate, wherein the ratio of methanol to ethyl acetate is in the range of 1:2 to 1:4; optionally in the presence of acetic acid, to form a compound of Formula (VII-a):

(VII-a)

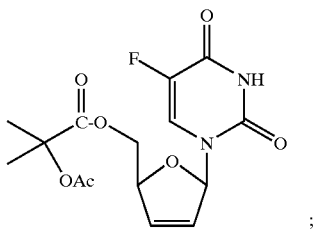
;

(3a) contacting the compound of Formula (III-a) with 1,2,4-triazole/phosphorus oxychloride, in the presence of triethylamine, to form a compound of Formula (VIII-a):

(VIII-a)

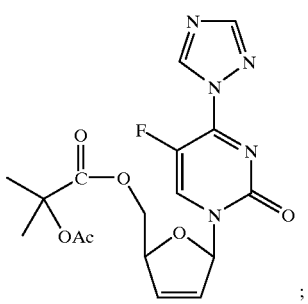
;

(3b) contacting the compound of Formula (VIII-a) with NH$_3$, to form a compound of Formula (III-a), and (4) contacting the compound of Formula (III-a) with sodium methoxide to form the compound of Formula (IV).

In a sixteenth principle embodiment, the present invention provides for a process for the preparation of a compound of Formula (III):

(III)

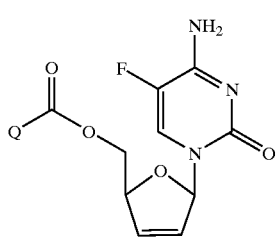

wherein:

Q is 2-(R$^1$CH$_2$CO$_2$)phenyl-, R$^1$CH$_2$—, or R$^1$CH$_2$C(=O)OC(R$^2$)$_2$—;

R$^1$ is H or C$_1$–C$_6$ alkyl;

R$^2$, at each occurrence, is independently selected from methyl, ethyl, and propyl; comprising:

(1) contacting a compound of Formula (V):

(V)

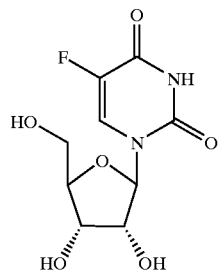

with an acyl halide of Formula Q—C(=O)X, wherein:

Q is 2-(R$^1$CH$_2$CO$_2$)phenyl-, R$^1$CH$_2$—, or R$^1$CH$_2$C(=O)OC(R$^2$)$_2$—;

X is Cl, Br, or I;

R$^1$ is H or C$_1$–C$_6$ alkyl;

R$^2$, at each occurrence, is independently selected from methyl, ethyl, and propyl;

in a suitable polar aprotic solvent to form a compound of Formula (VI), a compound of Formula (VI*), or a mixture of compounds of Formula (VI) and (VI*):

(VI)

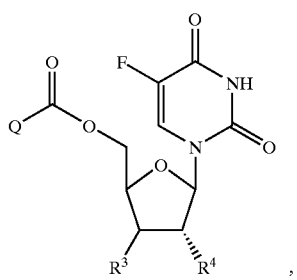
, (VI*)

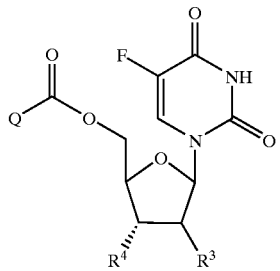

wherein R$^3$ is X; and R$^4$ is R$^1$CH$_2$C(=O)O—;

(2) contacting the compound of Formula (VI), the compound of Formula (VI*), or the mixture of compounds of Formula (VI) and (VI*); with a reducing agent in a suitable polar solvent, optionally in the presence of an acid catalyst, to form a compound of Formula (VII):

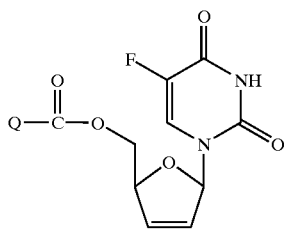

(VII)

(3a) contacting the compound of Formula (VII) with an activating agent in the presence of an amine base, to form a compound of Formula (VIII):

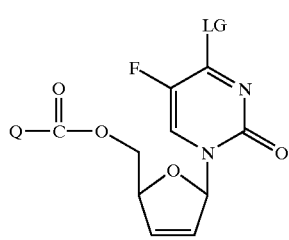

(VIII)

wherein LG is a leaving group derived from the activating agent;

(3b) contacting the compound of Formula (VIII) with an aminating agent to form a compound of Formula (III).

In a seventeenth principle embodiment, the present invention provides for a process for the preparation of a compound of Formula (III) wherein:

in step (1) the acyl halide of Formula Q—C(=O)X comprises:
2-acetoxy-2-methyl-propionyl bromide,
2-(acetoxy)-2-methyl-butanoyl bromide,
2-(acetoxy)-2-ethyl-butanoyl bromide, or
2-(acetoxy)-2-methyl-pentanoyl bromide;

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the reducing agent is selected from the group consisting of: Fe, Zn—Cu couple and Zn;

in step (2), the acid catalyst, when present, is selected from the group consisting of:
acetic acid, propanoic acid, butyric acid, benzoic acid, toluene sulfonic acid, HCl, HBr, HI, and $H_2SO_4$;

in step (2), the suitable polar solvent comprises one polar solvent or a combination of two or more polar solvents; and is selected from the group consisting of:
methanol, ethanol, propanol, ethyl acetate, propyl acetate, butyl acetate, isopropyl acetate, acetonitrile, tetrahydrofuran, dimethoxy ethane, and 2-methoxyethyl ether;

in step (3-a) the activating agent is selected from the group consisting of:
methanesulfonyl chloride, trifluoromethyl sulfonyl chloride, ethanesulfonyl chloride, benzenesulfonyl chloride, p-toluene-sulfonyl chloride, triazole/phosphorus oxychloride and triazole/diphenyl chloro-phosphate;

in step (3-a) the amine base is selected from the group consisting of:
triethylamine,
tributylamine,
N-methylmorpholine, N,N-diisopropyl-ethylamine,
N,N-dimethylcyclohexylamine,
N,N-diethylcyclohexylamine,
N,N-dimethyloctylamine, tetramethylethylenediamine,
pyridine, N,N-dimethyl-aminopyridine,
1,4-diazabicyclo[2.2.2]octane,
1,8-diazabicyclo[5.4.0]undec-7-ene, and
1,5-diazabicyclo[4.3.0]non-5-ene;

in step (3-a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl;

in step (3-b) the aminating agent is selected from the group: $NH_3$, ammonium hydroxide, and ammonium carbonate.

In eighteenth principle embodiment, the present invention provides for a process for the preparation of a compound of Formula (III-a):

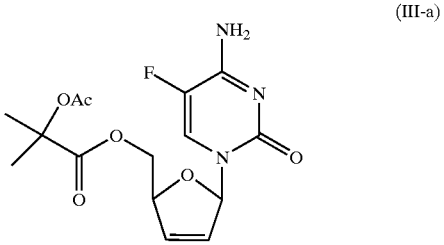

(III-a)

comprising:

(1) contacting a compound of Formula (V):

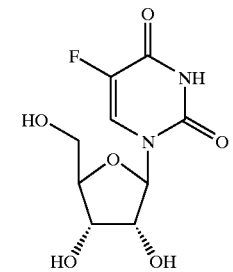

(V)

with 2-acetoxy-2-methyl-propionyl bromide in a suitable polar aprotic solvent to form a compound of Formula (VI-a), a compound of Formula (VI*-a), or a mixture of compounds of Formula (VI-a) and (VI*a):

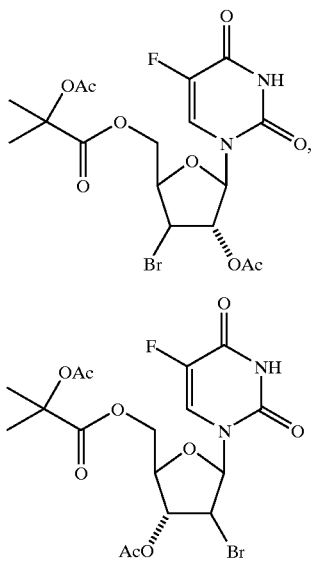

(VI-a)

(VI*-a)

(2) contacting the compound of Formula (VI-a), the compound of Formula (VI*-a), or the mixture of compounds of Formula (VI-a) and (VI*-a); with a reducing agent in a suitable polar solvent, optionally in the presence of an acid catalyst, to form a compound of Formula (VII-a);

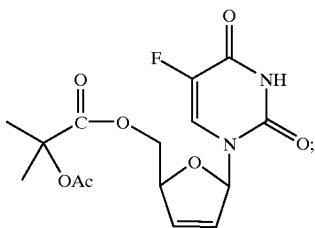

(VII-a)

(3a) contacting the compound of Formula (VII-a) with a activating agent selected from the group consisting of:
i) an aryl sulfonyl halide,
ii) an alkyl sulfonyl halide, and
iii) 1,2,4-triazole in the presence of a phosphorus chloride;
in the presence of an amine base, to form a compound of Formula (VIII-a):

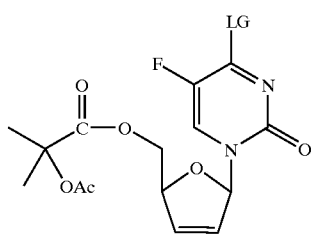

(VIII-a)

wherein LG is a leaving group derived from the activating agent; and
(3b) contacting the compound of Formula (VIII-a) with an aminating agent to form a compound of Formula (III-a).

In a particular sub-embodiment, the process for the preparation of a compound of Formula (IV) in the sixteenth, seventeenth or eighteenth principle embodiment is provided, wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the reducing agent is selected from the group consisting of: Fe, Zn—Cu couple and Zn;

in step (2), the acid catalyst, when present, is selected from the group consisting of:
acetic acid, propanoic acid, butyric acid, benzoic acid, toluene sulfonic acid, HCl, HBr, HI, and $H_2SO_4$;

in step (2), the suitable polar solvent comprises one polar solvent or a combination of two or more polar solvents; and is selected from the group consisting of:
methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3-a) the activating agent is selected from the group consisting of:
methanesulfonyl chloride, trifluoromethyl sulfonyl chloride, ethanesulfonyl chloride, benzenesulfonyl chloride, p-toluene-sulfonyl chloride, triazole/phosphorus oxychloride and triazole/diphenyl chloro-phosphate;

in step (3-a) the amine base is selected from the group consisting of: triethylamine, tributylamine, N-methylmorpholine, N,N-diisopropyl-ethylamine, tetramethylethylenediamine, pyridine, N,N-dimethyl-aminopyridine, 1,4-diazabicyclo[2.2.2]octane, and 1,8-diazabicyclo[5.4.0]undec-7-ene;

in step (3-a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl; and in step (3-b) the aminating agent is selected from the group: $NH_3$, ammonium hydroxide, and ammonium carbonate.

In an even more particular sub-embodiment, the process for the preparation of a compound of Formula (IV) in the sixteenth, seventeenth or eighteenth principle embodiment is provided, wherein:

in step (1), the suitable polar aprotic solvent comprises one solvent which is acetonitrile;

in step (2), the reducing agent is Zn—Cu couple;

in step (2), the acid catalyst, when present, is acetic acid;

in step (2), the suitable polar solvent comprises a combination of methanol and ethyl acetate;

in step (3-a) the activating agent is triazole/phosphorus oxychloride;

in step (3-a) the amine base is triethylamine;

in step (3-a) the leaving group LG is triazolyl; and in step (3-b), the aminating agent is $NH_3$.

In a nineteenth principle embodiment, the present invention provides for a process for the preparation of a compound of Formula (III-a):

(III-a)

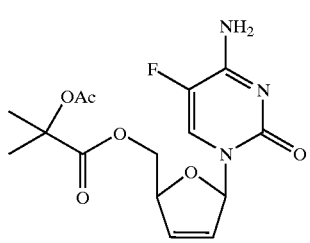

comprising:

(1) contacting a compound of Formula (V):

(V)

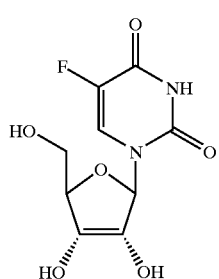

with 2-acetoxy-2-methyl-propionyl bromide in acetonitrile to form a compound of Formula (VI-a), a compound of Formula (VI*-a), or a mixture of compounds of Formula (VI-a) and (VI*-a):

(VI-a)

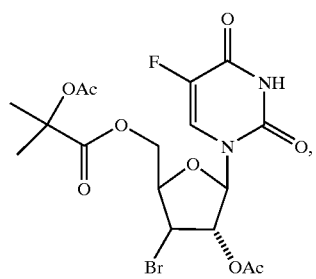

(VI*-a)

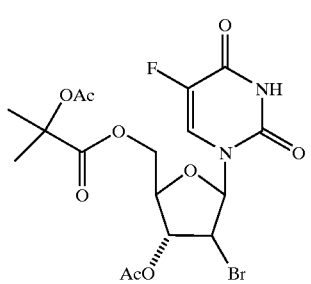

(2) contacting the compound of Formula (VI-a), the compound of Formula (VI*-a), or the mixture of compounds of Formula (VI-a) and (VI*-a); with Zn—Cu couple in a suitable polar solvent comprising a combination of methanol and ethyl acetate, wherein the ratio of methanol to ethyl acetate is in the range of 1:2 to 1:4; optionally in the presence of acetic acid, to form a compound of Formula (VII-a):

(VII-a)

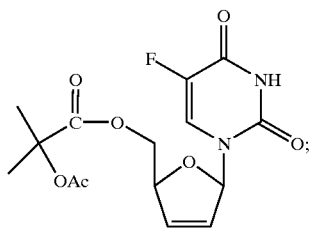

(3a) contacting the compound of Formula (III-a) with 1,2,4-triazole/phosphorus oxychloride, in the presence of triethylamine, to form a compound of Formula (VIII-a):

(VIII-a)

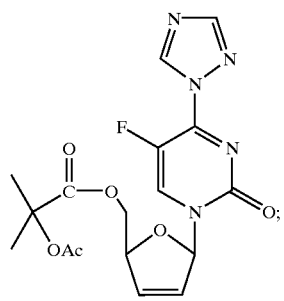

and (3b) contacting the compound of Formula (VIII-a) with $NH_3$, to form a compound of Formula (III-a).

In a twentieth principle embodiment, the present invention provides for a compound of Formula (VI) or (VI*):

(VI)

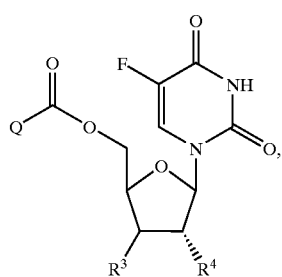

(VI*)

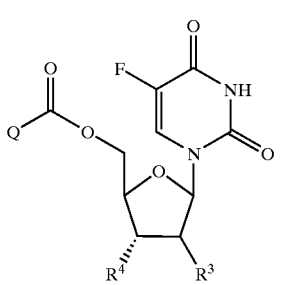

or a pharmaceutically acceptable salt thereof, wherein:

Q is $R^1CH_2$— or $R^1CH_2C(=O)OC(R^2)_2$—;

$R^1$ is H or $C_1$–$C_6$ alkyl;

$R^2$ is independently selected from methyl, ethyl, and propyl;

$R^3$ is Cl, Br, or I; and $R^4$ is $R^1CH_2C(=O)O$—.

In a twenty-first principle embodiment, the present invention provides for a compound of Formula (VI-a) or (VI*-a):

(VI-a)

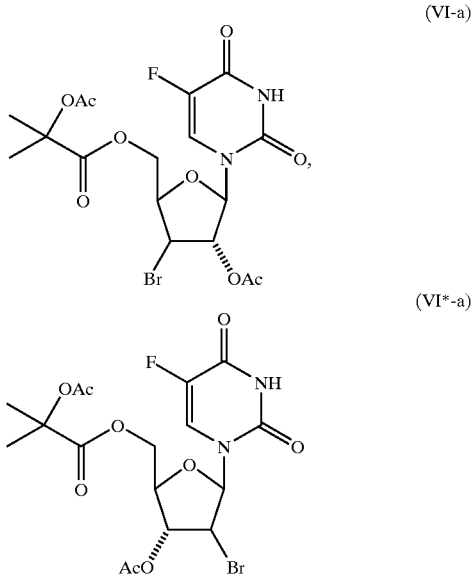

(VI*-a)

or a pharmaceutically acceptable salt thereof.

In a twenty-second principle embodiment, the present invention provides for a compound of Formula (VII):

(VII)

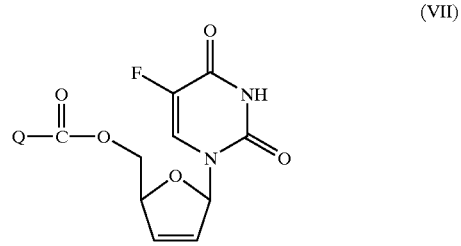

or a pharmaceutically acceptable salt thereof, wherein:
Q is $R^1CH_2$— or $R^1CH_2C(=O)OC(R^2)_2$—;
$R^1$ is H or $C_1$–$C_6$ alkyl; and
$R^2$ is independently selected from methyl, ethyl, and propyl.

In a twenty-third principle embodiment, the present invention provides for a compound of Formula (VII-a), (VII-a)

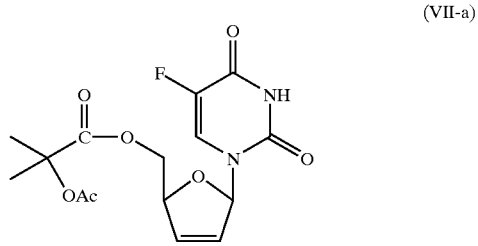

or a pharmaceutically acceptable salt thereof.

The present invention is useful for the preparation of β-D-2',3'-didehydro-2',3'-dideoxy-5-fluorocytidine which is useful as an agent for inhibiting the growth or replication of HIV.

The process of the present invention is also useful for the preparation of β-D-2',3'-didehydro-2',3'-dideoxy-5-fluorocytidine which is useful as human immunodeficiency virus (HIV) reverse transcriptase inhibitor. Such HIV reverse transcriptase inhibitor is useful for the inhibition of HIV in an ex vivo sample containing HIV or expected to be exposed to HIV. Thus, such HIV reverse transcriptase inhibitor can be used to inhibit HIV present in a body fluid sample (for example, a body fluid or semen sample) which contains or is suspected to contain or be exposed to HIV. Such HIV reverse transcriptase inhibitor is also useful as standards or reference compounds for use in tests or assays for determining the ability of an agent to inhibit viral replication and/or HIV reverse transcriptase, for example in a pharmaceutical research program. Thus, such HIV reverse transcriptase inhibitor can be used as a control or reference compound in such assays and as a quality control standard.

I. Stereoisomerism and Polymorphism

Compounds of the present invention have at least two chiral centers, and can exist in and be isolated in optically active and racemic forms. Some compounds can exhibit polymorphism. The present invention encompasses racemic, optically-active, polymorphic, chiral, diastereomeric or stereoisomeric form, or mixtures thereof, of a compound of the invention, which possess the useful properties described herein. It will be appreciated that certain compounds of the present invention contain an asymmetrically substituted carbon atom, and can be isolated in optically active or racemic forms. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. All chiral, diastereomeric, racemic forms and all geometric isomeric forms of a structure are intended, unless the specific stereochemistry or isomer form is specifically indicated.

Optically active forms of the compounds can be prepared using any method known in the art, including by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including simulated moving bed chromatography, is used in one embodiment. A wide variety of chiral stationary phases are commercially available.

II. Definitions

The following terms and abbreviations are used herein and defined as follows. The abbreviation:

"rt" as used herein means room temperature,
"h" as used herein means hour,
"DMAC" as used herein means dimethylacetamide,
"DMI" as used herein means 1,3-dimethyl-2-imidazolidinone,
"DMPU" as used herein means 1,3-dimethyl-3,4,5,6-tetrahydro-2 (1H)-pyrimidinone,
"DMSO" as used herein means dimethylsulfoxide,
"EDTA" as used herein means ethylenediaminetetraacetic acid,
"EtOAc" as used herein means ethylacetate,
"MTBE" as used herein means methyl t-butyl ether,
"NMP" as used herein means N-methylpyrrolidinone, and
"THF" as used herein means tetrahydrofuran.

As used herein, the term "substantially free of," "substantially in the absence of" or "isolated" refers to a nucleoside composition that includes at least 95%, and preferably 99% to 100% by weight, of the designated enantiomer of that nucleoside. In a preferred embodiment, the process produces compounds that are substantially free of enantiomers of the opposite configuration.

The term alkyl, as used herein, unless otherwise specified, refers to a saturated straight, branched, or cyclic, primary, secondary, or tertiary hydrocarbon, for example, of $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term aryl, as used herein, and unless otherwise specified, refers to phenyl, biphenyl, or naphthyl. The term includes both substituted and unsubstituted moieties. The aryl group can be substituted with one or more moieties selected from the group consisting of bromo, chloro, fluoro, iodo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "aralkyl," as used herein, and unless otherwise specified, refers to an aryl group as defined above linked to the molecule through an alkyl group as defined above. The term "alkaryl" or "alkylaryl" as used herein, and unless otherwise specified, refers to an alkyl group as defined above linked to the molecule through an aryl group as defined above. In each of these groups, the alkyl group can be optionally substituted as describe above and the aryl group can be optionally substituted with one or more moieties selected from the group consisting of alkyl, halo, haloalkyl, hydroxyl, carboxyl, acyl, acyloxy, amino, amido, azido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included within the scope of the term aryl are phenyl; naphthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-t-butylphenyl; 4-t-butylphenylmethyl and the like.

The term alkaryl or alkylaryl refers to an alkyl group with an aryl substituent. The term aralkyl or arylalkyl refers to an aryl group with an alkyl substituent.

The term "alkylamino" or "arylamino" refers to an amino group that has one or two alkyl or aryl substituents, respectively.

As used herein, "alkyl primary amine" is intended to have the meaning well known to one skilled in the art of organic chemistry. Examples of $C_3$–$C_6$ alkyl primary amine are propylamine, butylamine, pentylamine, and hexylamine, including both branched and straight-chain alkyl groups.

The term halo, as used herein, includes bromo, chloro, fluoro, and iodo.

The term heteroatom, as used herein, refers to oxygen, sulfur, nitrogen, and phosphorus.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "substituted", as used herein, means that one or more hydrogen on the designated atom is replaced with a selection from the indicated group, provided that the designated atom's normal valency is not exceeded, and that the substitution results in a stable compound.

The term purine or pyrimidine base includes, but is not limited to, adenine, $N^6$-alkyl-purines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^6$-alkylpurines, $N^2$-alkyl-6-thiopurines, thymine, cytosine, 5-fluoro-cytosine, 5-methylcytosine, 6-azapyrimidine, including 6-aza-cytosine, 2- and/or 4-mercapto-pyrmidine, uracil, 5-halouracil, including 5-fluorouracil, $C^5$-alkylpyrimidines, $C^5$-benzyl-pyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amido-pyrimidine, $C^5$-cyanopyrimidine, $C^5$-nitro-pyrimidine, $C^5$-amino-pyrimidine, $N^2$-alkyl-purines, $N^2$-alkyl-6-thiopurines, 5-azacytidinyl, 5-aza-uracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, 2-(Br, Fl, Cl or I)-purine optionally with a substituent including an amino or carbonyl group in the 6-position, and 6-(Br, Cl, or I)-purine optionally with a substituent including an amino or carbonyl group in the 2-position. Functional oxygen and nitrogen groups on the base can be protected as necessary or desired. Suitable protecting groups are well known to those skilled in the art, and include trimethylsilyl, dimethylhexylsilyl, t-butyldimethylsilyl, t-butyldiphenylsilyl, trityl, alkyl groups, and acyl groups such as acetyl and propionyl, methanesulfonyl, and p-toluenesulfonyl.

These purine and pyrimidine bases can be substituted with alkyl groups or aromatic rings, bonded through single or double bonds or fused to the heterocycle ring system. The purine base and pyrimidine bases can be bound to the sugar moiety through any available atom, including the ring nitrogen and ring carbon (producing a C-nucleoside).

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

In cases where compounds are sufficiently basic or acidic to form stable nontoxic acid or base salts, administration of the compound as a pharmaceutically acceptable salt can be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts can also be formed, including, sulfate, nitrate, bicarbonate, and carbonate salts.

Pharmaceutically acceptable salts can be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995)1–17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation."*AIDS Res. Hum. Retro Viruses.* 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hostetler, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. Nos. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995. Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

III. Detailed Description of Process Steps

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The reactions of the synthetic methods claimed herein are carried out in suitable solvents which can be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or in a combination of two of more solvents. Depending on the particular reaction step, suitable solvents for a particular reaction step can be selected by one skilled in the art.

Suitable ether solvents can include, by way of example and without limitation, tetrahydrofuran, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable ester solvents can include, by way of example and without limitation, methyl acetate, ethyl acetate, n-propyl acetate, 1-propyl acetate, n-butyl acetate, 1-butyl acetate, t-butyl acetate, n-amyl acetate, 1-amyl acetate, sec-amyl acetate, t-amyl acetate, 2,2-dimethylpropyl acetate, 2-methylbutyl acetate, methyl propionate, n-butyl propionate, ethyl butyrate, 1-propyl butyrate, methyl isobutyrate, ethyl isobutyrate, i-butyl isobutyrate, methyl valerate, ethyl valerate, methyl isovalerate, ethyl isovalerate, methyl pivalate, or ethyl pivalate.

Suitable polar aprotic solvents can include, by way of example and without limitation, tetrahydrofuran, dimethylformamide, dimethylacetamide, DMPU, DMI, NMP, formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable polar solvents can include, by way of example and without limitation, suitable polar aprotic solvents, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, 1-butyl alcohol, t-butyl alcohol, 2-ethoxyethanol, diethylene glycol, 1-,2-, or 3- pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluoroethane and hexafluoroethane.

As used herein, the term "suitable reducing agent" or "reducing agent" refers to any agent which reacts with 3'-O-acyl-2'-halo-2'-deoxycytidine and/or 2'-O-acyl-3'-halo-3'-deoxycytidine, wherein —O-acyl is —O—C(=O)CH$_2$R$^1$ as defined herein, to remove the —O— acyl- and halo groups and form a 2',3'-didehydro-2',3'-dideoxycytidine of Formula. Examples of reducing agents include, but are not limited to, Zn or Fe metals, or activated metals such as Zn—Cu.

As used herein, the term "suitable acid catalyst" or "acid catalyst" refers to any acidic agent such as a mineral acid or an organic acid such as a carboxylic acid, alkylsulfonic acid, or arylsulfonic acid, which catalyzes the reductive elimination of a 3-O-acyl-2'-halo-2'-deoxycytidine or 2-O-acyl-3'-halo-3'-deoxycytidine in the presence of a reducing agent to form a 2',3'-dideoxy-2',3'-didehydronucleoside. Examples of mineral acids include, but are not limited to hydroiodic acid, hydrobromic acid, hydrochloric acid, and sulfuric acid. Examples of organic acids include, but are not limited to methanesulfonic acid, p-toluene-sulfonic acid, trifluoromethane sulfonic acid, formic acid, acetic acid, trifluoroacetic acid, propionic acid, butyric acid, valeric acid, benzoic acid, and caproic acid.

As used herein, the term "suitable base" or "base" refers to any agent acting as a base which cleaves the 5'-O-acyl group of a compound of Formula (III) to form a free 5'-hydroxy group of a compound of Formula (IV). Examples of suitable bases include, but are not limited to, sodium hydroxide, lithium hydroxide, potassium carbonate, sodium carbonate, cesium carbonate, sodium methoxide, sodium ethoxide, lithium methoxide, lithium ethoxide, potassium methoxide, potassium ethoxide, ammonium hydroxide, ammonium $C_1$–$C_6$ alkoxide, $C_3$–$C_6$ alkyl primary amine, and basic resin. Examples of $C_3$–$C_6$ alkyl primary amine include, but are not limited to, propyl amine, butyl amine, and pentyl amine. Examples of "basic resin" include, but are not limited to, Dowex® 1X2-200 ion-exchange resin, Dowex® 1X2-400 ion-exchange resin, and Dowex® 1X4-50 ion-exchange resin. Dowex® is a registered trademark of Dow Chemical Company.

As used herein, the term "ammonium alkoxide" refers to a solution of ammonia dissolved in alcohol. Examples of ammonium $C_1$–$C_6$ alkoxide include, but are not limited to, ammonium methoxide (NH$_3$ in methanol), ammonium ethoxide (NH$_3$ in ethanol), ammonium propoxide (NH$_3$ in proanol), and ammonium butoxide (NH$_3$ in butanol).

As used herein, "amine base" refers to any nitrogen-containing compound which facilitates the formation of compound (VIII) from the 2',3'-dideoxy-2',3'-didehydrouridine compound (VII). Examples of amine bases include, but are not limited to, tertiary amines such as triethylamine, tributylamine, N-methylmorpholine, N,N-diisopropyl-ethylamine, tetramethylethylenediamine, N,N-dimethylcyclohexylamine, N,N-diethylcyclohexylamine, N,N-dimethyloctylamine, 1,4-diazabicyclo-[2.2.2]-octane, 1,8-diazabicyclo-[5.4.0]-undec-7-ene, 1,5-diazabicyclo-[4.3.0]-non-5-ene, and nitrogen-containing aromatic compounds such as pyridine and N,N-dimethyl-aminopyridine.

As used herein, "activating agent" refers to any agent that enables the conversion of the 5-fluoro-uridine ring of (VII) into a 5-fluoro-cytidine ring by converting the oxo group in the 4-position of the uridine ring into a suitable leaving group "LG", which in turn is displaced by an aminating agent to form the 5-fluoro-cytidine ring. Examples of an activating agent, in addition to agents known to one skilled in the art, include, but are not limited to, aryl sulfonyl halides, alkyl sulfonyl halides, and 1,2,4-triazole in the presence of a phosphorus chloride.

As used herein, "aryl sulfonyl halide" or "alkyl sulfonyl halide" refers to an aryl or alkyl substituted sulfonyl containing compound which reacts with the oxo of 2',3'-dideoxy-2',3'-didehydrouridine compound (VII), in the presence of an amine base, to form a compound of Formula (VIII) wherein "LG" is an alkylsulfonyloxy or an arylsulfonyloxy group. Examples of an aryl sulfonyl halide or alkyl sulfonyl halide include, but are not limited to, methanesulfonyl chloride, trifluoromethyl sulfonyl chloride, ethanesulfonyl chloride, benzenesulfonyl chloride, and p-toluenesulfonyl chloride.

As used herein, "phosphorus chloride" refers to a phosphorus containing compound which, in the presence of an amine base, and 1,2,4-triazole form a compound of Formula (VIII) wherein the leaving group "LG" is the triazolyl group. Examples of a phosphorus chloride compound include, but are not limited to, phosphorus oxychloride and diphenyl chlorophosphate.

It is understood by one skilled in the art that the leaving group or "LG" is dependent on which activating agent is used in the process. For example when methanesulfonyl chloride is the activating agent, then methanesulfonyloxy becomes the leaving group. Examples of the leaving group disclosed herein include, but are not limited to, methanesulfonyloxy, trifluoro-methane-sulfonyloxy, ethanesulfonyloxy, benzenesulfonyloxy, p-toluenesulfonyloxy, and 1,2,4-triazolyl.

As used herein, "aminating agent" refers to any nitrogen-containing compound which reacts with compound (VIII) to form a cytidine (IV). Examples of suitable aminating agents include, but are not limited to NH$_3$, ammonium hydroxide, and ammonium carbonate.

Combinations of substituents and/or variables are permissible only if such combinations result in stable compounds. By stable compound or stable structure it is meant herein a compound that is sufficiently robust to survive isolation to a useful degree of purity from a reaction mixture.

Step One—Preparation of Activated Material

The key starting material for this process is an appropriately substituted β-D- or β-L-nucleoside (1)

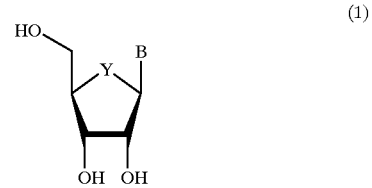

wherein B is a pyrimidine or purine base, including but not limited to, 5-fluorocytosine, 5-fluorouracil, cytosine, uracil, thymine, adenine, guanine, or inosine, and even more preferably 5-fluorocytosine or 5-fluorouracil; and Y is O, S or CH$_2$.

The β-D- or β-L-nucleoside can be purchased or can be prepared by any known means including standard sugar modifications and/or coupling techniques. In one embodiment, the β-D- or β-L-nucleoside is purchased.

The activation of the β-D- or β-L-nucleoside (1) can be achieved using a with an acyl halide of the formula X—C(=O)R', X—C(=O)C(R$^1$)$_2$OC(=O)R$^1$ or X—C(=O)phenylC(=O)OR$^1$; wherein X is a halogen (F, Cl, Br or I), and each R$^1$ is independently hydrogen, lower alkyl, alkyl, aryl or phenyl, in a compatible solvent at a suitable temperature to form the haloacylated product (2)

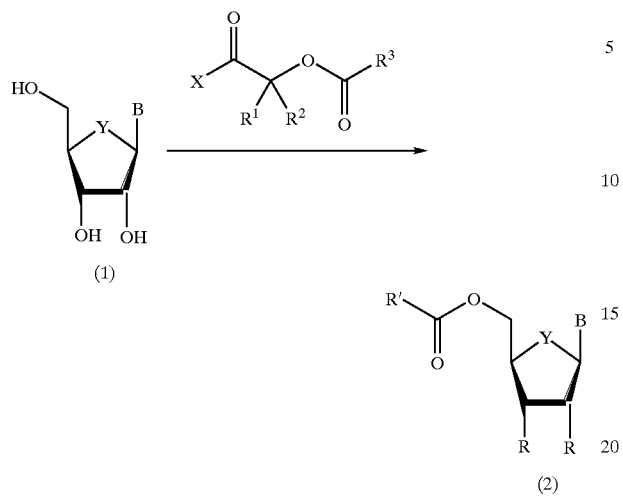

wherein R is $R^1$, —C($R^1$)$_2$OC(=O)$R^1$ or -phenylC(=O)O$R^1$; and at least one R is halogen (F, Cl, Br or I), and at least one R is an acyl of the formula —OC(=O)$R^1$.

This reaction can be accomplished at any temperature that allows the reaction to proceed at an acceptable rate without promoting decomposition or excessive side products. The preferred temperature is from about 0° C. to 85° C. and even more preferably from about 35° C. to 60° C.

Appropriate solvents include any polar aprotic solvent including, but not limiting to, alkyl solvents such as hexane and cyclohexane, benzene, toluene, acetone, ethyl acetate, dithianes, THF, dioxane, acetonitrile, dichloromethane, dichloroethane, diethyl ether, pyridine, dimethylformamide (DMF), dimethylsulfoxide (DMSO), dimethylacetamide, or any combination thereof, though preferably acetonitrile.

Step Two—Reduction of the Activated Material

The reduction of the haloacylated product (2) can be achieved using any suitable reducing agent, optionally with an acid catalyst, in a compatible solvent at a suitable temperature to form the 2',3'-dideoxy-2',3'-didehydro-nucleoside of structure (3).

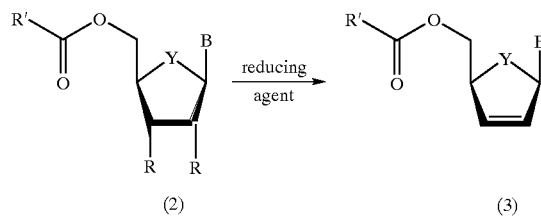

Suitable reducing agents include any reagent that can reductively dehalogenate the haloacylated product (2) to form a 2',3'-didehydro-2',3'-dideoxy-nucleoside of structure (3). Examples of reducing agents include, but are not limited to zinc or iron metals, or activated metals such as Zn—Cu.

Suitable acid catalysts include, but are not limited to, acetic acid, propionic acid, trifluoroacetic acid and hydrochloric acid, though most preferably acetic acid.

This reaction can be accomplished at any temperature that allows the reaction to proceed at an acceptable rate without promoting decomposition or excessive side products. The preferred temperature is from about 20° C. to 40° C. and even more preferably from about 25° C. to 35° C.

Appropriate solvents include any polar protic or aprotic solvent including, but not limiting to, alcohols, such as methanol, ethanol and isopropanol, acetone, ethyl acetate, dithianes, THF, dioxane, acetonitrile, dichloromethane, dichloroethane, diethyl ether, pyridine, dimethylformamide (DMF), dimethylsulfoxide (DMSO), dimethylacetamide, or any combination thereof, preferably a combination of methanol and ethyl acetate.

Step Three—Optional Modification of the Base and/or Deprotection

In one embodiment of the invention, the nucleoside of structure (3) is optionally further derivatized, for example by base modification or sugar modification by methods known in the art; and then optionally deprotecting the nucleoside if necessary.

In one embodiment, the β-D or β-L-2',3'-dideoxy-2',3'-didehydro-nucleoside can be converted into a β-D or β-L-2',3'-dideoxy-2',3'-didehydro-nucleoside bearing a different nucleobase. For example, a β-D or β-L-2',3'-dideoxy-2',3'-didehydro-5-fluorouridine can be derivatized to form a β-D or β-L-2',3'-dideoxy-2',3'-didehydro-5-fluorocytidine. Similarly a β-D or β-L-2',3'-dideoxy-2',3'-didehydro-uridine can be further derivatized to form a β-D or β-L-2',3'-dideoxy-2',3'-didehydro-cytidine. Alternatively, the β-D or β-L-2',3'-dideoxy-2',3'-didehydro-nucleoside can be reduced to form a β-D or β-L-2',3'-dideoxy and 2'- or 3'-deoxyribo-nucleoside analog. For example, hydrogen reduction can be effected in ethanol with 10% palladium on carbon. Alternatively, the D4 nucleoside can be modified to form a 2', a 3' or a 5'-substituted-nucleoside or a combination thereof, also using known chemistry to those skilled in the art. As a non-limiting illustrative example, Townsend, et al., *Chemistry of Nucleosides and Nucleotides*, Volume 1, Plenum Press: New York, teaches oxidation of 2'3'-dideoxy-2'3'-didehydro-nucleosides with osmium tetraoxide yields a ribonucleoside. Further functionalities can be introduced via the 2' or 3' hydroxyls using the teachings of Kuzuhara, H., et al., U.S. Pat. No. 5,144,018 (1992) by activating and substituting the relevant hydroxyl.

General Process from 5-Fluorocytidine

In one particular embodiment of the invention, the methods of the present invention, by way of example and without limitation, can be further understood by reference to Scheme 1. Scheme 1 provides the general synthetic method for the synthesis of compounds of formulae (II) through (IV) wherein Q is 2-($R^1CH_2C$(=O)O)phen-1-yl-, $R^1CH_2$—, or $R^1CH_2C$(=O)OC($R^2$)$_2$—; X is Cl, Br or I; $R^1$ is H or $C_1$–$C_6$ alkyl; $R^2$ is independently selected from methyl, ethyl, or propyl; $R^3$ is Cl, Br or I; and $R^4$ is $R^1CH_2C$(=O)O—.

It is to be understood that one skilled in the art of organic synthesis could follow the methods described or exemplified herein to prepare analogues of compounds of Formula (I), (II), (II*), and (III). It is the object of the present invention to provide a novel and improved process for the synthesis of β-D-D4FC which is useful as an antiviral agent which inhibits the growth or replication of HIV.

Scheme 1

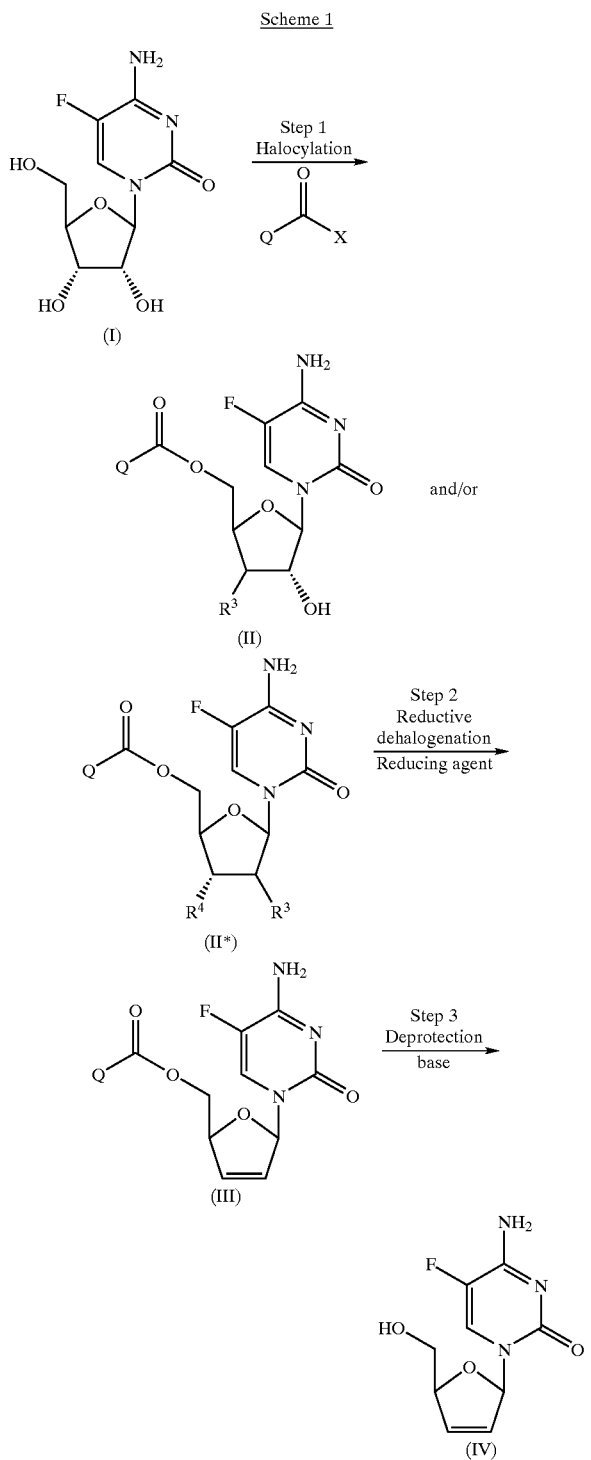

Step (1): Haloacylation of Cytidine (I).

As used herein, the term "haloacylation" refers to a reaction of an acyl halide QC(=O)X with a cytidine (I) to form 3'-O-acyl-2'-halo-2'-deoxycytidine (II*) and/or 2'-O-acyl-3'-halo-3'-deoxycytidine (II), wherein —O-acyl is —O—C(O)CH$_2$R'. An example is a bromoacetylation of fluorocytidine (I) with (AcO)(Me)$_2$C—C(O)Br to form a 3'-O-acetyl-2'-bromo-2'-deoxycytidine (II*-a) and 2'-O-acetyl-3'-bromo-3'-deoxycytidine (II-a). (See Scheme 2)

Step (1) is conducted by reacting a cytidine of Formula (I) with an acyl halide of Formula Q(C=O)X in one or more suitable aprotic solvent(s) to form a compound of Formula (II), a compound of (II*), or a mixture of compounds of Formula (II) and (II*). By way of general guidance, a cytidine of Formula (I) is charged to a reaction vessel followed by addition of a suitable polar aprotic solvent(s). A suitable acyl halide of Formula Q(C=O)X, such as 2-acetoxy-2-methyl-propionyl bromide, is then charged to the vessel. After reaction is complete, the temperature of reaction is cooled to a range of about −10 to about 25° C. Then the reaction is quenched by the addition of an aqueous base solution, such as aqueous alkaline hydroxide, carbonate or bicarbonate solution. The pH of the reaction mixture should be closely monitored during quenching, so that the pH is between 7 to 11 upon completion of addition of the aqueous base solution. Subsequently, intermediates (II) and/or (II*) are extracted into an organic solvent such as a halogenated hydrocarbon solvent or an ester solvent. The preferred organic solvent for extracting intermediates (II) and/or (II*) is an ester solvent. Optionally, intermediates (II) and/or (II*) can be carried forward as a solution stream into the next step without isolation as a solid.

The reaction is monitored by HPLC, and is considered complete when the starting material peak for compound (I) reaches <5% by area and/or the product peaks reach >70% by area. Depending on the amount of the acyl halide used and the temperature of the reaction, reaction time ranges from about 4 to about 48 hours.

Suitable polar aprotic solvents include alkylnitriles, esters, halogenated hydrocarbons, ethers, dialkylformamides, or a combination of two or more suitable polar aprotic solvents. Preferred suitable polar aprotic solvents for step (1) include, but are not limited to, acetonitrile, ethyl acetate and methylene chloride. More preferred is a combination of two or more polar aprotic solvents, preferably ethyl acetate and acetonitrile. A preferred ratio of ethyl acetate to acetonitrile for step (1) is between 20:1 to 1:1. A more preferred ratio of ethyl acetate to acetonitrile is between 10:1 to 2:1. A most preferred ratio is 4:1 (EtOAc:CH$_3$CN).

Suitable acyl halides include, but are not limited to, 2-acetoxy-2-methyl-propionyl chloride, 2-acetoxy-2-methyl-propionyl bromide, 2-acetoxy-2-methyl-propionyl iodide, 2-methyl-2-(1-oxopropoxy)-propanoyl chloride, 2-methyl-2-(1-oxopropoxy)-propanoyl bromide, 2-methyl-2-(1-oxopropoxy)-propanoyl iodide, 2-chloro-1,1-dimethyl-2-oxoethyl ester butanoic acid, 2-bromo-1,1-dimethyl-2-oxoethyl ester butanoic acid, 2-iodo-1,1-dimethyl-2-oxoethyl ester butanoic acid, 2-chloro-1,1-dimethyl-2-oxoethyl ester pentanoic acid, 2-bromo-1,1-dimethyl-2-oxoethyl ester pentanoic acid, 2-iodo-1,1-dimethyl-2-oxoethyl ester pentanoic acid, 2-(acetoxy)-2-ethyl-butanoyl chloride, 2-(acetoxy)-2-ethyl-butanoyl bromide, 2-(acetoxy)-2-ethyl-butanoyl iodide, 2-(acetoxy)-2-methyl-butanoyl chloride, 2-(acetoxy)-2-methyl-butanoyl bromide, 2-(acetoxy)-2-methyl-butanoyl iodide, 2-(acetoxy)-2-methyl-pentanoyl chloride, 2-(acetoxy)-2-methyl-pentanoyl bromide, or 2-(acetoxy)-2-methyl-pentanoyl iodide. More preferred suitable acyl halides include, but are not limited to, 2-acetoxy-2-methyl-propionyl bromide, 2-(acetoxy)-2-methyl-butanoyl bromide, 2-(acetoxy)-2-ethyl-butanoyl bromide, or 2-(acetoxy)-2-methyl-pentanoyl bromide. A most preferred suitable acyl halide is 2-acetoxy-2-methyl-propionyl bromide.

A preferred amount of the suitable acyl halide is about 2.0 to about 8.0 equivalents based on one mole of the starting material 5-fluorocytidine. A more preferred amount of acyl halide for step (1) is about 3.0 to about 5.0 equivalents.

It is preferred to add the suitable acyl halide to the reaction vessel in about 0.5 hours to about 4 hours. A more preferred addition time of acyl halide for step (1) is about 0.5 to about 3 hours, and a most preferred addition time is about 1 hour.

A suitable temperature range for the addition of a suitable acyl halide of Step (1) is about 0° C. to about 60° C. A preferred suitable temperature range for the addition of a suitable acyl halide of step (1) is about 10° C. to about 40° C., and most preferred suitable temperature range is about 25° C. to about 40° C.

A preferred aqueous base solution is an aqueous solution of NaOH, potassium carbonate or potassium bicarbonate.

A preferred pH range for the reaction is from about 7.5 to about 10 upon completion of addition of the aqueous base. A most preferred pH range is in the range of about 8 to about 9.

It is understood that the presence of a tetrahaloammonium salt can facilitate this reaction depending on the specific cytidine and acyl halide.

It is understood that one skilled in the art can determine the preferred reaction time of step (1) as dependent on temperature, acyl halide, and suitable polar aprotic solvent. Generally, under the preferred conditions, the reaction time is from about 15 to about 24 hours.

The progress of reaction in Step (1) was monitored by HPLC using the following method:

| HPLC CONDITION | |
|---|---|
| Column: | Eclipse XDB-C18, 25 cm × 4.6 mm I.D. |
| Mobile phase: | A: HPLC grade Acetonitrile |
| | B: HPLC grade water |
| Gradient: | t = 0 min    97% A    3% B |
| | t = 10 min   97% A    3% B |
| | t = 25 min   50% A    50% B |
| | t = 30 min   50% A    50% B |
| Flow rate: | 1.0 mL/min |
| Injection volume: | 5 microliters |
| Stop Time: | 30 minutes |
| Post Time: | 5 minutes |
| Oven Temperature: | 40° C. |
| Detector: | UV (220 nm) |

Sample preparation: dissolve 25 mg of sample (dry solids weight) into a suitable solvent; adjust concentration to approximately 1 mg/ml. The sample concentration can be adjusted to ensure the proper quantitation.

The same HPLC method is also used to monitor reaction progress in Step (2) and Step (3).

Step (2): Reductive Dehalogenation.

This step comprises adding a suitable reducing agent to intermediates (II) and/or (II*) from step (1) in one or more suitable polar solvent(s), optionally in the presence of a suitable acid catalyst, to form a compound of Formula (III). By way of general guidance, compound (II), compound (II*), or a mixture of compounds (II) and/or (II*), from Step (1) is charged (as a solution or as solids) in a reaction vessel followed by addition of a suitable polar solvent at room temperature. A suitable reducing agent such as Zn—Cu activated metal is then added to the vessel. Conditions which can facilitate the reductive elimination include the addition of an acid catalyst, such as a mineral acid or an organic acid. Preferably an acid catalyst is charged to a well-agitated mixture of the solution of compounds (II) and/or (II*) and the reducing agent over a period of about 0.5 h to about 1 hour.

The reaction is monitored by HPLC (see HPLC condition in Step (1)) and is considered complete when the starting material peak for (II) and/or (II*) is <5% by area. Depending on the reducing agent used and the temperature of the reaction, completion can be reached in about 0.2 h to about 48 hours. Under the preferred conditions, the reaction is complete in about 4 to about 12 hours.

The reducing agent, for example Zn—Cu activated metal, which can be in excess, is then removed by filtration, and the solvent is removed under reduced pressure. The crude product (III) is then dissolved in an ester solvent such as ethyl acetate or isopropyl acetate. A metal complexing reagent is added to the crude product solution. The metal complexing reagent forms a solid with the metal salts which can be removed by filtration. The filtrate containing compound (III) is then washed with an aqueous solution such as aqueous ammonium and aqueous EDTA. The compound 2',3'-dideoxy-2',3'-didehydrocytidine (III) can be obtained by removing the solvent. The residue is then dissolve in an alcohol solvent to form a solution which is used in Step (3). A preferred alcohol solvent is methanol or ethanol. A most preferred alcohol solvent is methanol.

Suitable polar solvents for step (2) are dialkyl-formamide, dialkylacetamide, alcohol, alkylnitrile, ether, ester, or a combination of two or more of the suitable polar solvents. Preferred suitable polar solvents are DMF, methanol, ethanol, acetonitrile, tetrahydrofuran, 1,4-dioxane, ethyl acetate, or a combination of two or more of the suitable polar solvents. A most preferred solvent is one consisting of ethyl acetate and methanol. Preferred ratio of ethyl acetate to methanol for step (2) is between 4:1 to 1:1. Most preferred ratio is from 4:1 to 2:1.

Reducing agents include, but are limited to, metals such as Zn or Fe, or activated metals such as Zn—Cu couple. Preferred suitable reducing agents for step (2) are Zn and Zn—Cu couple. A most preferred suitable reducing agent is Zn—Cu couple. When Zn—Cu couple is used, the molar ratio of Zn and Cu can be between 99:1 to 1:1. Preferred molar ratio is between 99:1 to 10:1. Most preferred ratio is between 99:1 to 25:1. The preferred amount of a reducing agent is from 1.2 to 20 equivalents. Most preferred amount is from 1.5 to 3.0 equivalents.

Preferred suitable acid catalysts for step (2) include, but are not limited to, acetic acid, propionic acid, trifluoroacetic acid, and hydrochloric acid. A most preferred suitable acid is acetic acid.

A preferred amount of suitable acid catalyst for step (2) is 0.05 to 2.0 equivalents per mole of compounds (II) and/or (II*). A most preferred amount of suitable acid catalyst is from 0.05 to 0.5 equivalents.

A preferred temperature for step (2) is from about 20 to about 40° C. A most preferred temperature is from 25 to 35° C.

Suitable metal complexing reagents include potassium carbonate, sodium carbonate, and sodium sulfide. The preferred metal complexing reagent is potassium carbonate.

Step 3: Deprotection.

This step comprises adding a suitable base to 2',3'-dideoxy-2',3'-didehydro-nucleoside (III) in a suitable solvent to form a compound of Formula (IV). By way of general guidance, compound (III) is charged to the reaction vessel in a suitable solvent followed by addition of a suitable base at 20 to 50° C.

The reaction is monitored by HPLC (see HPLC condition in Step (1)), and is considered complete when the starting material peak for (III) reaches <5% by area. Depending upon the base and solvent used, the reaction is usually complete in about 1 hour to about 48 hours. Using the preferred conditions, the reaction is usually complete in about 4 to about 18 hours.

Solvents for step (3) include alcohols, aqueous alcohols, or aqueous ethers. Preferred solvents for step (3) include, but are not limited to, methyl alcohol, ethyl alcohol, aqueous methyl alcohol, aqueous ethyl alcohol, aqueous THF, methyl alcohol-THF, or a combination of two or more of the above solvents. A most preferred solvent is methyl alcohol.

Compound (IV) can be obtained by removing the solvent followed by crystallization using an alcohol solvent such as methanol or ethanol. Alternatively, and more preferably, compound (IV) is obtained by precipitation/or crystallization upon partial removal of solvent. The crude product, compound (IV), obtained by a filtration, is then (re)crystallized in an alcohol solvent such as methanol or ethanol.

Suitable bases for the deprotection in step (3) include alkaline hydroxides, alkaline carbonates, alkaline alkoxides, basic resin, ammonium hydroxide, ammonium $C_1$–$C_6$ alkoxide, and $C_3$–$C_6$ alkyl primary amines. A preferred suitable base for step (3) includes, but is not limited to, sodium hydroxide, potassium hydroxide, potassium carbonate, sodium methoxide, sodium ethoxide, ammonium hydroxide, ammonium methoxide, ammonium ethoxide, and ammonium propoxide. Most preferred bases are sodium methoxide, ammonium hydroxide, and ammonium methoxide.

A preferred amount of base is from 0.02 to 20 equivalents of a compound of Formula (III). A more preferred amount is from 0.05 to 1.2 equivalents. A most preferred amount is 0.05 equivalents.

A most preferred reaction temperature is from about 25 to about 35° C.

It is understood that one skilled in the art can determine the preferred reaction time of step (1) as dependent on temperature, suitable base, and solvent. Generally, under the preferred conditions, the reaction time is from 4 to 18 hours.

The process represented in Scheme 2, which is meant to be illustrative of the present invention and is not meant to be construed as limiting the invention's scope. One skilled in the art understands that other minor products, such as (II-b), (II*-b) and (III-b), can also be generated by the reactions of the present invention.

Scheme 2

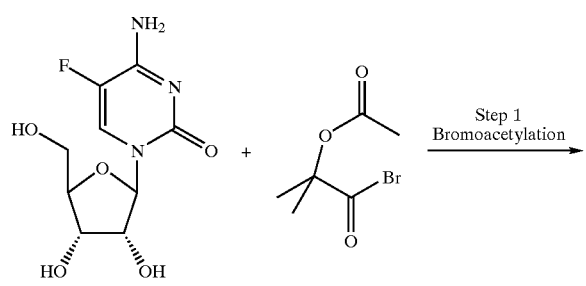

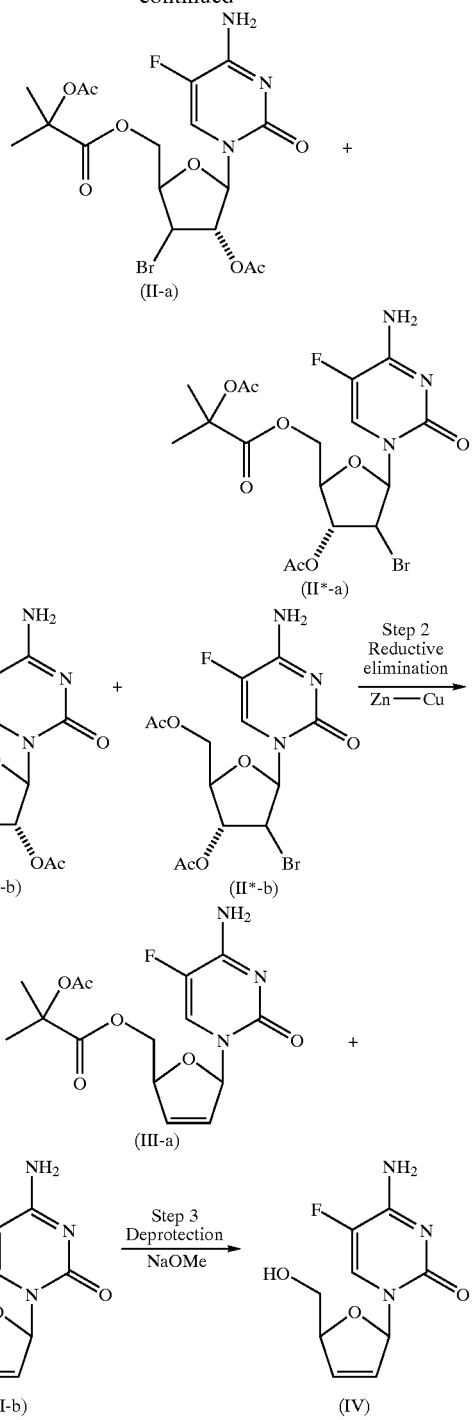

General Process from 5-Fluorouridine

In another particular embodiment of the present invention, the methods of the present invention, by way of example and without limitation, can be further understood by reference to Scheme 3. Scheme 3 provides the general synthetic method for the synthesis of compounds of formulae (II) through (IV) wherein Q is 2-$R^1CH_2C$(—O)O-phen-1-yl-, $R^1CH_2$—, or $R^1CH_2C$(=O)OC($R^1$)$_2$—; X is Cl, Br, or I; $R^1$ is H or $C_1$–$C_6$ alkyl; $R^2$ is independently selected from methyl, ethyl, or propyl; $R^3$ is Cl, Br, or I; and $R^4$ is $R^1CH_2C$(=O)O—.

It is to be understood that one skilled in the art of organic synthesis could follow the methods described or exemplified herein to prepare analogues of compounds of Formula (II), (II*), (III), and (IV). It is the object of the present invention to provide a novel and improved process for the synthesis of β-D-D4FC which is useful as an antiviral agent which inhibits the growth or replication of HIV.

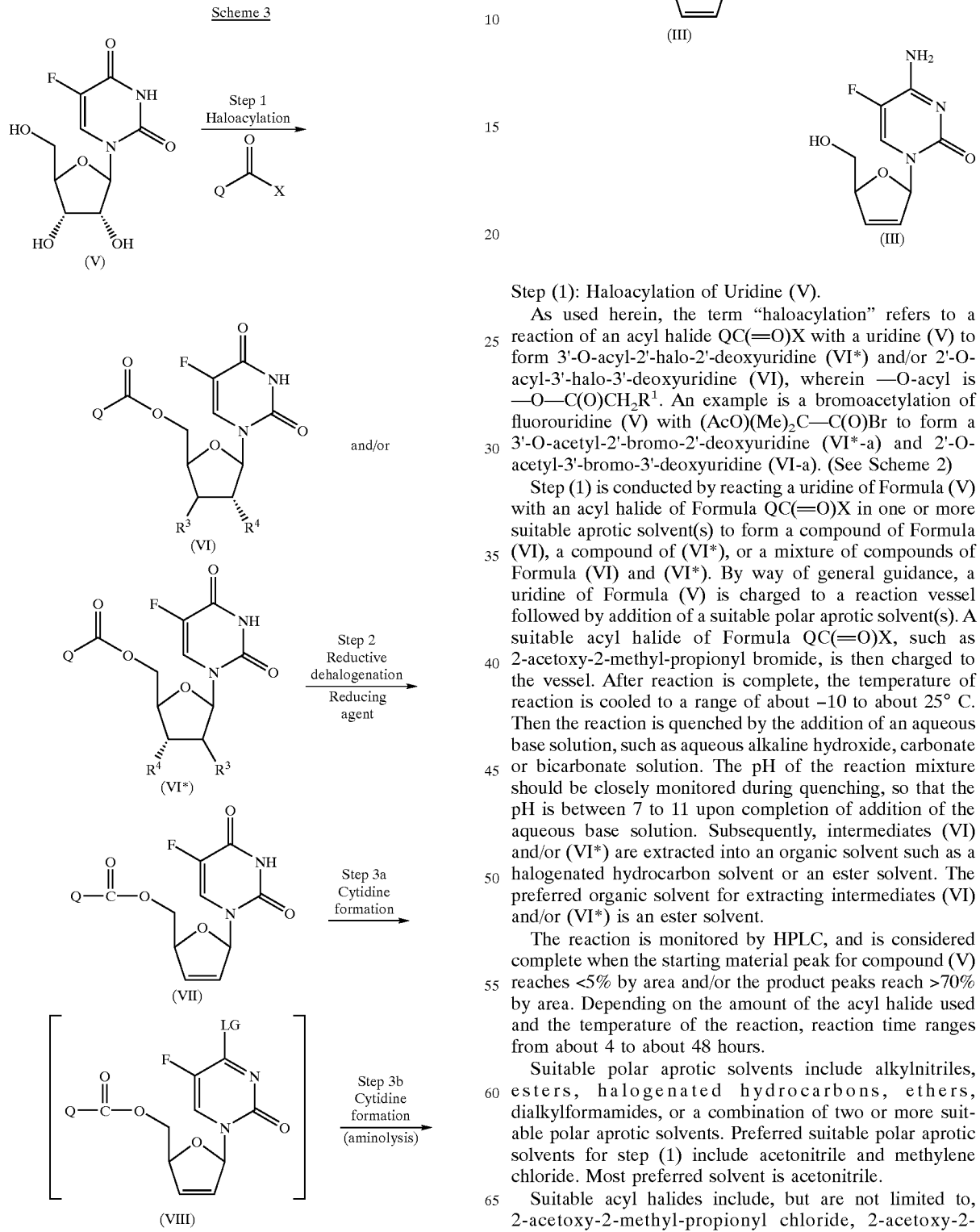

Step (1): Haloacylation of Uridine (V).

As used herein, the term "haloacylation" refers to a reaction of an acyl halide QC(=O)X with a uridine (V) to form 3'-O-acyl-2'-halo-2'-deoxyuridine (VI*) and/or 2'-O-acyl-3'-halo-3'-deoxyuridine (VI), wherein —O-acyl is —O—C(O)CH$_2$R$^1$. An example is a bromoacetylation of fluorouridine (V) with (AcO)(Me)$_2$C—C(O)Br to form a 3'-O-acetyl-2'-bromo-2'-deoxyuridine (VI*-a) and 2'-O-acetyl-3'-bromo-3'-deoxyuridine (VI-a). (See Scheme 2)

Step (1) is conducted by reacting a uridine of Formula (V) with an acyl halide of Formula QC(=O)X in one or more suitable aprotic solvent(s) to form a compound of Formula (VI), a compound of (VI*), or a mixture of compounds of Formula (VI) and (VI*). By way of general guidance, a uridine of Formula (V) is charged to a reaction vessel followed by addition of a suitable polar aprotic solvent(s). A suitable acyl halide of Formula QC(=O)X, such as 2-acetoxy-2-methyl-propionyl bromide, is then charged to the vessel. After reaction is complete, the temperature of reaction is cooled to a range of about −10 to about 25° C. Then the reaction is quenched by the addition of an aqueous base solution, such as aqueous alkaline hydroxide, carbonate or bicarbonate solution. The pH of the reaction mixture should be closely monitored during quenching, so that the pH is between 7 to 11 upon completion of addition of the aqueous base solution. Subsequently, intermediates (VI) and/or (VI*) are extracted into an organic solvent such as a halogenated hydrocarbon solvent or an ester solvent. The preferred organic solvent for extracting intermediates (VI) and/or (VI*) is an ester solvent.

The reaction is monitored by HPLC, and is considered complete when the starting material peak for compound (V) reaches <5% by area and/or the product peaks reach >70% by area. Depending on the amount of the acyl halide used and the temperature of the reaction, reaction time ranges from about 4 to about 48 hours.

Suitable polar aprotic solvents include alkylnitriles, esters, halogenated hydrocarbons, ethers, dialkylformamides, or a combination of two or more suitable polar aprotic solvents. Preferred suitable polar aprotic solvents for step (1) include acetonitrile and methylene chloride. Most preferred solvent is acetonitrile.

Suitable acyl halides include, but are not limited to, 2-acetoxy-2-methyl-propionyl chloride, 2-acetoxy-2-methyl-propionyl bromide, 2-acetoxy-2-methyl-propionyl iodide, 2-methyl-2-(1-oxopropoxy)-propanoyl chloride, 2-methyl-2-(1-oxo-propoxy)-propanoyl bromide, 2-methyl-2-(1-oxopropoxy)-propanoyl iodide, 2-chloro-1,1-dimethyl-2-oxoethyl ester butanoic acid, 2-bromo-1,1-dimethyl-2-oxoethyl ester butanoic acid, 2-iodo-1,1-dimethyl-2-oxoethyl ester butanoic acid, 2-chloro-1,1-dimethyl-2-oxoethyl ester pentanoic acid, 2-bromo-1,1-dimethyl-2-oxoethyl ester pentanoic acid, 2-iodo-1,1-dimethyl-2-oxoethyl ester pentanoic acid, 2-(acetoxy)-2-ethyl-butanoyl chloride, 2-(acetoxy)-2-ethyl-butanoyl bromide, 2-(acetoxy)-2-ethyl-butanoyl iodide, 2-(acetoxy)-2-methyl-butanoyl chloride, 2-(acetoxy)-2-methyl-butanoyl bromide, 2-(acetoxy)-2-methyl-butanoyl iodide, 2-(acetoxy)-2-methyl-pentanoyl chloride, 2-(acetoxy)-2-methyl-pentanoyl bromide, or 2-(acetoxy)-2-methyl-pentanoyl iodide. More preferred acyl halides include, but are not limited to, 2-acetoxy-2-methyl-propionyl bromide, 2-(acetoxy)-2-methyl-butanoyl bromide, 2-(acetoxy)-2-ethyl-butanoyl bromide, or 2-(acetoxy)-2-methyl-pentanoyl bromide. A most preferred acyl halide is 2-acetoxy-2-methyl-propionyl bromide.

A preferred amount of the acyl halide is about 2.0 to about 8.0 equivalents based on one mole of the starting material 5-fluorouridine. A more preferred amount of acyl halide for step (1) is about 3.0 to about 5.0 equivalents.

It is preferred to add the acyl halide to the reaction vessel in about 0.5 hours to about 4 hours. A more preferred addition time of acyl halide for step (1) is about 0.5 to about 3 hours, and a most preferred addition time is about 1 hour.

A suitable temperature range for the addition of an acyl halide of Step (1) is about 0° C. to about 60° C. A preferred temperature range for the addition of an acyl halide of step (1) is about 10° C. to about 85° C., and most preferred temperature range is about 35° C. to about 60° C.

A preferred aqueous base solution is an aqueous solution of NaOH, potassium carbonate or potassium bicarbonate.

A preferred pH range for the reaction is from about 7.5 to about 10 upon completion of addition of the aqueous base. A most preferred pH range is in the range of about 8 to about 9.

It is understood that the presence of a tetrahaloammonium salt can facilitate this reaction depending on the specific uridine and acyl halide.

It is understood that one skilled in the art can determine the preferred reaction time of step (1) as dependent on temperature, acyl halide, and suitable polar aprotic solvent. Generally, under the preferred conditions, the reaction time is from about 15 to about 24 hours.

Step (2): Reductive Dehalogenation.

This step comprises adding a reducing agent to intermediates (VI) and/or (VI*) from step (1) in one or more suitable polar solvent(s), optionally in the presence of an acid catalyst, to form a compound of Formula (VII). By way of general guidance, compound (VI), compound (VI*), or a mixture of compounds (VI) and/or (VI*), from Step (1) is charged (as a solution or as solids) in a reaction vessel followed by addition of a suitable polar solvent at room temperature. A suitable reducing agent, such as Zn—Cu activated metal, is then added to the vessel. Conditions which can facilitate the reductive elimination include the addition of an acid catalyst, such as a mineral acid or an organic acid. Preferably an acid catalyst is charged to a well-agitated mixture of the solution of compounds (VI) and/or (VI*) and the reducing agent over a period of about 0.5 h to about 1 hour.

The reaction is monitored by HPLC (see HPLC condition in Step (1)) and is considered complete when the starting material peak for (VI) and/or (VI*) is <5% by area. Depending on the reducing agent used and the temperature of the reaction, completion can be reached in about 0.2 h to about 48 hours. Under the preferred conditions, the reaction is complete in about 4 to about 12 hours.

The reducing agent, for example Zn—Cu activated metal, which can be in excess, is then removed by filtration, and the solvent is removed under reduced pressure. The crude product (VII) is then dissolved in an ester solvent such as ethyl acetate or isopropyl acetate. A metal complexing reagent is added to the crude product solution. The metal complexing reagent forms a solid with the metal salts which can be removed by filtration. The filtrate containing compound (VII) is then washed with an aqueous solution such as aqueous ammonium and aqueous EDTA. The compound 2',3'-dideoxy-2',3'-didehydrouridine (VII) can be obtained by removing the solvent.

Suitable polar solvents for step (2) are dialkyl-formamide, dialkylacetamide, alcohol, alkylnitrile, ether, ester, or a combination of two or more of the suitable polar solvents. Preferred suitable polar solvents are DMF, methanol, ethanol, acetonitrile, tetrahydrofuran, 1,4-dioxane, ethyl acetate, or a combination of two or more of the suitable polar solvents. A most preferred solvent is one consisting of ethyl acetate and methanol. Preferred ratio of ethyl acetate to methanol for step (2) is between 4:1 to 1:1. Most preferred ratio is from 4:1 to 2:1.

Reducing agents include, but are limited to, metals such as Zn or Fe, or activated metals such as Zn—Cu couple. Preferred reducing agents for step (2) are Zn and Zn—Cu couple. A most preferred reducing agent is Zn—Cu couple. When Zn—Cu couple is used, the molar ratio of Zn and Cu can be between 99:1 to 1:1. Preferred molar ratio is between 99:1 to 10:1. Most preferred ratio is between 99:1 to 25:1. The preferred amount of a reducing agent is from 1.2 to 20 equivalents. Most preferred amount is from 1.5 to 3.0 equivalents.

Preferred acid catalysts for step (2) include, but are not limited to, acetic acid, propionic acid, trifluoroacetic acid, and hydrochloric acid. A most preferred acid is acetic acid.

A preferred amount of acid catalyst for step (2) is 0.05 to 2.0 equivalents per mole of compounds (VI) and/or (VI*). A most preferred amount of acid catalyst is from 0.05 to 0.5 equivalents.

A preferred room temperature for step (2) is from about 20 to about 40° C. A most preferred temperature is from 25 to 35° C.

Suitable metal complexing reagents include potassium carbonate, sodium carbonate, and sodium sulfide. The preferred metal complexing reagent is potassium carbonate.

Step (3-a, b): Cytidine Formation

In this step, the oxo group at the 4-position of the 5-fluoro-uridine moiety of compound (VII) is first converted to a suitable leaving group, Step (3-a), followed by an aminolysis reaction, Step (3-b), to form a 5-fluorocytidine (III).

Step (3-a). This step comprises adding intermediate (VII) from Step (2) to a suitable activating agent in the presence of a suitable amine base in a suitable solvent to form a compound of Formula (VIII). By way of general guidance, a suitable activating agent is prepared in a reaction vessel in a suitable solvent in the presence of an amine base. It is understood that part of the preparation can include workup of the solution, for example filtration, before addition of Compound (VII). Compound (VII) is added to the vessel and the reaction is aged for a sufficient amount of time to form an intermediate of formula (VIII). The reaction is carried forward into Step (3-b).

Suitable solvents for Step (3-a) include, but are not limited to, halogenated hydrocarbons, ethers or nitriles, wherein nitriles are preferred, of which acetonitrile is most preferred.

Suitable amine bases for Step (3-a) are tertiary amines, examples of which include, triethylamine, tributylamine, N-methylmorpholine, N,N-diisopropyl-ethylamine, N,N-dimethylcyclohexylamine, N,N-diethylcyclohexylamine, N,N-dimethyloctylamine, tetramethylethylenediamine, pyridine, N,N-dimethyl-aminopyridine, 1,4-diazabicyclo-[2.2.2]-octane, 1,8-diazabicyclo[5.4.0]undec-7-ene, and 1,5-diazabicyclo-[4.3.0]-non-5-ene. Preferred are triethylamine, tributylamine, N-methylmorpholine, N,N-diisopropyl-ethylamine, pyridine, 1,4-diazabicyclo-[2.2.2]-octane, 1,8-diazabicyclo-[5.4.0]-undec-7-ene, tetramethylethylenediamine, and N,N-dimethyl-aminopyridine. A more preferred amine base is a trialkylamine, wherein triethylamine is preferred.

Suitable activating agents for Step (3-a) are arylsulfonyl chlorides, alkylsulfonyl chlorides and 1,2,4-triazole with phosphorus chlorides; wherein 1,2,4-triazole with phosphorus chlorides are preferred. Phosphorus chloride includes phosphorus oxychloride, diaryl chlorophosphates and dialkyl chlorophosphates. A preferred phosphorus chloride is phosphorus oxychloride or diaryl chlorophosphate. A most preferred phosphorus chloride is phosphorus oxychloride or diphenyl chlorophosphate.

In a general example of Step (3-a) a vessel is charged with 1,2,4-triazole in a suitable solvent, and a suitable amine base is added followed by addition of a phosphorus chloride. Preferred temperatures are from −40 to 40° C.; most preferred temperatures are from −10 to 5° C. After addition of the phosphorus chloride, the mixture is agitated at room temperature preferably for 15 minutes to 4 hours, most preferably for 0.50 to 1 hours, after which the reaction is filtered. After filtration, compound (VII) is added to the filtrate and the reaction mixture is stirred at room temperature. Depending on the amounts of the phosphorus chloride and 1,2,4-triazole used, reaction time ranges from 1 to 48 hours. A preferred amount of a phosphorus chloride is 2 to 8 equivalents based on one mole of compound (VII). A more preferred amount of a phosphorus chloride is 3.0 to 5.0 equivalents. The amounts of 1,2,4-triazole and the base depend on the amount of the phosphorus chloride and the number of chloride in the phosphorus chloride (n). Preferred amounts of 1,2,4-triazole and the base are 1.0 to n to 1.2 to n equivalents based on one mole of the phosphorus chloride. Most preferred amounts of 1,2,4-triazole and the base are 1.0 to n to 1.05 to n equivalents.

Step (3-b). This step comprises adding an aminating agent to the solution from Step (3-a) to form a compound of Formula (III). Preferred aminating agents are sources of ammonia, such as, ammonia gas, ammonium hydroxide and ammonium salt such as ammonium carbonate; wherein ammonia gas and ammonium hydroxide are more preferred.

Ammonia from a suitable ammonia source is then directly introduced into the above solution at a temperature from 0 to 40° C., preferably from 10 to 25° C. A preferred amount of ammonia is 2.0 to 30.0 equivalents based on one mole of the starting material. Most preferred amount of ammonia is 2.0 to 10.0 equivalents. Depending on the amount of ammonia used, the reaction time ranges from 30 minutes to 24 hours.

The product is obtained by removing the solvent followed by chromatography or recrystalization in solvents such as esters, ethers, hydrocarbons, halogenated hydrocarbons; preferably in esters; most preferably in ethyl acetate.

Step 3-c: Deprotection.

This step comprises adding a suitable base to 2',3'-dideoxy-2',3'-didehydro-nucleoside (III) in a suitable solvent to form a compound of Formula (III). By way of general guidance, compound (III) is charged to the reaction vessel in a suitable solvent followed by addition of a suitable base at 20 to 50° C.

The reaction is monitored by HPLC (see HPLC condition in Step (1)), and is considered complete when the starting material peak for (III) reaches <5% by area. Depending upon the base and solvent used, the reaction is usually complete in about 1 hour to about 48 hours. Using the preferred conditions, the reaction is usually complete in about 4 to about 18 hours.

Solvents for step (3-c) include alcohols, aqueous alcohols, or aqueous ethers. Preferred solvents for step (3-c) include, but are not limited to, methyl alcohol, ethyl alcohol, aqueous methyl alcohol, aqueous ethyl alcohol, aqueous THF, methyl alcohol-THF, or a combination of two or more of the above solvents. A most preferred solvent is methyl alcohol.

Compound (III) can be obtained by removing the solvent followed by crystallization using an alcohol solvent such as methanol or ethanol. Alternatively, and more preferably, compound (III) is obtained by precipitation/or crystallization upon partial removal of solvent. The crude product, compound (III), obtained by a filtration, is then (re)crystallized in an alcohol solvent such as methanol or ethanol.

Suitable bases for the deprotection in step (3-c) include alkaline hydroxides, alkaline carbonates, alkaline alkoxides, basic resin, ammonium hydroxide, ammonium $C_1$–$C_6$ alkoxide, and $C_3$–$C_6$ alkyl primary amines. A preferred suitable base for step (3-c) includes, but is not limited to, sodium hydroxide, potassium hydroxide, potassium carbonate, sodium methoxide, sodium ethoxide, ammonium hydroxide, ammonium methoxide, ammonium ethoxide, and ammonium propoxide. Most preferred bases are sodium methoxide, ammonium hydroxide, and ammonium methoxide.

A preferred amount of base is from 0.02 to 20 equivalents of a compound of Formula (III). A more preferred amount is from 0.05 to 1.2 equivalents. A most preferred amount is 0.05 equivalents.

A most preferred reaction temperature is from about 25° C. to about 35° C.

It is understood that one skilled in the art can determine the preferred reaction time of step (3-c) as dependent on temperature, suitable base, and solvent. Generally, under the preferred conditions, the reaction time is from 4 to 18 hours.

The process represented in Scheme 4 is meant to be illustrative of the present invention and is not meant to be construed as limiting the invention's scope. One skilled in the art understands that other minor products, such as (VI-b), (VI*-b), (VII-b), and (III-b) can also be generated by the reactions of the present invention.

Scheme 4

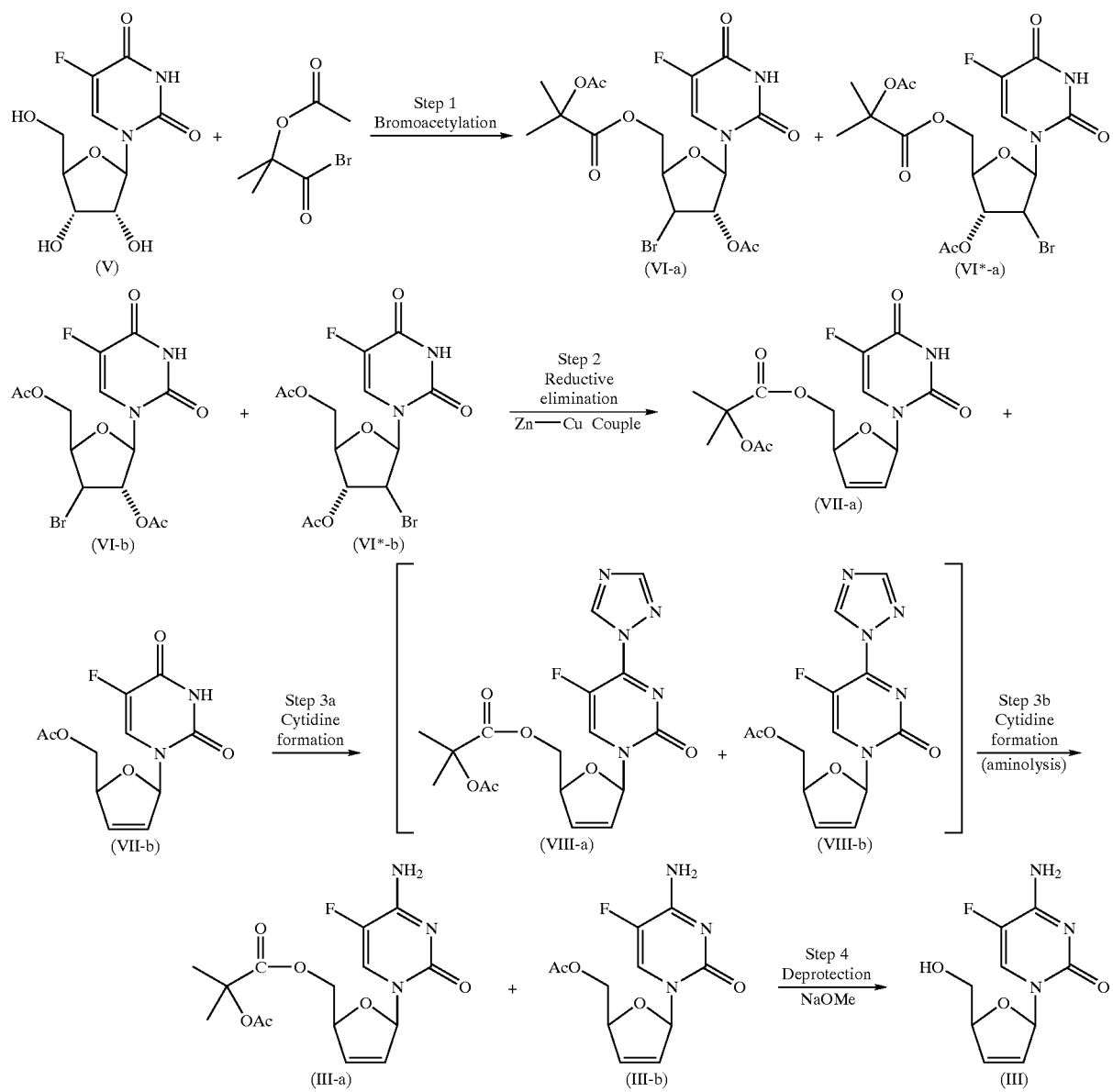

HPLC Conditions:

The progress of reaction in Steps (1), (2), (3), and (4) were monitored by HPLC using the following method:

| | |
|---|---|
| Column: | Eclipse XDB-C18, 25 cm × 4.6 mm I.D. |
| Mobile phase: | A: 10 mM $NaH_2PO_4$ pH 3.6 buffer |
| | B: HPLC grade acetonitrile |
| Gradient: | t = 0 min    83% A   17% B |
| | t = 23 min   20% A   80% B |
| | t = 30 min   83% A   17% B |
| Flow rate: | 1.0 mL/min |
| Injection volume: | 5 microliters |
| Stop Time: | 30 minutes |
| Post Time: | 5 minutes |
| Oven Temperature: | 40° C. |
| Detector: | UV (220 nm) |

Sample preparation: dissolve 25 mg of sample (dry solids weight) into a suitable solvent; adjust concentration to approximately 1 mg/ml. The sample concentration can be adjusted to ensure the proper quantitation.

| HPLC Retention times: | | | |
|---|---|---|---|
| (VI-a)/(VI*-a): | 14.5 min | (VI-b)/(VI*-b): | 10.5 min |
| (VII-a): | 10.0 min | (VII-b): | 5.7 min |
| (III-a): | 7.9 min | (III-b): | 4.3 min |
| (III-a): | 2.6 min | | |

The following working examples provide a further understanding of the method of the present invention. These examples are of illustrative purpose, and are not meant to limit the scope of the invention. Equivalent, similar, or suitable solvents, reagents or reaction conditions can be substituted for those particular solvents, reagents or reaction conditions described herein without departing from the general scope of the method of synthesis.

EXAMPLES

Melting points were determined on a Mel-temp II laboratory device and are uncorrected. Nuclear magnetic resonance spectra were recorded on a Bruker 250 and AMX400 400 MHz spectrometers with tetramethylsilane as the internal reference; chemical shifts (δ) are reported in parts per million (ppm), and the signals are described as s (singlet), d (doublet), t (triplet), q (quartet), bs (broad singlet), dd (doublet of doublet), and m (multiplet). UV spectra were obtained on a Beckman DU 650 spectrophotometer. Optical rotations were measured on a Jasco DIP-370 Digital Polarimeter. Mass spectra were measured on a Micromass Inc. Autospec High Resolution double focussing sector (EBE) MS spectrometers. Infrared spectra were recorded on a Nicolet 510 FT—IR spectrometer. Elemental analyses were performed by Atlantic Microlab, Inc., Norcross, Ga. All reactions were monitored using thin layer chromatography on Analtech, 200 mm silica gel GF plates. Dry 1,2-dichloroethane, dichloromethane, acetonitrile and THF were obtained by drying over 4A molecular sieves.

Example 1

Preparation of 5'-O-(α-Acetoxyisobutyryl)-3'-O-acetyl-2'-Bromo-2'-deoxy-5-fluorocytidine (II*-a) and 5'-O-(α-Acetoxy-isobutylyl)-2' O-acetyl-3'-bromo-3'-deoxy-5-fluorocytidine (II-a) from 5-fluorocytidine using 2-acetoxy-2-methyl-propionyl bromide as the acyl halide and EtOAc/$CH_3CN$ as the solvent.

Step (1). To a suspension of 5-fluorocytidine ((I), 26.1 g, 0.1 mole) in EtOAc (200 mL) and $CH_3CN$ (50 mL) was added 2-acetoxy-2-methyl-propionyl bromide (84.4 g, 0.4 mol) dropwise at room temperature under $N_2$. The resulting reaction mixture was then stirred at room temperature for 24 hours. The mixture was cooled to about 4° C. in an ice-water bath. An aqueous $KHCO_3$ solution (~10%) was added until the mixture reached a pH of about 8.0. The organic layer was separated and the aqueous layer was extracted one time with ethyl acetate. The combined organic solution was washed with brine. Concentration afforded the major products,(II-a) and (II*-a), and the minor products, (II-b) and (II*-b), as a solid in a ratio of 12.6:1 (43.6 g, 88%).

Analytical samples of the mixtures of products were separated by HPLC. A mixture of compounds (II-a) and (I*-a) was isolated as an amorphous solid: $^1$H NMR ($CDCl_3$) 1.58 (6H, s), 2.06 (3H, s), 2.17 (3H, s), 4.30–4.80 (4H, m), 5.33 and 5.45 (1H, s) 5.98 (1H, s), 7.98 and 8.04 (1H, d, J=6.0 Hz); $^{19}$F NMR ($CDCl_3$) −76.47 (s); $^{19}$F NMR ($CDCl_3$) −76.47 (s); MS (ESI) m/z, [M+H]$^+$, 496. A mixture of minor products, compounds of Formula (II-b) and (II*-b), was isolated as an amorphous solid. HPLC retention time for (II-a) and (II*-a) is 25.8 minutes and 22.5 minutes for (II-b) and (II*-b). $^1$H NMR ($CDCl_3$) 2.14 (3H, s), 2.16 (3H, s), 4.30–4.70 (4H, m), 5.39 and 5.48 (1H, s), 5.86 and 5.98 (1H, s), 7.96 and 8.02 (1H, d, J=6.0 Hz); $^{19}$F NMR ($CDCl_3$) −76.47 (s);

MS (ESI) m/z, [M+H]$^+$, 410.

Example 2

Preparation of (II-a) and (II*a) from 5-fluoro-cytidine using 2-acetoxy-2-methyl-propionyl bromide as the acyl halide and $CH_3CN$ as the solvent.

Step (1). To a suspension of 5-fluorocytidine ((I), 5.2 g, 0.02 mole) in $CH_3CN$ (40 mL) was added 2-acetoxy-2-methyl-propionyl bromide (16.7 g, 0.08 mol) dropwise at room temperature under $N_3$. The resulting reaction mixture was then stirred at room temperature for 18 hours. The mixture was diluted with EtOAc (80 mL) and then cooled to about 4° C. in an ice-water bath. An aqueous $KHCO_3$ solution (~10%) was added until the mixture reached a pH of about 8.0. The organic layer was separated and the aqueous layer was extracted two times with ethyl acetate. The combined organic solution was washed with brine. Concentration afforded the major products, (II-a) and (II*-a), and the minor products, (II-b) and (II*-b), as a solid in a ratio of 8.7:1 (6.8 g, 69%).

Example 3

Preparation (II-a) and (II*-a) from 5-fluorocytidine using 2-acetoxy-2-methyl-propionyl bromide as the acyl halide and $CH_2Cl_2$ as the solvent, in the presence of $Et_4NBr$.

Step (1). To a suspension of 5-fluorocytidine ((I), 2.61 g, 0.01 mole) and $Et_4NBr$ (6.3 g, 0.03 mol)in $CH_2CH_2$ (20 mL) was added 2-acetoxy-2-methyl-propionyl bromide dropwise (9.3 g, 0.03 mol) at room temperature under $N_2$. The resulting reaction mixture was then stirred at room temperature for 18 hours. The mixture was cooled to about 4° C. in an ice-water bath. An aqueous $KHCO_3$ solution (~10%) was added until the mixture reached a pH of about 8.0. The organic layer was separated and the aqueous layer was extracted one time with $CH_2Cl_2$. The combined organic solution was washed with brine. Concentration afforded the major products, (II-a) and (II*-a), and the minor products, (II-b) and (II*-b), as a solid in a ratio of 4.3:1 (4.17 g, 84%).

Example 4

Preparation of (II-a) and (II*a) from S-fluoro-cytidine using 2-acetoxy-2-methyl-propionyl bromide as the acyl halide and EtOAc as the solvent, in the presence of $Et_4NBr$ at 50° C.

Step (1). To a suspension of 5-fluorocytidine ((I), 2.61 g, 0.01 mole) and $Et_4NBr$ (6.3 g, 0.03 mol) in EtOAc (20 mL) was added α-acetoxy-isobutyryl bromide dropwise (6.3 g, 0.03 mol) at 50° C. under $N_2$. The resulting reaction mixture was then stirred at 50° C. for 22 hours. The mixture was cooled to about 4° C. in an ice-water bath. An aqueous $KHCO_3$ solution (~10%) was added until the mixture reached a pH of about 8.0. The organic layer was separated and the aqueous layer was extracted one time with ethyl acetate. The combined organic solution was washed with brine. Concentration afforded the major products, (II-a) and (II*-a), and the minor products, (II-b) and (II*-b), as a solid in a ratio of 2.3:1 (3.43 g, 69%).

Example 5

Preparation of (II-a) and (II*-a) from 5-fluoro-cytidine using 2-acetoxy-2-methyl-propionyl bromide as the acyl halide and $CH_3CN$ as the solvent at 50° C.

Step (1). To a suspension of 5-fluorocytidine ((I), 2.61 g, 0.01 mole) in $CH_3CN$ (20 mL) was added 2-acetoxy-2-methyl-propionyl bromide (8.4 g, 0.04 mol) dropwise at 50° C. under $N_2$. The resulting reaction mixture was then stirred at 50° C. for 6 hours. The mixture was diluted with EtOAc (40 mL) and then cooled to about 4° C. in an ice-water bath. An aqueous $KHCO_3$ solution (~10%) was added until the mixture reached a pH of about 8.0. The organic layer was separated and the aqueous layer was extracted two times with ethyl acetate. The combined organic solution was washed with brine. Concentration afforded the major products, (II-a) and (II*-a), and the minor products, (II-b) and (II*-b), as a solid in a ratio of 9.3:1(3.2 g, 66%).

Example 6

Preparation of (II-a) and (II*-a) from 5-fluoro-cytidine using 2-acetoxy-2-methyl-propionyl bromide as the acyl halide and EtOAc/$CH_3CN$ as the solvent in a kilogram scale reaction.

Step (1). A 50 L reactor was purged with $N_2$ for 10 minutes. To this reactor was charged 5-fluorocytidine ((I), 1.40 kg, 5.36 mole), EtOAc (10.8 L), and $CH_3CN$ (2.66 l) to form a slurry. The slurry was cooled to 20° C., and under vigorous agitation, 2-acetoxy-2-methyl-propionyl bromide (4.51 kg, 21.44 mol) was added over 1 h so that the temperature did not exceed 35° C. After addition, the resulting reaction mixture was agitated at room temperature for 20 hours. HPLC showed the conversion was over 99%. The mixture was cooled to about 4° C. A solution of $KHCO_3$ (3.22 kg, 32.2 mol) in water (16.1 L) was added. After addition, the mixture was vigorously agitated for 15 minutes and then the organic layer was separated from the aqueous layer. The aqueous layer was extracted one time with ethyl acetate (5.64 L), and the combined organic solution was washed with brine (7.6 L). HPLC analysis provided a solution yield of 86% with a ratio of products (II-a) and (II*-a) to (II-b) and (II*-b) of 12:1.

Example 7

Preparation of 5'-O-(α-Acetoxyisobutyryl)-2',3-didehydro-2',3'-dideoxy-5-fluoro-cytidine (III-a) using Zn—Cu as the reducing agent and MeOH/EtOAc as the solvent.

Step (2). Under $N_2(g)$ atmosphere, the mixture of products from Step (1), Example 1, (43.6 g, 0.088 mol) was dissolved in a mixed solvent of ethyl acetate (300 mL) and MeOH (100 mL). The Zn—Cu couple reducing agent, prepared as described below, was added. Acetic acid (2.4 mL, 0.044 mol) was introduced dropwise under vigorous agitation. The resulting reaction mixture was agitated for additional 7 hours at room temperature. The excess Zn—Cu couple was removed by filtration, and the filtrate was concentrated under reduced pressure. The residue was dissolved in 300 mL of EtOAc. To this EtOAc solution was added a $K_2CO_3$ (18.2 g, 0.132 mol) solution in 20 mL of water. The white solid was removed by filtration. The filtrate was washed with aqueous ammonia solution and brine, dried over $Na_2SO_4$. Removing the solvent gave 24.4 g (78%) of mixture of a major product (III-a) and a minor product, a compound of Formula (III-b) in a ratio of 20:1.

Preparation of Zn—Cu couple reducing agent: Zinc powder (14.3 g, 0.22 mol) and water (100 mL) were charged to a reaction vessel under $N_2$. A solution of $CuSO_4 \cdot H_2O$ (2.84 g, 0.012 mol) in 10 mL of water was added slowly. After addition, the mixture was stirred for additional 0.25 hours at room temperature. The Zn—Cu couple was collected by filtration followed by washing with water and MeOH. The wet cake was used immediately as described above.

Analytical sample of (III-a) as a white solid was obtained by HPLC separation. The HPLC retention time for (III-a) is 22.0 minutes: mp 247–249° C.; $^1H$ NMR ($CDCl_3$) 1.50 (3H, s), 1.52 (3H, s), 1.98 (3H, s), 4.17 (1H, dd, J=12.3 and 2.7 Hz), 4.51 (1H, dd, J=12.5 and 3.6 Hz), 5.04 (1H, m), 5.94 (1H, m), 6.15 (1H, m), 6.95 (1H, m), 7.59 (1H, J=6.2 Hz), 8.95 (1H, br); $^{19}F$ NMR ($CDCl_3$) –167.7 (s); MS (ESI, negative mode) m/z [M-H]$^-$, 354. Anal. Calcd for $C_{15}H_{18}FN_3O_6$: C, 50.70; H, 5.116; N,11.83. Found: C, 50.63; H, 5.12; N, 11.65. The minor product was an amorphous solid, a compound of Formula (III-b) having an HPLC retention time of 18.2 minutes. $^1H$ NMR ($CDCl_3$) 2.20 (3H, s), 4.20 (1H, dd, J=12.1 and 2.8 Hz), 4.50 (1H, dd, J=12.1 and 3.4 Hz), 5.08 (1H, m), 5.96 (1H, m), 6.12 (1H, m), 6.90 (1H, m), 7.48 (1H, J=6.1 Hz), 8.85 (1H, br); $^{19}F$ NMR ($CDCl_3$) –167.3 (s); MS (ESI, negative mode) m/z, [M-H]$^-$, 268.

Example 8

Preparation of (III-a) using Zn—Cu couple as the reducing agent and DMF as the solvent.

Step (2). The mixture of products of step (1) (8.9 g, 0.018 mol) was dissolved in DMF solvent (100 mL) under $N_2$. The Zn—Cu couple (6 g, 0.09 mol), prepared in the way as described in Example 7, was added. Acetic acid (0.8 mL, 0.015 mol) was introduced dropwise under vigorous agitation. The resulting reaction mixture was agitated for 3 hours at room temperature. The excess Zn—Cu couple was removed by filtration, and the filtrate was concentrated under reduced pressure. The residue was dissolved in 100 mL of EtOAc. To this EtOAc solution was added a $K_2CO_3$ (4.5 g, 0.033 mol) solution in 5 mL of water. The white solid was removed by filtration. The filtrate was washed with aqueous ammonia solution and brine, dried over $Na_2SO_4$. Removing the solvent gave 5.3 g (85%) of mixture of a major product (III-a) and a minor product, a compound of Formula (III-b) in a ratio of 10:1.

Example 9

Preparation of 5'-O-(α-Acetoxyisobutyryl)-2',3'-didehydro-2',3'-dideoxy-5-fluoro-cytidine (III-a) using Zn—Cu couple as the reducing agent and MeOH/EtOAc as the solvent.

Step (2). The mixture of products of Step (1)(2.79 g, 0.0056 mol) was dissolved in a mixed solvent of ethyl acetate (21 mL) and MeOH (7 mL). The Zn—Cu couple reducing agent (1.8 g, 0.028 mol), prepared in the way as described in example 7, was added under $N_2$. Acetic acid (0.31 mL, 0.0056 mol) was introduced dropwise under vigorous agitation. The resulting reaction mixture was agitated for an additional 5 hours at room temperature. The excess Zn—Cu couple was removed by filtration, and the filtrate was concentrated under reduced pressure. The residue was dissolved in 30 mL of EtOAc. To this EtOAc solution was added a $K_2CO_3$ (1.5 g, 0.011 mol) solution in 2 mL of water. The white solid was removed by filtration. The filtrate was washed with aqueous ammonia solution and brine, dried over $Na_2SO_4$. Removing the solvent gave 1.67 g (84%) of mixture of a major product (II-a) and a minor product, a compound of Formula (III-b) in a ratio of 20:1.

Example 10

Preparation of 5'-O-(α-Acetoxyisobutyryl)-2 '3'-didehydro-2',3'-dideoxy-5-fluoro-cytidine (III-a) in kilogram scale using Zn—Cu couple as the reducing agent and MeOH/EtOAc as the solvent.

Step (2). Freshly prepared Zn—Cu couple was charged to a 50 L reactor that was purged with $N_2$. See below for preparation of Zn—Cu couple. Methanol (7.4L) and a solution of the mixture of the products from step (1), Example 6 (22 L, 2.61 mol) were charged to the vessel. Subsequently, AcOH (0.14 L, 2.8 mol) was added to the vessel over 25 minutes under vigorous agitation. The temperature rose slowly to 31° C. After addition of AcOH, the mixture was agitated at room temperature until HPLC analysis showed the disappearance of the starting materials (~3 h). The excess Zn—Cu was removed by filtration through a bed of Celite and the cake was washed with 3.85 L MeOH. Methanol was removed from the filtrate solution under reduced pressure at a temperature of <30° C. to give a mixture of products in EtOAc (20 L, <1% v/v of MeOH). A solution of $K_2CO_3$ (1.16 Kg, 8.4 mol) in 1.1 L water was added to the EtOAc solution under vigorous agitation for 15 minutes, and a white solid was formed during the 15 minutes agitation period. The white solid was removed by filtration through a bed of Celite and then rinsed with 6.33 L of EtOAc. The filtrate was then washed with 10 N $NH_4OH$ (3.33 L) followed by brine (3.03 L×2). The EtOAc solvent was removed under reduced pressure at a temperature of <30° C., and MeOH was added back to replace the removed EtOAc. The final volume of the product solution was 12 L of MeOH with <1% of EtOAc (by volume). HPLC analysis showed a solution yield of 67%.

Preparation of Zn—Cu couple. A 12 L vessel was purged with N2 for 15 minutes. Water (6.3L) and Zn powder (0.91 Kg, 14.0 mol) were charged to this vessel. A solution of $CuSO_4.5H_2O$ (0.17 Kg, 0.79 mol) in 0.69 L of water was added to the vessel within 15 minutes. The resulting black suspension was agitated at room temperature for 15 minutes, and then the solid was collected by filtration. The cake was washed three times with a total volume of 8.25 L water and then three times with a total volume of 8.25 L methanol and was used immediately used.

Example 11

Preparation of 2',3'-didehydro-2',3'-dideoxy-5-fluoro-cytidine (IV) using NaOMe as the base.

Step (3). Products (III-a) and (III-b) of Example 7, (24.5 g, 0.069 mol), were dissolved in 200 mL of MeOH. To this solution was introduced a 25 wt % NaOMe solution (0.8 mL, 0.003 mol). The resulting reaction mixture was stirred at room temperature for 16 hours. The mixture was then concentrated under reduced pressure to half of the original volume. The white solid was collected by filtration (13.0 g, 83%). The HPLC retention time for (IV-a) is 8.3 minutes. $^1$H NMR ($CD_3OD$) 3.75 (2H, m); 4.85 (1H, m); 5.90 (1H, m); 6.32 (1H, m) 6.92 (1H, m); 8.14 (1H, d, J=6.6 Hz), $^{19}$F NMR ($CD_3OD$) −168.90 (d, J=0.016); mp 175–176° C.; MS (ESI, negative mode) m/z, [M−H]$^−$, 226.2. Anal. Calcd for $C_9H_{10}FN_3O_3$: C, 47.58; H, 4.45; N, 18.50. Found: C, 47.66; H, 4.32; N, 18.50.

Example 12

Preparation of (IV) using NH3 as the base.

Step (3). Products (III-a) and (111-b) (2.85 g, 0.008 mol) were dissolved in an ammonia-saturated MeOH solution (25 mL, ~36% Wt. $NH_3$ in MeOH) the resulting solution was stirred at room temperature for 16 hours. The mixture was then concentrated under reduced pressure and the residue was slurried with 10 mL of MeOH. The white solid was collected by filtration (1.37 g, 75%).

Example 13

Preparation of (IV) using Dowex® OH ion-exchange resin as the base.

Step (3). Products (III-a) and (III-b) (4.8 g, 0.013 mol), were dissolved 50 mL of MeOH. To this solution was added Dowex® OH ion-exchange resin (4.8 g) prepared as described below. The resulting mixture was stirred at room temperature for 12 hours. The Dowex® OH ion-exchange resin was filtered off and washed completely with MeOH. The MeOH solution was then concentrated under reduced pressure to a volume of ~20 mL. The white solid was collected by filtration (1.65 g, 54%).

Preparation of Dowex® OH ion-exchange resin: Dowex® 1X2-200 ion-exchange resin (20 g) was suspended in 20 mL of 50% wt NaOH solution and the suspension was stirred at room temperature for 30 minutes. The resin was collected by filtration and then washed with MeOH.

Example 14

Preparation of (IV) in kilogram scale from (III-a) and (III-b) using NaOMe as the base.

Step (3). To a 50 L reactor were charged a solution of the products (III-a) and (III-b) in MeOH from Step 2, Example 10 (24 L, 7.08 mol) and 25 wt % MeONa in MeOH (110 mL, 0.48 mol). The solution was agitated at room temperature for 12 hours, and then concentrated under reduced pressure at a temperature of <30° C. to a volume of 12 L. The resulting product slurry was cooled to 0° C. to 5° C. and stirred for 2 hours. The product was then collected by filtration (1.46 Kg, 91%).

Example 15

Preparation of 5'-O-(α-Acetoxyisobutyryl)-3'-O-acetyl-2'-Bromo-2'-deoxy-5-fluorouridine (II*-a) and 5'-O-(α-Acetoxy-isobutyryl)-2'-O-acetyl-3'-bromo-3'-deoxy-5-fluorouridine (II-a) from 5-fluorouridine using α-acetoxyisobutyryl bromide as the acyl halide and $CH_3CN$ as the solvent.

Step (1). To a suspension of 5-fluorouridine ((I), 0.5 g, 1.91 mmol) in $CH_3CN$ (40 mL) was added α-acetoxyisobutyryl bromide (1.6 g, 7.64 mmol) dropwise at room temperature under $N_2$. The resulting reaction mixture was then heated to reflux for 1 hour. The mixture was cooled to about 4° C. in an ice-water bath. Saturated $NaHCO_3$ solution (40 mL) was added. The mixture was extracted with EtOAc (20 mL×3) and the EtOAc solution was washed with brine and then dried over $Na_2SO_4$. Concentration afforded the major products (II-a) and (II*-a) and the minor products, (II-b) and (II*-b) as a solid in a ratio of 5:1 (780 mg, 83%). The mixture of products was used directly in step (2).

Analytical samples of the mixtures of products were separated by HPLC. A mixture of compounds (II-a) and (II*-a) was isolated as an amorphous solid: $^1$H NMR ($CDCl_3$) 1.49 (6H, s), 2.16 (3H, s), 2.20 (3H, s), 4.25–4.90 (4H, m), 5.34 and 5.48 (1H, s), 5.79 and 5.90 (1H, s), 7.96 and 8.14 (1H, d, J=6.0 Hz); $^{19}$F NMR ($CDCl_3$) −80.7 (s); MS (ESI) m/z, [M+H]$^+$, 497.

A mixture of minor products (II-b) or (II*-b) was isolated as an amorphous solid: $^1$H NMR ($CDCl_3$) 2.20 (3H, s), 2.15 (3H, s), 4.20–4.70 (4H, m), 5.38 and 5.42 (1H, s), 5.90 and 5.99 (1H, s), 7.99 and 8.11 (1H, d, J=6.0 Hz); $^{19}$F NMR ($CDCl_3$) −80.7 (s); MS (ESI) m/z, [M+H]$^+$, 411.

Example 16

Preparation of (VI*-a) and (VI-a) from 5-fluorouridine using α-acetoxyisobutyryl bromide as the acyl halide and $CH_3CN$ as the solvent in the presence of tetraethylammonium bromide Step (1). To a suspension of 5-fluorouridine ((V), 1.31 g, 5.0 mmol) and tetraethylammonium bromide (1.05 g, 5.0 mmol) in $CH_3CN$ (15 mL) was added α-acetoxyisobutyryl bromide (2.9 mL, 20 mmol) dropwise at room temperature under $N_2$. The resulting reaction mixture was then stirred at room temperature for 4 days. The mixture was cooled to about 4° C. in an ice-water bath. Saturated $NaHCO_3$ solution was added until the pH of the mixture was ~8.0. The mixture was extracted with EtOAc (20 mL×3) and the EtOAc solution was washed with brine and then dried over $Na_2SO_4$. Concentration afforded the major products (VI-a) and (VI*-a) and the minor products, (VI-b) and (VII*-b) as an amorphous solid in a ratio of 3.6:1 (2.36 g, 95.3%).

Example 17

Preparation of (VI*a) and (VI-a) from 5-fluorouridine using α-acetoxyisobutyryl bromide as the acyl halide and $CH_3CN$ as the solvent in the presence of tetraethylammonium bromide Step (1). To a suspension of 5-fluorouridine ((V), 1.31 g, 5.0 mmol) and tetraethylammonium bromide (1.05 G, 5.0 mmol) in $CH_3CN$ (15 mL) was added α-acetoxyisobutyryl bromide (2.9 mL, 20 mmol) dropwise at room temperature under N₂. The resulting reaction mixture was then heated at 45° C. overnight. The mixture was cooled to about 4° C. in an ice-water bath. Saturated NaHCO₃ solution was added until the pH of the mixture was ~8.0. The mixture was extracted with EtOAc (20 mL×3) and the EtOAc solution was washed with brine and then dried over Na₂SO₄. Concentration afforded the major products (VI-a) and (VI*-a) and the minor products, (VI-b) and (VI*-b) as an amorphous solid in a ratio of 3.9:1 (2.34 g, 94.5%).

Example 18

Preparation of (VI*-a) and (VI-a) from 5-fluorouridine using α-acetoxyisobutyryl bromide as the acyl halide and CH₃CN as the solvent Step (1). To a suspension of 5-fluorouridine ((V), 1.31 g, 5.0 mmol) in CH₃CN (15 mL) was added α-acetoxyisobutyryl bromide (2.9 mL, 20 mmol) dropwise at room temperature under N₂. The resulting reaction mixture was then heated at 45° C. overnight. The mixture was cooled to about 4° C. in an ice-water bath. Saturated NaHCO₃ solution was added until the pH of the mixture was ~8.0. The mixture was extracted with EtOAc (20 mL×3) and the EtOAc solution was washed with brine and then dried over Na₂SO₄. Concentration afforded the major products (VI-a) and (VI*-a) and the minor products, (VI-b) and (VI*-b) as an amorphous solid in a ratio of 2.4:1 (2.4 g, 99%).

Example 19

Preparation of (VI*-a) and (VI-a) from 5-fluorouridine using α-acetoxyisobutyryl bromide as the acyl halide and CH₃CN and EtOAc as the solvent.

Step (1). To a suspension of 5-fluorouridine ((V), 0.67 g, 2.5 mmol) in CH₃CN (4 mL) and EtOAc (4 mL) was added α-acetoxyisobutyryl bromide (1.5 mL, 10 mmol) dropwise at room temperature under N₂. The resulting reaction mixture was then heated at 45° C. overnight. The mixture was cooled to about 4° C. in an ice-water bath. Saturated NaHCO₃ solution was added until the pH of the mixture was ~8.0. The mixture was extracted with EtOAc (20 mL×3) and the EtOAc solution was washed with brine and then dried over Na₂SO₄. Concentration afforded a mixture of (VI-a), (VI*-a) and (VI-b), (VI*-b) as an amorphous solid in a ratio of 1:1 (1.2 g, 97%).

Example 20

Preparation of 5'-O-(α-Acetoxyisobutyryl)-2',3'-didehydro-2',3'-dideoxy-5-fluorouridine (VII-a) using Zn as the reducing agent and DMF as the solvent.

Step (2). Under a N₂(g) atmosphere, the mixture of products from Step (1), Example 1, (2.5 g, 5.0 mmol) was dissolved in DMF (150 mL). Zn (10 g, 154 mmol) was added. Acetic acid (2.5 mL, 45 mmol) was introduced dropwise under vigorous agitation. The resulting reaction mixture was agitated for 2 hours at room temperature. The excess Zn was removed by filtration, and the filtrate was concentrated under reduced pressure. The residue was dissolved in 50 mL of EtOAc and washed with 10 M NH₄OH and brine, dried over Na₂SO₄. Concentration afforded the product as an amorphous solid (1.34 g, 76%). An analytical sample was obtained by crystallization from EtOAc/Hexane to provide a white solid; [α]D −45.5 (c, 0.83, CHCl₃, 25° C.); mp 154–156° C.; ¹H NMR (CDCl₃) δ 1.53 (3H, s), 1.56 (3H, s), 2.02 (3H, s), 4.22 (1H, dd, J=12.5, 253.0 Hz), 4.54 (1H, dd, J=12.5, 3.0 Hz), 5.07 (1H, m), 5.88 (1H, m), 6.29 (1H, m), 6.99 (1H, m), 7.61 (1H, J=5.5 Hz), 9.35 (1H, br); ¹⁹F NMR (CDCl₃)δ 163.7 (s); MS (ESI) m/z (relative intensity %) 379 ([M+Na]⁺, 100. Anal. Calcd for C₁₅H₁₇FN₂O₇: C, 50.56; H, 4.819; N, 7.86. Found: C, 50.64; H, 4.77; N, 7.80.

Example 21

Preparation of 5'-O-(α-Acetoxyisobutyryl)-2',3'-didehydro-2',3'-dideoxy-5-fluorouridine (VII-a) using Zn as the reducing agent and EtOAc and MeOH as the solvent.

Step (2). Under a N₂(g) atmosphere, the mixture of products from Step (1), Example 1, (2.5 g, 5.0 mmol) was dissolved in EtOAc (30 mL) and MeOH (10 mL). Zn (0.8 g, 12.5 mmol) was added. Acetic acid (0.14 mL, 2.5 mmol) was introduced dropwise under vigorous agitation. The resulting reaction mixture was agitated for 5 hours at room temperature. The excess Zn was removed by filtration, and the filtrate was concentrated under reduced pressure. The residue was dissolved in 50 mL of EtOAc and washed with 10 M NH₄OH and brine, dried over Na₂SO₄. Concentration afforded the product as an amorphous solid (1.53 g, 87%).

Example 22

Preparation of 5'-O-(α-Acetoxyisobutyryl)-2',3'-didehydro-2',3'-dideoxy-5-fluorocytidine (III-a).

Step (3-a). POCl₃ (0.43 mL, 4.62 mmol) was added to a solution of 1,2,4-triazole (1.06 g, 18.7 mmol) and TEA (2.1 mL, 18.7 mmol) in CH₃CN (15 mL) at 0° C. After addition, the mixture was stirred at room temperature for 4 hrs. The solid was filtered off and the filtrate mixed with compounds (VII-a) and (VII-b) from Step 2, Example 6 (500 mg, 1.4 mmol). The solution was stirred at room temperature for 4 hrs, and then cooled in ice-water bath.

Step (3-b). Excess NH₃ (g) was bubbled into the mixture slowly for 0.5 hr. The mixture was concentrated and the residue was partitioned between water (20 mL) and CH₂Cl₂ (30 mL), and the CH₂Cl₂ solution was dried over Na₂SO₄. Concentration gave (III-a) as the major product. Analytical sample of (III-a) was obtained by chromatograph separation (CH₂Cl₂/MeOH) to afford a white solid (300 mg, 60%): mp 247–249° C.; ¹H NMR (CDCl₃) 1.50 (3H, s), 1.52 (3H, s), 1.98 (3H, s), 4.17 (1H, dd, J=12.3 and 2.7 Hz), 4.51 (1H, dd, J=12.5 and 3.6 Hz), 5.04 (1H, m), 5.94 (1H, m), 6.15 (1H, m), 6.95 (1H, m), 7.59 (1H, J=6.2 Hz), 8.95 (1H, br); ¹⁹F NMR (CDCl₃) −167.7 (s); MS (ESI, negative mode) m/z [M−H]⁻, 354. Anal. Calcd for C₁₅H₁₈FN₃O₆: C, 50.70; H, 5.116; N,11.83. Found: C,50.63; H, 5.12; N, 11.65.

Example 23

Preparation of 2',3'-didehydro-2',3'-dideoxy-5-fluorocytidine (III) from (III-b) and (III-a) using NaOMe as the base.

Step (3-c). Compounds (III-b) and (III-a) (24.5 g, 0.069 mol), were dissolved in 200 mL of MeOH. To this solution was introduced a 25 wt % NaOMe solution (0.8 mL, 0.003 mol). The resulting reaction mixture was stirred at room temperature for 16 hours. The mixture was then concentrated under reduced pressure to half of the original volume. The white solid was collected by filtration (13.0 g, 83%): mp 175–176° C.; ¹H NMR (CD₃OD) 3.75 (2H, m); 4.85 (1H, m); 5.90 (1H, m); 6.32 (1H, m) 6.92 (1H, m); 8.14 (1H, d, J=6.6 Hz). $^{19}$F NMR (CD$_3$OD) −168.90 (d, J=0.016); MS (ESI, negative mode) m/z, [M−H]$^-$, 226.2. Anal. Calcd for C$_9$H$_{10}$FN$_3$O$_3$: C, 47.58; H, 4.45; N, 18.50. Found: C, 47.66; H, 4.32; N, 18.50.

Example 24

Preparation of (III) from (III-b) and (III-a) using NH$_3$ as the base.

Step (3-c). Products (III-b) and (III-a) (2.85 g, 0.008 mol), were dissolved in an ammonia-saturated MeOH solution (25 mL, ~36% Wt. NH$_3$ in MeOH) the resulting solution was stirred at room temperature for 16 hours. The mixture was then concentrated under reduced pressure and the residue was slurried with 10 mL of MeOH. The white solid was collected by filtration (1.37 g, 75%).

Example 25

Preparation of (III) from (III-b) and (III-a) using Dowex-OH as the base

Step (3-c). Products (III-b) and (III-a) (4.8 g, 0.013 mol), were dissolved 50 ML of MeOH. To this solution was added Dowex-OH resin (4.8 g), whose preparation was described below. The resulting mixture was stirred at room temperature for 12 hours. The Dowex resin was filtered off and washed completely with MeOH. The MeOH solution was then concentrated under reduced pressure to a volume of ~20 mL. The white solid was collected by filtration (1.65 g, 54%).

Preparation of Dowex-OH resin: Dowex-Cl resin (20 g) was suspended in 20 mL of 50% wt NaOH solution and the suspension was stirred at room temperature for 30 minutes. The resin was collected by filtration and then washed with MeOH.

Although the present invention has been described with respect to a specific embodiment, the details of the embodiment is not to be construed as limitations. For instance, while this disclosure uses β-D-D4FC as an illustrative model reaction, it should be understood that any β-D or β-L D4 or D2 nucleoside can be made according to the present invention, and is not limited to this specific embodiment. Various equivalents, changes and modification can be made without departing from the spirit and the scope of this invention, and it is understood that such equivalent embodiments are part of this invention. The present invention can be embodied in other specific forms without departing from the spirit or essential attributes thereof and, accordingly, reference should be made to the appended claims as further indicating the scope of the invention.

We claim:

1. A process for the preparation of a compound of Formula (IV):

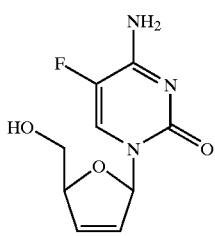

(IV)

comprising:

(1) contacting a compound of Formula (I):

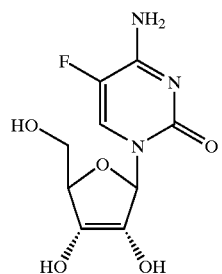

(I)

with an acyl halide of Formula Q—C(=O)X, wherein:

Q is 2-(R$^1$CH$_2$CO$_2$)phenyl-, R$^1$CH$_2$—, or R$^1$CH$_2$C(=O)OC(R$^2$)$_2$—;

X is Cl, Br, or I;

R$^1$ is H or C$_1$–C$_6$ alkyl;

R$^2$, at each occurrence, is independently selected from methyl, ethyl, and propyl;

in a suitable polar aprotic solvent at a temperature from about 0° C. to 60° C. to form a compound of Formula (II), a compound of Formula (II*), or a mixture of compounds of Formula (II) and (II*):

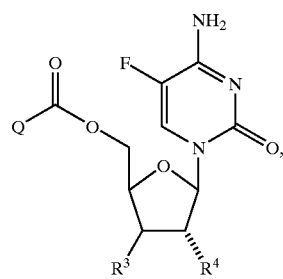

(II)

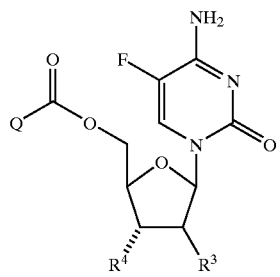

(II*)

wherein R$^3$ is X; and R$^4$ is R$^1$CH$_2$C(=O)O—;

(2) contacting the compound of Formula (II), the compound of Formula (II*), or the mixture of compounds of Formula (II) and (II*); with a suitable reducing agent in a suitable polar solvent, in the absence of an acid catalyst, to form a compound of Formula (III):

(III)

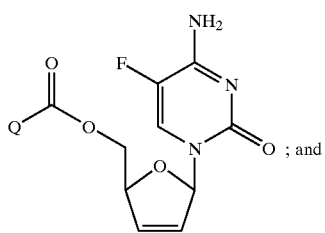
; and (3) contacting the compound of Formula (III) with a suitable base to form the compound of Formula (IV).

2. The process of claim 1 for the preparation of a compound of Formula (IV), wherein:

in step (1) the acyl halide of Formula Q—C(=O)X comprises:

2-acetoxy-2-methyl-propionyl bromide, 2-(acetoxy)-2-methyl-butanoyl bromide, 2-(acetoxy)-2-ethyl-butanoyl bromide, or 2-(acetoxy)-2-methyl-pentanoyl bromide;

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

3. The process according to claim 1, for the preparation of a compound of Formula (IV):

(IV)

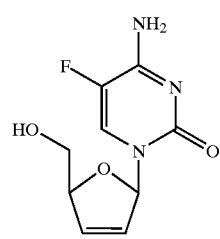

comprising:

(1) contacting a compound of Formula (I):

(I)

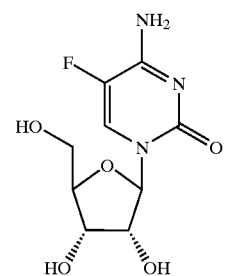

with 2-acetoxy-2-methyl-propionyl bromide in a suitable polar aprotic solvent to form a compound of Formula (II-a), a compound of Formula (II*-a), or a mixture of compounds of Formula (II-a) and (II*-a):

(II-a)

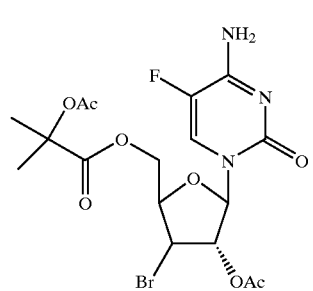

, (II*-a)

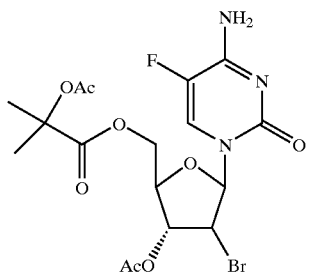

(2) contacting the compound of Formula (II-a), the compound of Formula (II*-a), or the mixture of compounds of Formula (II-a) and (II*-a); with a suitable reducing agent in a suitable polar solvent, in the absence of an acid catalyst, to form a compound of Formula (III-a):

(III-a)

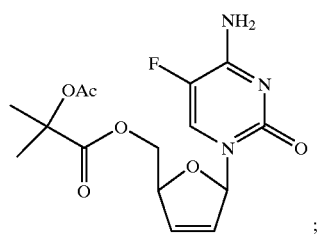

; and (3) contacting the compound of Formula (III-a) with a suitable base to form the compound of Formula (IV).

4. The process of claim 3 for the preparation of a compound of Formula (IV), wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

5. The process of claim 4 for the preparation of a compound of Formula (IV), wherein:

in step (1), the suitable polar aprotic solvent comprises a combination of acetonitrile and ethyl acetate;

in step (2), the suitable reducing agent is Zn—Cu couple;

in step (2), the suitable polar solvent comprises a combination of methanol and ethyl acetate; and in step (3) the suitable base is sodium methoxide.

6. The process according to claim 5, for the preparation of a compound of Formula (IV):

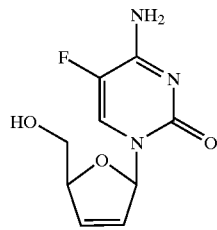
(IV)

comprising:

(1) contacting a compound of Formula (I):

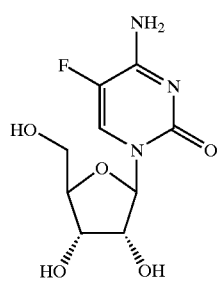
(I)

with 2-acetoxy-2-methyl-propionyl bromide in a suitable polar aprotic solvent comprising a combination of acetonitrile and ethyl acetate, wherein the ratio of acetonitrile to ethyl acetate is 1:4; to form a compound of Formula (II-a), a compound of Formula (II*-a), or a mixture of compounds of Formula (II-a) and (II*-a):

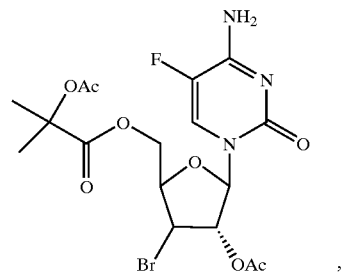
(II-a)

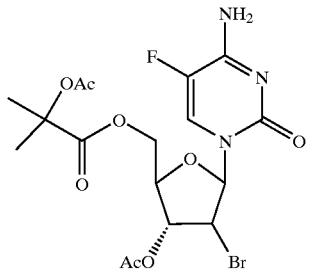
(II*-a)

(2) contacting the compound of Formula (II-a), the compound of Formula (II*-a), or the mixture of compounds of Formula (II-a) and (II*-a); with Zn—Cu couple in a suitable polar solvent comprising a combination of methanol and ethyl acetate, wherein the ratio of methanol to ethyl acetate is in the range of 1:2 to 1:4, to form a compound of Formula (III-a):

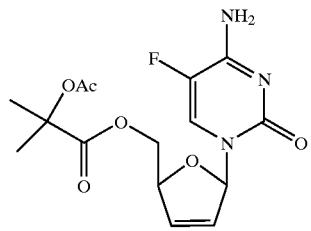
(III-a)

; and (3) contacting the compound of Formula (III-a) with sodium methoxide to form the compound of Formula (IV).

7. The process of claim 1 for the preparation of a compound of Formula (IV):

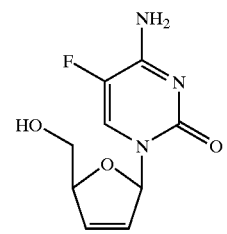
(IV)

comprising:

(1) contacting a compound of Formula (I):

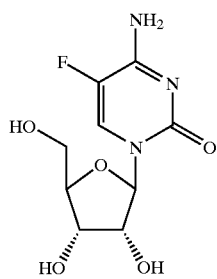

(I)

with an acyl halide of Formula Q—C(=O)X, wherein:
Q is $R^1CH_2C(=O)OC(R^2)_2$—;
X is Cl, Br, or I;
$R^1$ is H, $CH_3$, $CH_2CH_3$, or $CH_2CH_2CH_3$;
$R^2$, at each occurrence, is independently selected from methyl, ethyl, and propyl;
in a suitable polar aprotic solvent to form a compound of Formula (II) or a compound of Formula (II*):

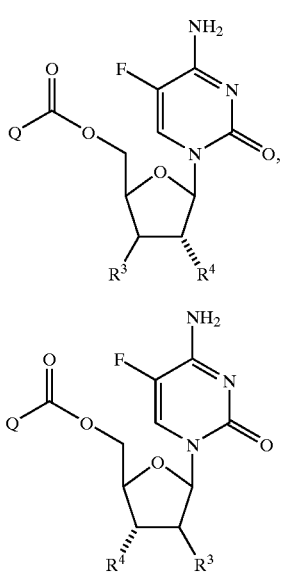

(II)

(II*)

wherein $R^3$ is X; and $R^4$ is $R^1CH_2C(=O)O$—;

(2) contacting the compound of Formula (II) or the compound of Formula (II*) with a suitable reducing agent in a suitable polar solvent, in the absence of an acid catalyst, to form a compound of Formula (III):

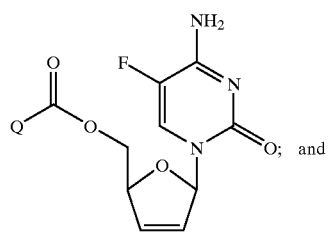

(III-a)

and (3) contacting the compound of Formula (III) with a suitable base to form the compound of Formula (IV).

8. The process of claim 7 for the preparation of a compound of Formula (IV), wherein:

in step (1) the acyl halide of Formula Q—C(=O)X comprises:
2-acetoxy-2-methyl-propionyl bromide, 2-(acetoxy)-2-methyl-butanoyl bromide,
2-(acetoxy)-2-ethyl-butanoyl bromide, or 2-(acetoxy)-2-methyl-pentanoyl bromide;

in step (1), the suitable polar aprotic solvent comprises
one polar aprotic solvent or a combination of two or more polar aprotic solvents;
and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn;

in step (2), the suitable polar solvent comprises
one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

9. The process according to claim 7, for the preparation of a compound of Formula (IV):

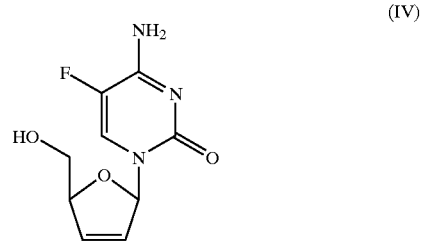

(IV)

comprising:

(1) contacting a compound of Formula (I):

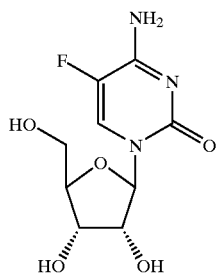

(I)

with 2-acetoxy-2-methyl-propionyl bromide in a suitable polar aprotic solvent to form a compound of Formula (II-a) or a compound of Formula (II*-a):

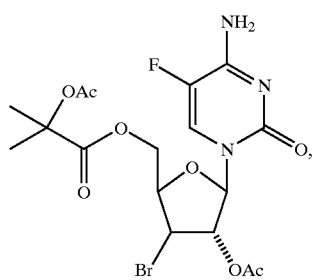
(II-a)

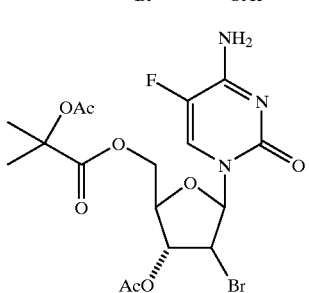
(II*-a)

(2) contacting the compound of Formula (II-a) or the compound of Formula (II*-a) with a suitable reducing agent in a suitable polar solvent, in the absence of an acid catalyst, to form a compound of Formula (III-a):

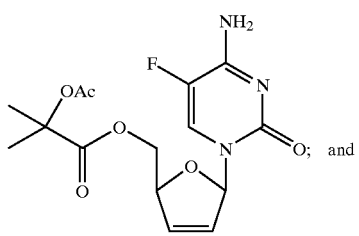
(III-a)
and (3) contacting the compound of Formula (III-a) with a suitable base to form the compound of Formula (IV).

10. The process of claim 9 for the preparation of a compound of Formula (IV), wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

11. The process of claim 10 for the preparation of a compound of Formula (IV), wherein:

in step (1), the suitable polar aprotic solvent comprises a combination of acetonitrile and ethyl acetate;

in step (2), the suitable reducing agent is Zn—Cu couple;

in step (2), the suitable polar solvent comprises a combination of methanol and ethyl acetate; and in step (3) the suitable base is sodium methoxide.

12. process according to claim 11, for the preparation of a compound of Formula (IV):

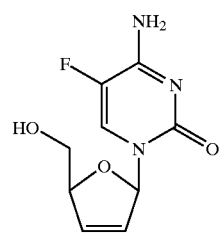
(IV)

comprising:

(1) contacting a compound of Formula (I):

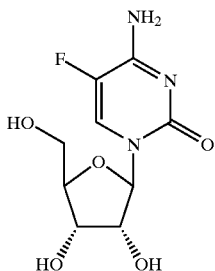
(I)

with 2-acetoxy-2-methyl-propionyl bromide in a suitable polar aprotic solvent comprising a combination of acetonitrile and ethyl acetate, wherein the ratio of acetonitrile to ethyl acetate is 1:4; to form a compound of Formula (II-a) or a compound of Formula (II*-a):

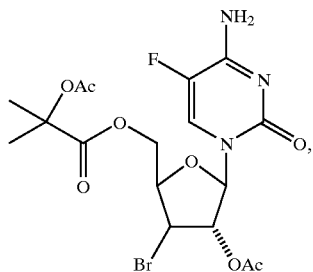
(II-a)

-continued (II*-a)

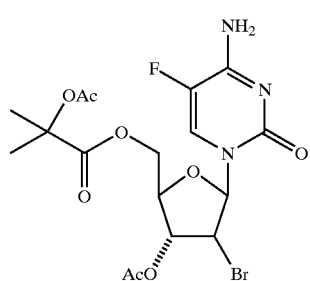

(2) contacting the compound of Formula (II-a) or the compound of Formula (II*-a); with Zn—Cu couple in a suitable polar solvent comprising a combination of methanol and ethyl acetate, wherein the ratio of methanol to ethyl acetate is in the range of 1:2 to 1:4, to form a compound of Formula (III-a):

(III-a)

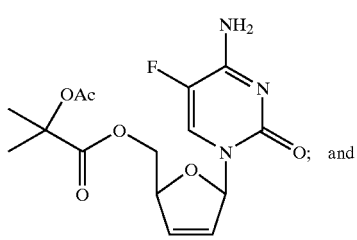

(3) contacting the compound of Formula (III-a) with sodium methoxide to form the compound of Formula (IV).

13. The process of claim 1 for the preparation of a compound of Formula (IV):

(IV)

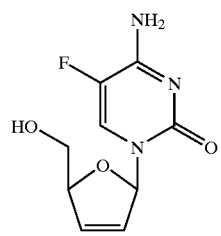

comprising:
(1) contacting a compound of Formula (I):

(I)

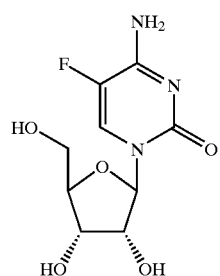

with an acyl halide of Formula Q—C(=O)X, wherein:
Q is $R^1CH_2C(=O)OC(R^2)_2$—;
X is Cl, Br, or I;

$R^1$ is H, $CH_3$, $CH_2CH_3$, or $CH_2CH_2CH_3$;
$R^2$, at each occurrence, is independently selected from methyl, ethyl, and propyl;
in a suitable polar aprotic solvent to form a mixture of compounds of Formula (II) and (II*):

(II)

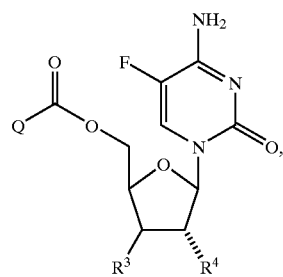

(II*)

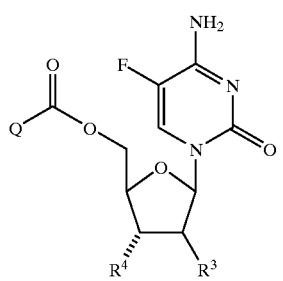

wherein $R^3$ is X; and $R^4$ $R^1CH_2C(=O)O$—;

(2) contacting the mixture of compounds of Formula (II) and (II*) with a suitable reducing agent in a suitable polar solvent, in the absence of an acid catalyst, to form a compound of Formula (III):

(III)

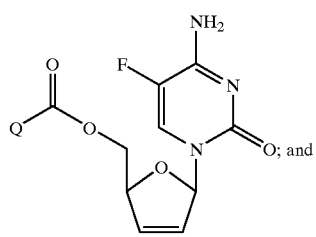

(3) contacting the compound of Formula (III) with a suitable base to form the compound of Formula (IV).

14. The process of claim 13 for the preparation of a compound of Formula (IV), wherein:
in step (1) the acyl halide of Formula Q—C(=O)X comprises:
2-acetoxy-2-methyl-propionyl bromide, 2-(acetoxy)-2-methyl-butanoyl bromide,
2-(acetoxy)-2-ethyl-butanoyl bromide, or 2-(acetoxy)-2-methyl-pentanoyl bromide;
in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

15. The process according to claim 13, for the preparation of a compound of Formula (IV):

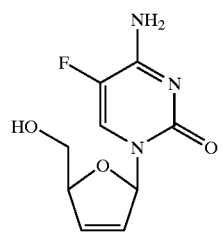
(IV)

comprising:

(1) contacting a compound of Formula (I):

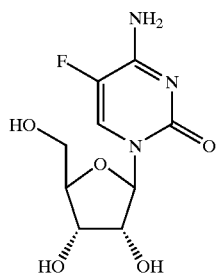
(I)

with 2-acetoxy-2-methyl-propionyl bromide in a suitable polar aprotic solvent to form a mixture of compounds of Formula (II-a) and (II*-a):

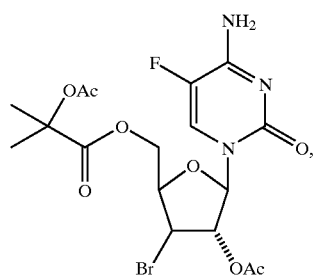
(II-a)

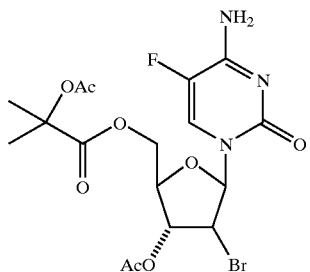
(II*-a)

(2) contacting the mixture of compounds of Formula (II-a) and (II*-a) with a suitable reducing agent in a suitable polar solvent, in the absence of an acid catalyst, to form a compound of Formula (III-a):

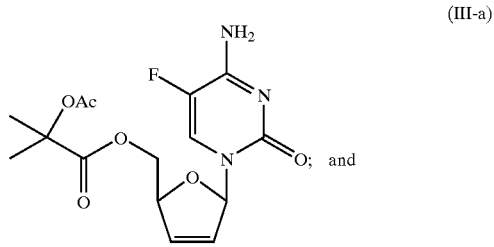
(III-a)

and (3) contacting the compound of Formula (III-a) with a suitable base to form the compound of Formula (IV).

16. The process of claim 15 for the preparation of a compound of Formula (IV), wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

17. The process of claim 16 for the preparation of a compound of Formula (IV), wherein:

in step (1), the suitable polar aprotic solvent comprises a combination of acetonitrile and ethyl acetate;

in step (2), the suitable reducing agent is Zn—Cu couple;

in step (2), the suitable polar solvent comprises a combination of methanol and ethyl acetate; and in step (3) the suitable base is sodium methoxide.

18. The process according to claim 17, for the preparation of a compound of Formula (IV):

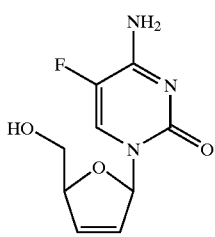

(IV)

comprising:

(1) contacting a compound of Formula (I):

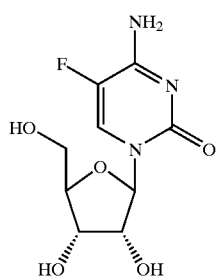

(I)

with 2-acetoxy-2-methyl-propionyl bromide in a suitable polar aprotic solvent comprising a combination of acetonitrile and ethyl acetate, wherein the ratio of acetonitrile to ethyl acetate is 1:4; to form a mixture of compounds of Formula (II-a) and (II*-a):

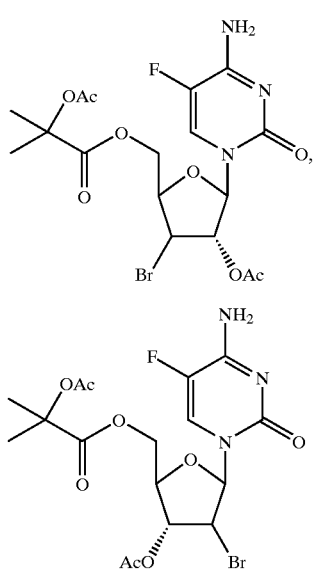

(II-a)

(II*-a)

(2) contacting the mixture of compounds of Formula (II-a) and (II*-a) with Zn—Cu couple in a suitable polar solvent comprising a combination of methanol and ethyl acetate, wherein the ratio of methanol to ethyl acetate is in the range of 1:2 to 1:4, to form a compound of Formula (III-a):

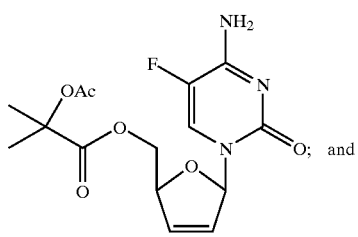

(III-a)

(3) contacting the compound of Formula (III-a) with sodium methoxide to form the compound of Formula (IV).

19. A process for the preparation of a compound of Formula (III):

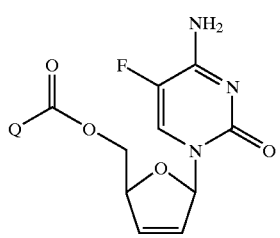

(III)

wherein:

Q is 2-($R^1CH_2CO_2$)phenyl-, $R^1CH_2$—, or $R^1CH_2C(=O)$ $OC(R^2)_2$—;

$R^1$ is H or $C_1$–$C_6$ alkyl;

$R^2$, at each occurrence, is independently selected from methyl, ethyl, and propyl;

comprising:

(1) contacting a compound of Formula (I):

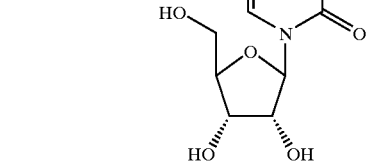

(I)

with an acyl halide of Formula Q—C(=O)X, wherein:

Q is 2-($R^1CH_2CO_2$)phenyl-, $R^1CH_2$—, or $R^1CH_2C(=O)$ $OC(R^2)_2$—;

X is Cl, Br, or I;

$R^1$ is H or $C_1$–$C_6$ alkyl;

$R^2$, at each occurrence, is independently selected from methyl, ethyl, and propyl;

in a suitable polar aprotic solvent at a temperature from about 0° C. to 60° C. to form a compound of Formula (II), a compound of Formula (II*), or a mixture of compounds of Formula (II) and (II*):

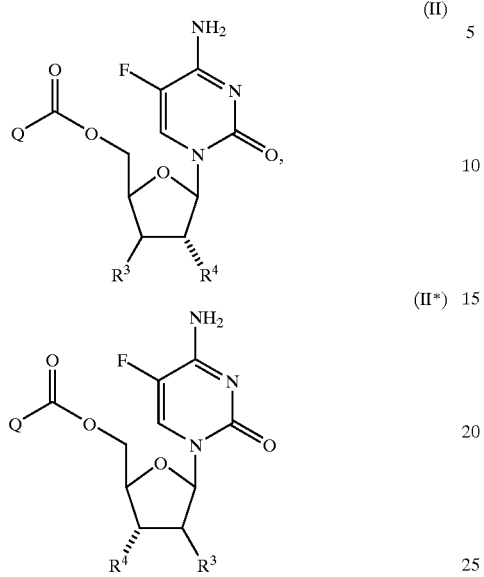

wherein $R^3$ is X; and $R^4$ is $R^1CH_2C(=O)O$—; and (2) contacting the compound of Formula (II), the compound of Formula (II*), or the mixture of compounds of Formula (II) and (II*); with a suitable reducing agent in a suitable polar solvent, in the absence of an acid catalyst, to form a compound of Formula (III).

20. The process of claim 19 for the preparation of a compound of Formula (III), wherein:

in step (1) the acyl halide of Formula Q—C(=O)X comprises:
  2-acetoxy-2-methyl-propionyl bromide, 2-(acetoxy)-2-methyl-butanoyl bromide, 2-(acetoxy)-2-ethyl-butanoyl bromide, or 2-(acetoxy)-2-methyl-pentanoyl bromide;

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn; and in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether.

21. The process according to claim 19, for the preparation of a compound of Formula (III-a):

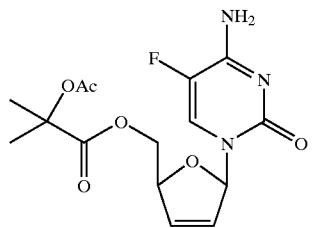

comprising:

(1) contacting a compound of Formula (I):

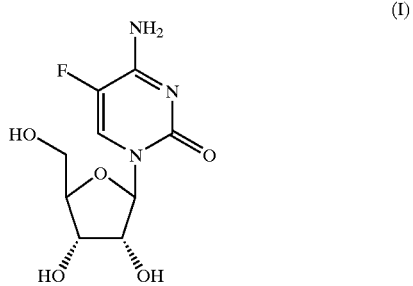

with 2-acetoxy-2-methyl-propionyl bromide in a suitable polar aprotic solvent to form a compound of Formula (II-a), a compound of Formula (II*-a), or a mixture of compounds of Formula (II-a) and (II*-a):

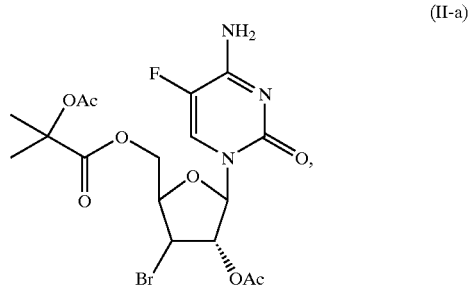

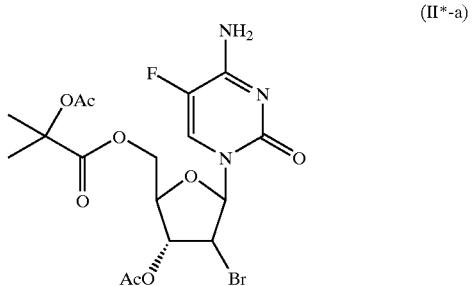

(2) contacting the compound of Formula (II-a), the compound of Formula (II*-a), or the mixture of compounds of Formula (II-a) and (II*-a); with a suitable reducing agent in a suitable polar solvent, in the absence of an acid catalyst, to form a compound of Formula (III-a).

22. The process of claim 21 for the preparation of a compound of Formula (III-a), wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the suitable reducing agent is selected from the group consisting of: Fe, Zn—Cu couple and Zn; and in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether.

23. The process of claim 22 for the preparation of a compound of Formula (III-a), wherein:

in step (1), the suitable polar aprotic solvent comprises a combination of acetonitrile and ethyl acetate;

in step (2), the suitable reducing agent is Zn—Cu couple; and in step (2), the suitable polar solvent comprises a combination of methanol and ethyl acetate.

24. The process according to claim 23, for the preparation of a compound of Formula (III-a):

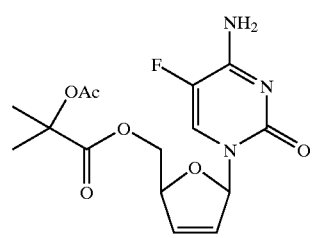

(III-a)

comprising:

(1) contacting a compound of Formula (I):

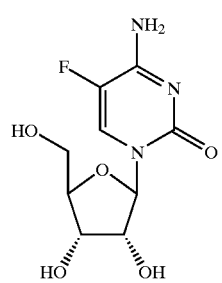

(I)

with 2-acetoxy-2-methyl-propionyl bromide in a suitable polar aprotic solvent comprising a combination of acetonitrile and ethyl acetate, wherein the ratio of acetonitrile to ethyl acetate is 1:4; to form a compound of Formula (II-a), a compound of Formula (II*-a), or a mixture of compounds of Formula (II-a) and (II*-a):

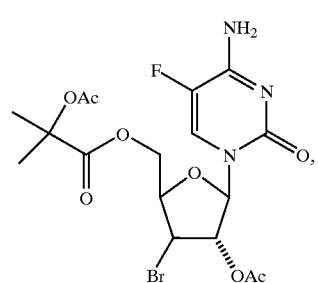

(II-a)

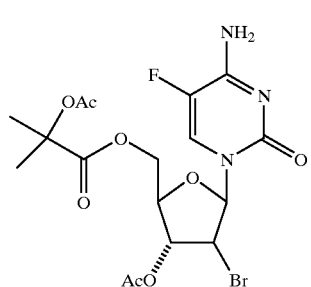

(II*-a)

(2) contacting the compound of Formula (II-a), the compound of Formula (II*-a), or the mixture of compounds of Formula (II-a) and (II*-a); with Zn—Cu couple in a suitable polar solvent comprising a combination of methanol and ethyl acetate, wherein the ratio of methanol to ethyl acetate is in the range of 1:2 to 1:4, to form a compound of Formula (III-a).

25. A compound of Formula (II) or (II*):

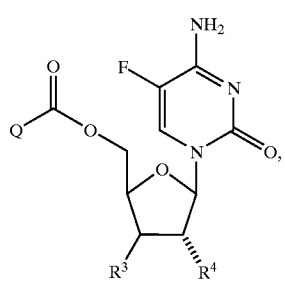

(II)

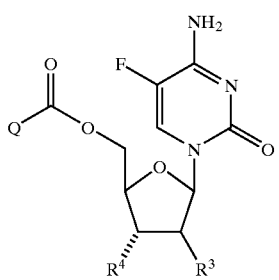

(II*)

or a pharmaceutically acceptable salt thereof, wherein:

in Formula II, Q is $R^1CH_2$—

$R^1$ is $C_1$–$C_6$ alkyl;

$R^2$ is independently selected from methyl, ethyl, and propyl;

$R^3$ is Cl, Br, or I; and $R^4$ is $R^1CH_2C(=O)O$—;

or in Formula II, Q is $R^1CH_2C(=O)OC(R^2)_2$—;

$R^1$ is H or $C_1$–$C_6$ alkyl;

$R^2$ is independently selected from methyl, ethyl, and propyl;

$R^3$ is Cl, Br, or I; and $R^4$ $R^1CH_2C(=O)O-$;

and wherein:

in Formula II*,

Q is $R^1CH_2C(=O)OC(R^2)_2-$;

$R^1$ is H or $C_1-C_6$ alkyl;

$R^2$ is independently selected from methyl, ethyl, and propyl;

$R^3$ is Cl, Br, or I; and $R^4$ is $R^1CH_2C(=O)O-$;.

26. A compound of Formula (II-a) or (II*-a):

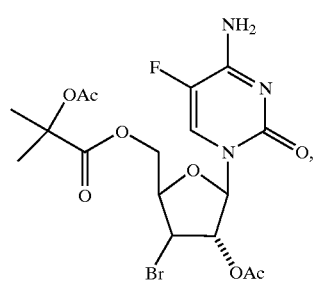

(II-a)

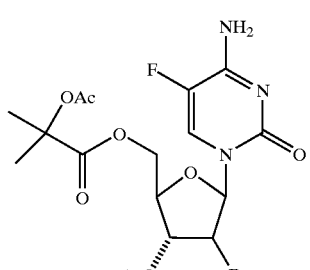

(II*-a)

or a pharmaceutically acceptable salt thereof.

27. A compound of Formula (III):

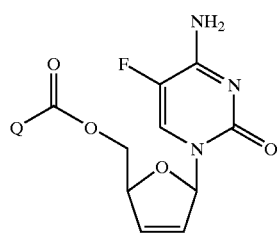

(III)

or a pharmaceutically acceptable salt thereof, wherein:

Q is $R^1CH_2C(=O)OC(R^2)_2-$;

$R^1$ is H or $C_1-C_6$ alkyl; and $R^2$ is independently selected from methyl, ethyl, and propyl.

28. A compound of Formula (III-a):

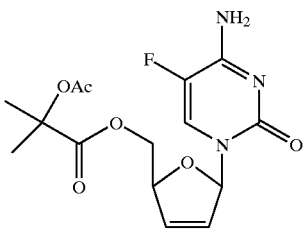

(III-a)

or a pharmaceutically acceptable salt thereof.

29. A process for the preparation of a compound of Formula (IV):

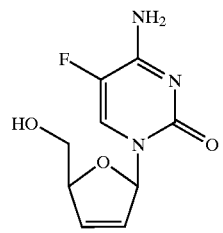

(IV)

comprising:

(1) contacting a compound of Formula (IV):

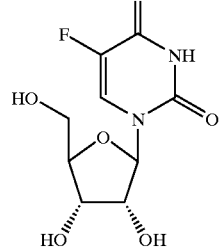

(V)

with an acyl halide of Formula Q—C(=O)X, wherein:

Q is 2-($R^1CH_2CO_2$)phenyl-, $R^1CH_2-$, or $R^1CH_2C(=O)OC(R^2)_2-$;

X is Cl, Br, or I;

$R^1$ is H or $C_1-C_6$ alkyl;

$R^2$, at each occurrence, is independently selected from methyl, ethyl, and propyl;

in a suitable polar aprotic solvent at a temperature from about 0° C. to 60° C. to form a compound of Formula (VI), a compound of Formula (VI*), or a mixture of compounds of Formula (VI) and (VI*):

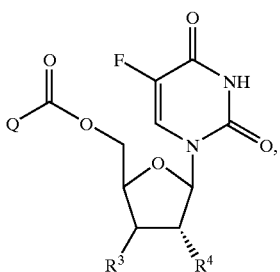
(VI)

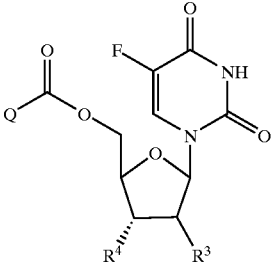
(VI*)

wherein R³ is X; and R⁴ is $R^1CH_2C(=O)O-$;

(2) contacting the compound of Formula (VI), the compound of Formula (VI*), or the mixture of compounds of Formula (VI) and (VI*); with a reducing agent in a suitable polar solvent, in the absence of an acid catalyst, to form a compound of Formula (VII):

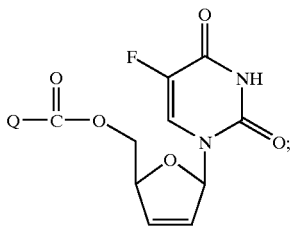
(VII)

(3a) contacting the compound of Formula (VII) with an activating agent in the presence of an amine base, to form a compound of Formula (VIII):

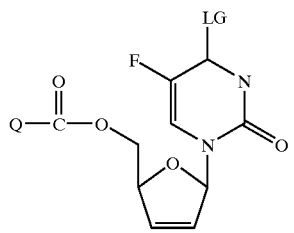
(VIII)

wherein LG is a leaving group derived from the activating agent;

(3b) contacting the compound of Formula (VIII) with an aminating agent to form a compound of Formula (III),

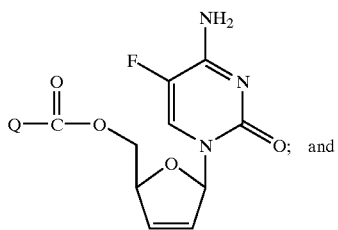
(III)

(4) contacting the compound of Formula (III) with a suitable base to form the compound of Formula (IV).

30. The process of claim 29 for the preparation of a compound of Formula (IV), wherein:

in step (1) the acyl halide of Formula Q—C(=O)X comprises:
2-acetoxy-2-methyl-propionyl bromide,
2-(acetoxy)-2-methyl-butanoyl bromide,
2-(acetoxy)-2-ethyl-butanoyl bromide, or
2-(acetoxy)-2-methyl-pentanoyl bromide;

in step (1), the suitable polar aprotic solvent comprises one polar aprotic solvent or a combination of two or more polar aprotic solvents, and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the reducing agent is selected from the group consisting of: Fe, Zn—Cu couple and Zn;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether;

in step (3a) the activating agent is selected from the group consisting of:
methanesulfonyl chloride, trifluoromethyl sulfonyl chloride, ethanesulfonyl chloride, benzenesulfonyl chloride,
p-toluene-sulfonyl chloride, triazole/phosphorus oxychloride and triazole/diphenyl chloro-phosphate;

in step (3a) the amine base is selected from the group consisting of: triethylamine, tributylamine, N-methylmorpholine, N,N-diisopropyl-ethylamine, N,N-dimethylcyclohexylamine, N,N-diethylcyclohexylamine, N,N-dimethyloctylamine, tetramethylethylenediamine, pyridine, N,N-dimethylaminopyridine, 1,4-diazabicyclo[2.2.2]octane, 1,8-diazabicyclo[5.4.0]undec-7-ene, and 1,5-diazabicyclo[4.3.0]non-5-ene;

in step (3a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl;

in step (3b) the aminating agent is selected from the group consisting of: $NH_3$, ammonium hydroxide, and ammonium carbonate; and in step (4) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

31. The process according to claim 29, for the preparation of a compound of Formula (IV):

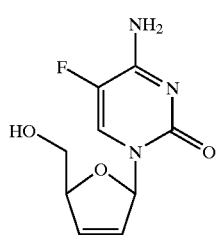
(IV)

comprising:

(1) contacting a compound of Formula (V):

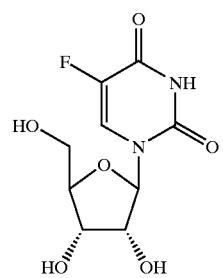
(V)

with 2-acetoxy-2-methyl-propionyl bromide in a suitable polar aprotic solvent to form a compound of Formula (VI-a), a compound of Formula (VI*-a), or a mixture of compounds of Formula (VI-a) and (VI*-a):

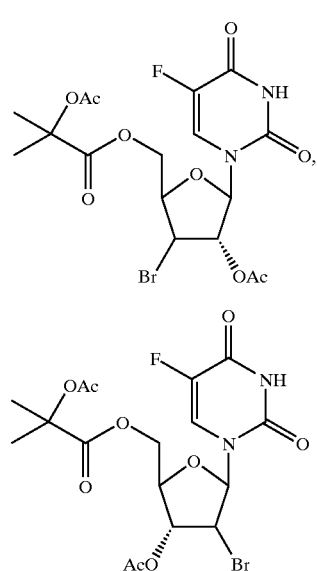
(VI-a)

(VI*-a)

(2) contacting the compound of Formula (VI-a), the compound of Formula (VI*-a), or the mixture of compounds of Formula (VI-a) and (VI*-a); with a reducing agent in a suitable polar solvent, in the absence of an acid catalyst, to form a compound of Formula (VII-a):

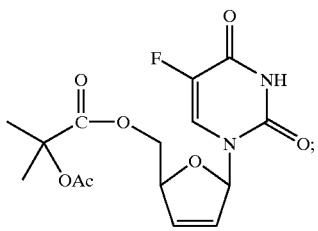
(VII-a)

(3a) contacting the compound of Formula (VII-a) with an activating agent selected from the group consisting of:
  i) an aryl sulfonyl halide,
  ii) an alkyl sulfonyl halide, and
  iii) 1,2,4-triazole in the presence of a phosphorus chloride;
in the presence of an amine base, to form a compound of Formula (VIII-a);

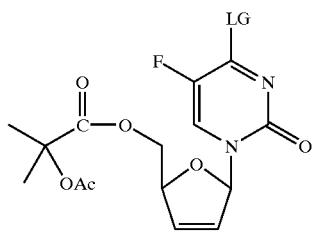
(VIII-a)

wherein LG is a leaving group derived from the activating agent;

(3b) contacting the compound of Formula (VIII-a) with an aminating agent to form a compound of Formula (III-a),

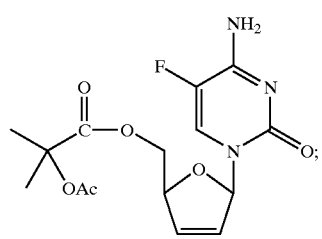
(III-a)

(4) contacting the compound of Formula (III-a) with a suitable base to form the compound of Formula (IV).

32. The process of claim 31 for the preparation of a compound of Formula (IV), wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the reducing agent is selected from the group consisting of: Fe, Zn—Cu couple and Zn;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether;

in step (3a) the activating agent is selected from the group consisting of:
methanesulfonyl chloride, trifluoromethyl sulfonyl chloride, ethanesulfonyl chloride, benzenesulfonyl chloride,
p-toluene-sulfonyl chloride, triazole/phosphorus oxychloride and triazole/diphenyl chloro-phosphate;

in step (3a) the amine base is selected from the group consisting of:
triethylamine,
tributylamine,
N-methylmorpholine, N,N-diisopropyl-ethylamine, tetramethylethylenediamine, pyridine, N,N-dimethyl-aminopyridine,
1,4-diazabicyclo[2.2.2]octane, and
1,8-diazabicyclo[5.4.0]undec-7-ene;

in step (3a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl;

in step (3b) the aminating agent is selected from the group: $NH_3$, ammonium hydroxide, and ammonium carbonate; and in step (4) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

33. The process of claim 32 for the preparation of a compound of Formula (IV), wherein:

in step (1), the suitable polar aprotic solvent comprises one solvent which is acetonitrile;

in step (2), the reducing agent is Zn—Cu couple;

in step (2), the suitable polar solvent comprises a combination of methanol and ethyl acetate;

in step (3a) the activating agent is triazole/phosphorus oxychloride;

in step (3a) the amine base is triethylamine;

in step (3a) the leaving group LG is triazolyl;

in step (3b), the aminating agent is $NH_3$; and in step (4) the suitable base is sodium methoxide.

34. The process according to claim 33, for the preparation of a compound of Formula (IV):

(IV)

comprising:
(1) contacting a compound of Formula (V):

(V)

with 2-acetoxy-2-methyl-propionyl bromide in acetonitrile to form a compound of Formula (VI-a), a compound of Formula (VI*-a), or a mixture of compounds of Formula (VI-a) and (VI*-a):

(VI-a)

(VI*-a)

(2) contacting the compound of Formula (VI-a), the compound of Formula (VI*-a), or the mixture of compounds of Formula (VI-a) and (VI*-a); with Zn—Cu couple in a suitable polar solvent comprising a combination of methanol and ethyl acetate, wherein the ratio of methanol to ethyl acetate is in the range of 1:2 to 1:4, to form a compound of Formula (VII-a):

(VII-a)

(3a) contacting the compound of Formula (VII-a) with 1,2,4-triazole/phosphorus oxychloride, in the presence of triethylamine, to form a compound of Formula (VII-a):

(VIII-a)

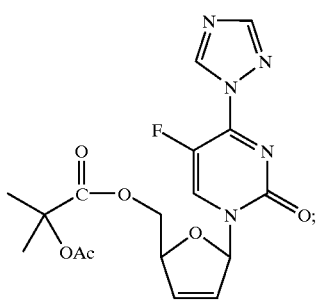

(3b) contacting the compound of Formula (VIII-a) with NH$_3$, to form a compound of Formula (III-a), and
(4) contacting the compound of Formula (III-a) with sodium methoxide to form the compound of Formula (IV).

35. The process of claim 29 for the preparation of a compound of Formula (IV):

(IV)

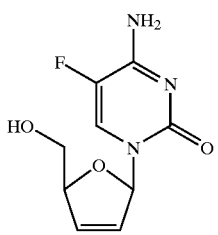

comprising:
(1) contacting a compound of Formula (V):

(V)

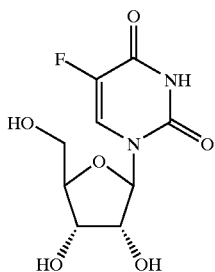

with an acyl halide of Formula Q—C(=O)X, wherein:
wherein LG is a leaving group derived from the activating agent;
(3b) contacting the compound of Formula (VIII) with an aminating agent to form a compound of Formula (III), (III)

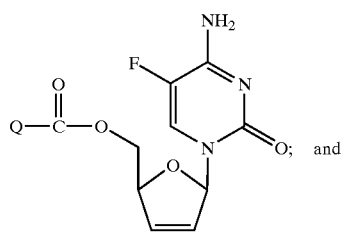

(4) contacting the compound of Formula (III) with a suitable base to form the compound of Formula (IV).

36. The process of claim 35 for the preparation of a compound of Formula (IV), wherein:
in step (1) the acyl halide of Formula Q—C(=O)X comprises:
2-acetoxy-2-methyl-propionyl bromide,
2-(acetoxy)-2-methyl-butanoyl bromide,
2-(acetoxy)-2-ethyl-butanoyl bromide, or
2-(acetoxy)-2-methyl-pentanoyl bromide;
in step (1), the suitable polar aprotic solvent comprises one polar aprotic solvent or a combination of two or more polar aprotic solvents, and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;
in step (2), the reducing agent is selected from the group consisting of: Fe, Zn—Cu couple and Zn;
in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether;
in step (3a) the activating agent is selected from the group consisting of:
methanesulfonyl chloride, trifluoromethyl sulfonyl chloride, ethanesulfonyl chloride, benzenesulfonyl chloride,
p-toluene-sulfonyl chloride, triazole/phosphorus oxychloride and triazole/diphenyl chloro-phosphate;
in step (3a) the amine base is selected from the group consisting of:
triethylamine,
tributylamine,
N-methylmorpholine, N,N-diisopropyl-ethylamine,
N,N-dimethylcyclohexylamine,
N,N-diethylcyclohexylamine,
N,N-dimethyloctylamine, tetramethylethylenediamine,
pyridine, N,N-dimethyl-aminopyridine,
1,4-diazabicyclo[2.2.2]octane,
1,8-diazabicyclo[5.4.0]undec-7-ene, and
1,5-diazabicyclo[4.3.0]non-5-ene;
in step (3a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl;
in step (3b) the aminating agent is selected from the group consisting of: NH$_3$, ammonium hydroxide, and ammonium carbonate; and
in step (4) the suitable base is selected from the group consisting of: sodium hydroxide, lithium hydroxide, potassium carbonate, sodium carbonate, sodium methoxide, sodium ethoxide, C$_3$–C$_6$ alkyl primary amine, ammonium hydroxide, and ammonium C$_1$–C$_6$ alkoxide.

37. The process according to claim 35, for the preparation of a compound of Formula (IV):

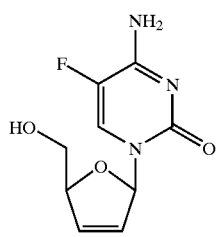

(IV)

comprising:

(1) contacting a compound of Formula (V):

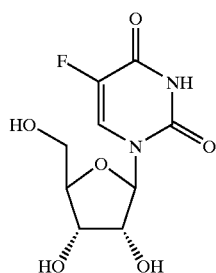

(V)

with 2-acetoxy-2-methyl-propionyl bromide in a suitable polar aprotic solvent to form a mixture of compounds of Formula (VI-a) and (VI*-a):

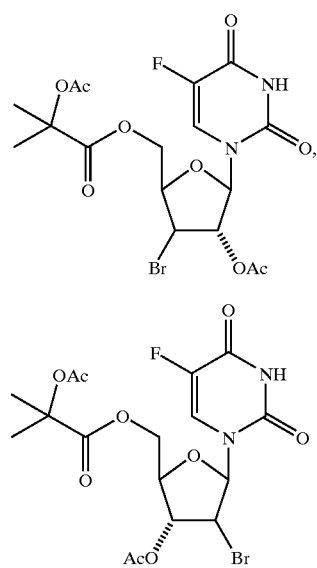

(VI-a)

(VI*-a)

(2) contacting the mixture of compounds of Formula (VI-a) and (VI*-a); with a reducing agent in a suitable polar solvent, in the absence of an acid catalyst, to form a compound of Formula (VII-a):

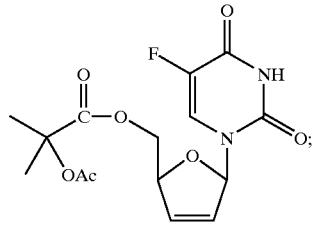

(VII-a)

(3a) contacting the compound of Formula (VII-a) with a activating agent selected from the group consisting of:
  i) an aryl sulfonyl halide,
  ii) an alkyl sulfonyl halide, and
  iii) 1,2,4-triazole in the presence of a phosphorus chloride;
in the presence of an amine base, to form a compound of Formula (VII-a);

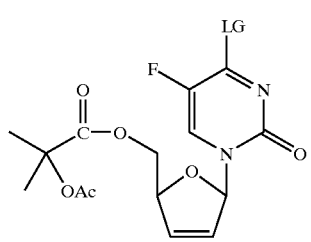

(VIII-a)

wherein LG is a leaving group derived from the activating agent;

(3b) contacting the compound of Formula (VIII-a) with an aminating agent to form a compound of Formula (III-a),

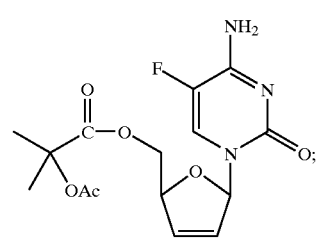

(III-a)

and (4) contacting the compound of Formula (III-a) with a suitable base to form the compound of Formula (IV).

38. The process of claim 37 for the preparation of a compound of Formula (IV), wherein:
  in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxyethane, 2-methoxyethyl ether, dimethylformamide, dimethylacetamide, acetonitrile, ethyl acetate, and isopropyl acetate;
  in step (2), the reducing agent is selected from the group consisting of: Fe, Zn—Cu couple and Zn;
  in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether;

in step (3a) the activating agent is selected from the group consisting of:
methanesulfonyl chloride, trifluoromethyl sulfonyl chloride, ethanesulfonyl chloride, benzenesulfonyl chloride,
p-toluene-sulfonyl chloride, triazole/phosphorus oxychloride and triazole/diphenyl chloro-phosphate;

in step (3a) the amine base is selected from the group consisting of:
triethylamine,
tributylamine,
N-methylmorpholine, N,N-diisopropyl-ethylamine, tetramethylethylenediamine, pyridine, N,N-dimethyl-aminopyridine,
1,4-diazabicyclo[2.2.2]octane, and
1,8-diazabicyclo[5.4.0]undec-7-ene;

in step (3a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl;

in step (3b) the aminating agent is selected from the group: $NH_3$, ammonium hydroxide, and ammonium carbonate; and in step (4) the suitable base is selected from the group consisting of: sodium hydroxide, lithium hydroxide, potassium carbonate, sodium carbonate, sodium methoxide, sodium ethoxide, $C_3$–$C_6$ alkyl primary amine, ammonium hydroxide, and ammonium $C_1$–$C_6$ alkoxide.

39. The process of claim 38 for the preparation of a compound of Formula (IV), wherein:
in step (1), the suitable polar aprotic solvent comprises one solvent which is acetonitrile;
in step (2), the reducing agent is Zn—Cu couple;
in step (2), the suitable polar solvent comprises a combination of methanol and ethyl acetate;
in step (3a) the activating agent is triazole/phosphorus oxychloride;
in step (3a) the amine base is triethylamine;
in step (3a) the leaving group LG is triazolyl;
in step (3b), the animating agent is $NH_3$; and
in step (4) the suitable base is sodium methoxide.

40. The process according to claim 39, for the preparation of a compound of Formula (IV):

(IV)

comprising:
(1) contacting a compound of Formula (V):

(V)

with 2-acetoxy-2-methyl-propionyl bromide in acetonitrile to form a mixture of compounds of Formula (VI-a) and (VI*-a):

(VI-a)

(VI*-a)

(2) contacting the mixture of compounds of Formula (VI-a) and (VI*-a); with Zn—Cu couple in a suitable polar solvent comprising a combination of methanol and ethyl acetate, wherein the ratio of methanol to ethyl acetate is in the range of 1:2 to 1:4 to form a compound of Formula (VII-a):

(VII-a)

(3a) contacting the compound of Formula (VII-a) with 1,2,4-triazole/phosphorus oxychloride, in the presence of triethylamine, to form a compound of Formula (VIII-a):

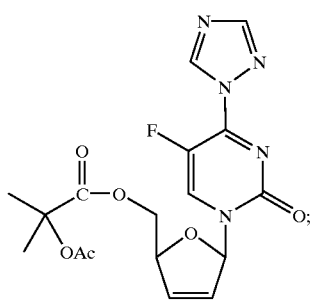

(VIII-a)

(3b) contacting the compound of Formula (VIII-a) with NH₃, to form a compound of Formula (III-a), and (4) contacting the compound of Formula (III-a) with sodium methoxide to form the compound of Formula (IV).

41. A process for the preparation of a compound of Formula (III):

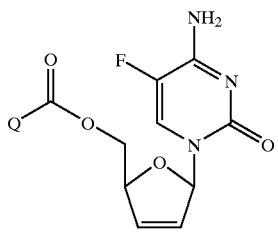

(III)

wherein:
Q is 2-(R¹CH₂CO₂)phenyl-, R¹CH₂—, or R¹CH₂C(=O)OC(R²)₂—;
R¹ is H or C₁–C₆ alkyl;
R², at each occurrence, is independently selected from methyl, ethyl, and propyl;

comprising:

(1) contacting a compound of Formula (V):

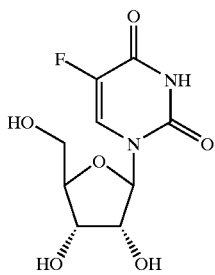

(V)

with an acyl halide of Formula Q—C(=O)X, wherein:
Q is 2-(R¹CH₂CO₂)phenyl-, R¹CH₂—, or R¹CH₂C(=O)OC(R²)₂—;
X is Cl, Br, or I;
R¹ is H or C₁–C₆ alkyl;
R², at each occurrence, is independently selected from methyl, ethyl, and propyl;
in a suitable polar aprotic solvent at a temperature from about 0° C. to 60° C. to form a compound of Formula (VI), a compound of Formula (VI*), or a mixture of compounds of Formula (VI) and (VI*):

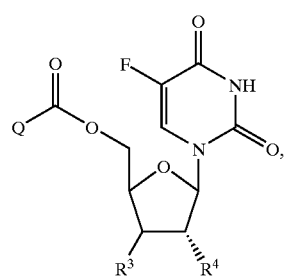

(VI)

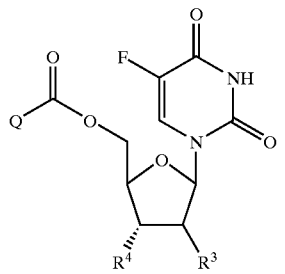

(VI*)

wherein R³ is X; and R⁴ is R¹CH₂C(=O)O—;

(2) contacting the compound of Formula (VI), the compound of Formula (VI*), or the mixture of compounds of Formula (VI) and (VI*); with a reducing agent in a suitable polar solvent, in the absence of an acid catalyst, to form a compound of Formula (VII):

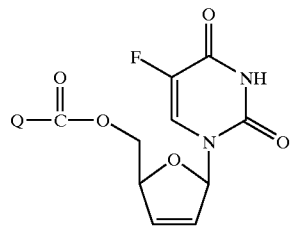

(VII)

(3a) contacting the compound of Formula (VII) with an activating agent in the presence of an amine base, to form a compound of Formula (VIII):

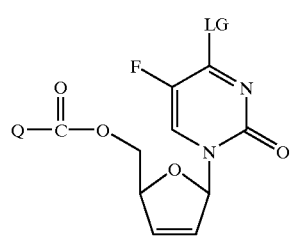

(VIII)

wherein LG is a leaving group derived from the activating agent;

(3b) contacting the compound of Formula (VIII) with an aminating agent to form a compound of Formula (III).

42. The process of claim 41 for the preparation of a compound of Formula (III), wherein:
in step (1) the acyl halide of Formula Q—C(=O)X comprises:

2-acetoxy-2-methyl-propionyl bromide,
2-(acetoxy)-2-methyl-butanoyl bromide,
2-(acetoxy)-2-ethyl-butanoyl bromide, or
2-(acetoxy)-2-methyl-pentanoyl bromide;
in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;
in step (2), the reducing agent is selected from the group consisting of: Fe, Zn—Cu couple and Zn;
in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether;
in step (3a) the activating agent is selected from the group consisting of:
methanesulfonyl chloride, trifluoromethyl sulfonyl chloride, ethanesulfonyl chloride, benzenesulfonyl chloride,
p-toluene-sulfonyl chloride, triazole/phosphorus oxychloride and triazole/diphenyl chloro-phosphate;
in step (3a) the amine base is selected from the group consisting of:
triethylamine,
tributylamine,
N-methylmorpholine, N,N-diisopropyl-ethylamine,
N,N-dimethylcyclohexylamine,
N,N-diethylcyclohexylamine,
N,N-dimethyloctylamine, tetramethylethylenediamine,
pyridine, N,N-dimethyl-aminopyridine,
1,4-diazabicyclo[2.2.2]octane,
1,8-diazabicyclo[5.4.0]undec-7-ene, and
1,5-diazabicyclo[4.3.0]non-5-ene;
in step (3a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl;
in step (3b) the aminating agent is selected from the group: $NH_3$, ammonium hydroxide, and ammonium carbonate.

43. The process according to claim 41, for the preparation of a compound of Formula (III-a):

(III-a)

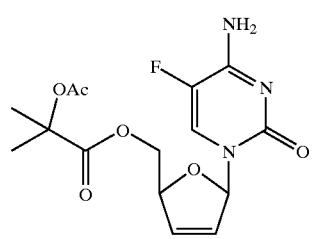

comprising:
(1) contacting a compound of Formula (V):

(V)

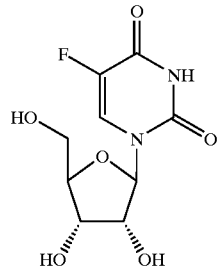

with 2-acetoxy-2-methyl-propionyl bromide in a suitable polar aprotic solvent to form a compound of Formula (VI-a), a compound of Formula (VI*-a), or a mixture of compounds of Formula (VI-a) and (VI*-a):

(VI-a)

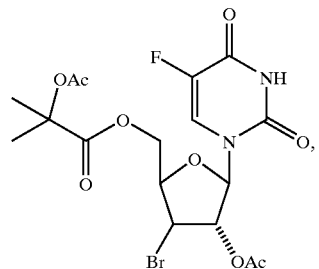

(VI*-a)

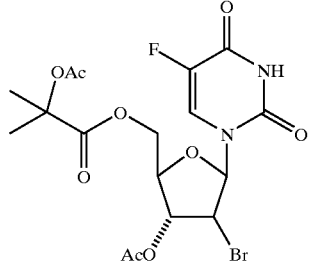

(2) contacting the compound of Formula (VI-a), the compound of Formula (VI*-a), or the mixture of compounds of Formula (VI-a) and (VI*-a); with a reducing agent in a suitable polar solvent, in the absence of an acid catalyst, to form a compound of Formula (VII-a);

(VII-a)

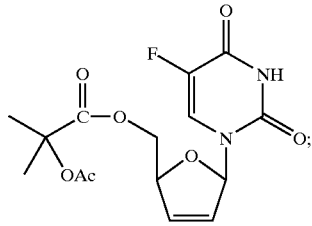

(3a) contacting the compound of Formula (VII-a) with a activating agent selected from the group consisting of:
i) an aryl sulfonyl halide,
ii) an alkyl sulfonyl halide, and
iii) 1,2,4-triazole in the presence of a phosphorus chloride;
in the presence of an amine base, to form a compound of Formula (VIII-a):

(VIII-a)

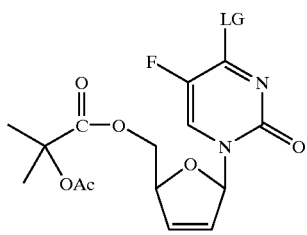

wherein LG is a leaving group derived from the activating agent; and (3b) contacting the compound of Formula (VIII-a) with an aminating agent to form a compound of Formula (III-a).

44. The process of claim 43 for the preparation of a compound of Formula (III-a), wherein:

in step (1), the suitable polar aprotic solvent comprises one polar aprotic solvent or a combination of two or more polar aprotic solvents; and is selected from the group consisting of: methylene chloride, tetrahydrofuran, t-butyl methyl ether, dimethoxy ethane, 2-methoxyethyl ether, dimethylformamide, dimethylacetamide, acetonitrile, ethyl acetate, and isopropyl acetate;

in step (2), the reducing agent is selected from the group consisting of: Fe, Zn—Cu couple and Zn;

in step (2), the suitable polar solvent comprises one polar solvent or a combination of two or more polar solvents; and is selected from the group consisting of: methanol, ethanol, propanol, ethyl acetate, propyl acetate, butyl acetate, isopropyl acetate, acetonitrile, tetrahydrofuran, dimethoxy ethane, and 2-methoxyethyl ether; and in step (3a) the activating agent is selected from the group consisting of:
methanesulfonyl chloride, trifluoromethyl sulfonyl chloride, ethanesulfonyl chloride, benzenesulfonyl chloride,
p-toluene-sulfonyl chloride, triazole/phosphorus oxychloride and triazole/diphenyl chloro-phosphate;

in step (3a) the amine base is selected from the group consisting of:
triethylamine,
tributylamine,
N-methylmorpholine, N,N-diisopropyl-ethylamine, tetramethylethylenediamine, pyridine,
N,N-dimethyl-aminopyridine,
1,4-diazabicyclo[2.2.2]octane, and
1,8-diazabicyclo[5.4.0]undec-7-ene;

in step (3a) the leaving group LG is selected from the group consisting of methanesulfonyloxy, trifluoromethyl-sulfonyloxy, ethanesulfonyloxy, benzenesulfonyloxy, toluenesulfonyloxy, and triazolyl; and in step (3b) the aminating agent is selected from the group: NH₃, ammonium hydroxide, and ammonium carbonate.

45. The process of claim 44 for the preparation of a compound of Formula (III-a), wherein:

in step (I), the suitable polar aprotic solvent comprises one solvent which is acetonitrile;
in step (2), the reducing agent is Zn—Cu couple;
in step (2), the suitable polar solvent comprises a combination of methanol and ethyl acetate;

in step (3a) the activating agent is triazole/phosphorus oxychloride;
in step (3a) the amine base is triethylamine;
in step (3a) the leaving group LG is triazolyl; and
in step (3b), the animating agent is NH₃.

46. The process according to claim 45, for the preparation of a compound of Formula (III-a):

(III-a)

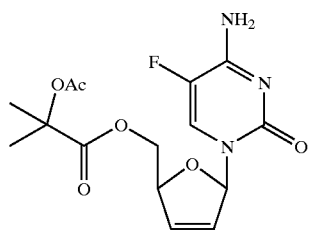

comprising:

(1) contacting a compound of Formula (V):

(V)

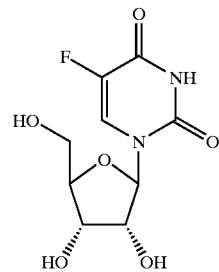

with 2-acetoxy-2-methyl-propionyl bromide in acetonitrile to form a compound of Formula (VI-a), a compound of Formula (VI*-a), or a mixture of compounds of Formula (VI-a) and (VI*-a):

(VI-a)

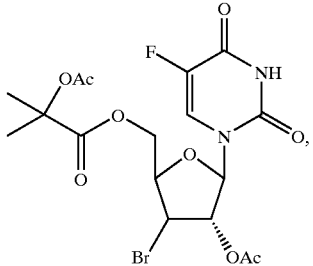

(VI*-a)

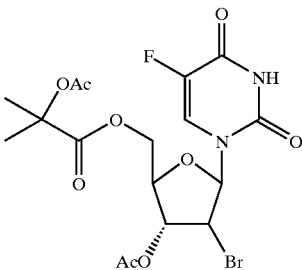

(2) contacting the compound of Formula (VI-a), the compound of Formula (VI*-a), or the mixture of compounds of Formula (VI-a) and (VI*-a); with Zn—Cu couple in a suitable polar solvent comprising a combination of methanol and ethyl acetate, wherein the ratio of methanol to ethyl acetate is in the range of 1:2 to 1:4, to form a compound of Formula (VII-a):

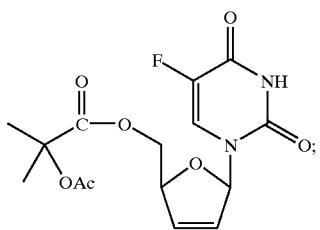

(VII-a)

(3a) contacting the compound of Formula (VII-a) with 1,2,4-triazole/phosphorus oxychloride, in the presence of triethylamine, to form a compound of Formula (VIII-a):

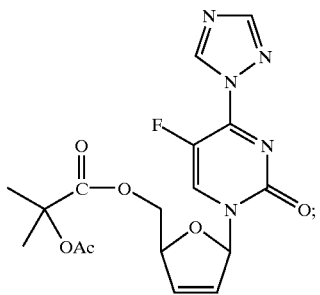

(VIII-a)

and (3b) contacting the compound of Formula (VIII-a) with $NH_3$, to form a compound of Formula (III-a).

47. The process of claim 1 or 29 wherein the compound of Formula (IV) is in the form of a β-D-enantiomer.

48. The process of claim 19 or 41 wherein the compound of Formula (III) is in the form of a β-D-enantiomer.

49. The compound of claim 25 wherein the compound of Formula (II) or (II*) is in the form of a β-D-enantiomer.

50. The compound of claim 26 wherein the compound of Formula (II-a) or (II*-a) is in the form of a β-D-enantiomer.

51. The compound of claim 27 wherein the compound of Formula (III) is in the form of a β-D-enantiomer.

52. The compound of claim 28 wherein the compound of Formula (III-a) is in the form of a β-D-enantiomer.

53. The process of claim 1 wherein the temperature in step (1) is about 10° C. to about 40° C.

54. The process of claim 1 wherein the temperature in step (1) is about 25° C. to about 40° C.

55. The process of claim 19 wherein the temperature in step (1) is about 10° C. to about 40° C.

56. The process of claim 19 wherein the temperature in step (1) is about 25° C. to about 40° C.

57. The process of claim 29 wherein the temperature in step (1) is about 10° C. to about 40° C.

58. The process of claim 29 wherein the temperature in step (1) is about 25° C. to about 40° C.

59. The process of claim 41 wherein the temperature in step (1) is about 10° C. to about 40° C.

60. The process of claim 41 wherein the temperature in step (1) is about 25° C. to about 40° C.

* * * * *